(12) United States Patent
DeMong et al.

(10) Patent No.: US 8,633,231 B2
(45) Date of Patent: Jan. 21, 2014

(54) SUBSTITUTED IMIDAZOLONES, COMPOSITIONS CONTAINING SUCH COMPOUNDS AND METHODS OF USE

(75) Inventors: Duane DeMong, Somerset, NJ (US); Michael W. Miller, Scotch Plains, NJ (US); Xing Dai, Cranford, NJ (US); Andrew Stamford, Chatham Township, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/808,618

(22) PCT Filed: Jul. 8, 2011

(86) PCT No.: PCT/US2011/043369
§ 371 (c)(1),
(2), (4) Date: Jan. 7, 2013

(87) PCT Pub. No.: WO2012/009226
PCT Pub. Date: Jan. 19, 2012

(65) Prior Publication Data
US 2013/0123315 A1    May 16, 2013

Related U.S. Application Data

(60) Provisional application No. 61/363,812, filed on Jul. 13, 2010.

(51) Int. Cl.
*A61K 31/4178* (2006.01)
*A61K 31/4166* (2006.01)
*C07D 233/36* (2006.01)
*C07D 403/12* (2006.01)

(52) U.S. Cl.
USPC ......... 514/381; 514/386; 548/251; 548/253; 548/324.1

(58) Field of Classification Search
USPC ............................. 548/251–325.5
See application file for complete search history.

(56) References Cited

U.S. PATENT DOCUMENTS

| | | |
|---|---|---|
| 2008/0070867 A1 | 3/2008 | Cheruvallath et al. |
| 2010/0004159 A1 | 1/2010 | Bouey et al. |
| 2011/0178007 A1 | 7/2011 | Stamford et al. |

FOREIGN PATENT DOCUMENTS

| | | |
|---|---|---|
| WO | 2009/140342 A1 | 11/2009 |
| WO | 2010/039789 A1 | 4/2010 |
| WO | 2011/119541 A1 | 9/2011 |
| WO | 2011/119559 A1 | 9/2011 |

*Primary Examiner* — Samantha Shterengarts
*Assistant Examiner* — Amanda L Aguirre
(74) *Attorney, Agent, or Firm* — Anna L. Cocuzzo; Catherine D. Fitch

(57) ABSTRACT

The present invention relates to compounds of the general structure shown in Formula (A): (A): and includes pharmaceutically acceptable salts, solvates, esters, prodrugs, tautomers, and isomers of said compounds. Pharmaceutical compositions and methods of treatment are also included.

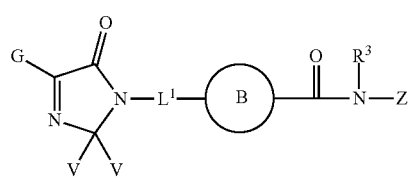

(A)

16 Claims, No Drawings

SUBSTITUTED IMIDAZOLONES, COMPOSITIONS CONTAINING SUCH COMPOUNDS AND METHODS OF USE

FIELD OF THE INVENTION

The present invention relates to compounds that are useful as glucagon receptor antagonists, compositions comprising these compounds, and methods for their use in treating, preventing, or delaying the onset of type 2 diabetes and related conditions.

BACKGROUND OF THE INVENTION

Diabetes refers to a disease state or process derived from multiple causative factors and is characterized by elevated levels of plasma glucose (hyperglycemia) in the fasting state or after administration of glucose during a glucose tolerance test. Persistent or uncontrolled hyperglycemia is associated with a wide range of pathologies. Frank diabetes mellitus (e.g., fasting blood glucose levels above about 126 mg/dL) is associated with increased and premature cardiovascular disease and premature mortality, and is related directly and indirectly to various metabolic conditions, including alterations of lipid, lipoprotein, apolipoprotein metabolism and other metabolic and hemodynamic diseases. As such, the diabetic patient is at increased risk of macrovascular and microvascular complications. Such complications can lead to diseases and conditions such as coronary heart disease, stroke, peripheral vascular disease, hypertension, nephropathy, neuropathy, and retinopathy. Accordingly, therapeutic control and correction of glucose homeostasis is regarded as important in the clinical management and treatment of diabetes mellitus.

There are two generally recognized forms of diabetes. In type 1 diabetes, or insulin-dependent diabetes mellitus (IDDM), the diabetic patient's pancreas is incapable of producing adequate amounts of insulin, the hormone which regulates glucose uptake and utilization by cells. In type 2 diabetes, or noninsulin dependent diabetes mellitus (NIDDM), patients often produce plasma insulin levels comparable to those of nondiabetic subjects; however, the cells of patients suffering from type 2 diabetes develop a resistance to the effect of insulin, even in normal or elevated plasma levels, on glucose and lipid metabolism, especially in the main insulin-sensitive tissues (muscle, liver and adipose tissue).

Insulin resistance is not associated with a diminished number of cellular insulin receptors but rather with a post-insulin receptor binding defect that is not well understood. This cellular resistance to insulin results in insufficient insulin activation of cellular glucose uptake, oxidation, and storage in muscle, and inadequate insulin repression of lipolysis in adipose tissue, and of glucose production and secretion in the liver. A net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

The available treatments for type 2 diabetes, some of which have not changed substantially in many years, are used alone and in combination. Many of these treatments have recognized limitations, however. For example, while physical exercise and reductions in dietary intake of fat, high glycemic carbohydrates, and calories can dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic beta-cells to secrete more insulin, and/or by injection of insulin when sulfonylureas or meglitinide become ineffective, can result in insulin concentrations high enough to stimulate insulin-resistance in tissues. However, dangerously low levels of plasma glucose can result from administration of insulin or insulin secretagogues (sulfonylureas or meglitinide), and an increased level of insulin resistance due to the even higher plasma insulin levels can occur. The biguanides are a separate class of agents that can increase insulin sensitivity and bring about some degree of correction of hyperglycemia. These agents, however, can induce lactic acidosis, nausea and diarrhea.

The glitazones (i.e. 5-benzylthiazolidine-2,4-diones) are another class of compounds that have proven useful for the treatment of type 2 diabetes. These agents increase insulin sensitivity in muscle, liver and adipose tissue in several animal models of type 2 diabetes, resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensitization that is observed with the glitazones. Newer PPAR agonists that are being tested for treatment of Type II diabetes are agonists of the alpha, gamma or delta subtype, or a combination thereof, and in many cases are chemically different from the glitazones (i.e., they are not thiazolidinediones). Serious side effects (e.g. liver toxicity) have been noted in some patients treated with glitazone drugs, such as troglitazone.

Compounds that are inhibitors of the dipeptidyl peptidase-IV (DPP-IV) enzyme are also under investigation or available as drugs for the treatment of diabetes, and particularly type 2 diabetes. Examples include alogliptin (Takeda), saxagliptin (Brystol-Myers Squibb), sitagliptin (Januvia™, Merck), vildagliptin (Galvus™, Novartis), denagliptin (GlaxoSmithKline), ABT-279 and ABT-341 (Abbott), ALS-2-0426 (Alantos), ARI-2243 (Arisaph), BI-A and BI-B (Boehringer Ingelheim), SYR-322 (Takeda), compounds disclosed in U.S. Pat. No. 6,699,871, MP-513 (Mitsubishi), DP-893 (Pfizer), RO-0730699 (Roche) and combinations thereof.

Additional methods of treating hyperglycemia and diabetes are currently under investigation. New biochemical approaches include treatment with alpha-glucosidase inhibitors (e.g. acarbose) and protein tyrosine phosphatase-1B (PTP-1B) inhibitors.

Other approaches to treating hyperglycemia, diabetes, and indications attendant thereto have focused on the glucagon hormone receptor. Glucagon and insulin are the two primary hormones regulating plasma glucose levels. Insulin, released in response to a meal, increases the uptake of glucose into insulin-sensitive tissues such as skeletal muscle and fat. Glucagon, which is secreted by alpha cells in pancreatic islets in response to decreased postprandial glucose levels or during fasting, signals the production and release of glucose from the liver. Glucagon binds to specific receptors in liver cells that trigger glycogenolysis and an increase in gluconeogenesis through cAMP-mediated events. These responses generate increases in plasma glucose levels (e.g., hepatic glucose production), which help to regulate glucose homeostasis.

Type 2 diabetic patients typically have fasting hyperglycemia that is associated with elevated rates of hepatic glucose production. This is due to increased gluconeogenesis coupled with hepatic insulin resistance. Such patients typically have a relative deficiency in their fasting and postprandial insulin-to-glucagon ratio that contributes to their hyperglycemic state. Several studies have demonstrated that hepatic glucose production correlates with fasting plasma glucose levels, suggesting that chronic hepatic glucagon receptor antagonism should improve this condition. In addition, defects in rapid postprandial insulin secretion, as well as ineffective suppression of glucagon secretion, lead to increased glucagon levels that elevate hepatic glucose production and contribute to hyperglycemia. Suppression of elevated postprandial glucagon levels in type 2 diabetics with somatostatin has been shown to lower blood glucose concentrations. This indicates that acute postprandial glucagon receptor antagonism would also be beneficial. Based on these and other data, glucagon receptor antagonism holds promise as a potential treatment of type 2 diabetes by reducing hyperglycemia. There is thus a need in the art for small-molecule glucagon receptor antagonists with good safety profiles and efficacy that are useful for the treatment of hyperglycemia, diabetes, and related metabolic diseases and indications. The present invention addresses that need.

SUMMARY OF THE INVENTION

The present invention relates to compounds represented by Formula (A):

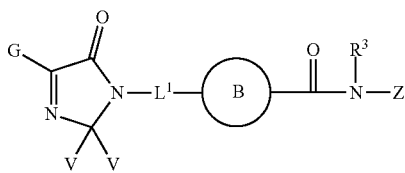

(A)

as well as the pharmaceutically acceptable salts, solvates, esters, prodrugs, tautomers and isomers of said compounds. Pharmaceutical compositions and methods of treatment are also included.

DETAILED DESCRIPTION OF THE INVENTION

In one embodiment, the present invention relates to compounds of the general structure shown in Formula (A):

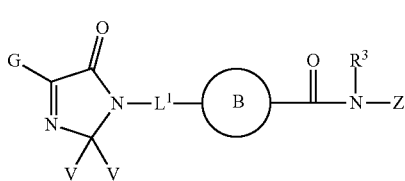

(A)

and includes pharmaceutically acceptable salts thereof, wherein:

A compound represented by Formula (A):

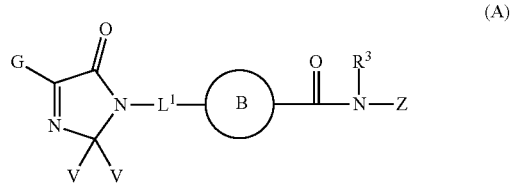

(A)

or a pharmaceutically acceptable salt thereof, wherein:
$L^1$ is selected from the group consisting of a bond, —N($R^4$)—, —N($R^4$)—(C($R^{5A}$)$_2$)—(C($R^5$)$_2$)$_q$—, —(C($R^{5A}$)$_2$)—(C($R^5$)$_2$)$_r$—(C($R^{5A}$)$_2$)—N($R^4$)—, —O—, —O—(C($R^{5A}$)$_2$)—(C($R^5$)$_2$)$_q$—, —(C($R^{5A}$)$_2$)—(C($R^5$)$_2$)$_r$—(C($R^{5A}$)$_2$)—O— and —(C($R^{5A}$)$_2$)—(C($R^5$)$_2$)$_s$—, each q is independently an integer from 0 to 5;
each r is independently an integer from 0 to 3;
s is an integer from 0 to 5;

ring B is a phenyl ring, wherein said phenyl ring is (in addition to the -$L^1$- and —C(O)N($R^3$)—Z moieties shown) optionally further substituted with one or more substituents $R^a$, wherein each $R^a$ (when present) is independently selected from the group consisting of halo, —OH, —SF$_5$, —OSF$_5$, alkyl, haloalkyl, heteroalkyl, hydroxyalkyl, alkoxy and —O-haloalkyl, or ring B is a 5-membered heteroaromatic ring containing from 1 to 3 ring heteroatoms independently selected from N, O, and S, wherein said 5-membered heteroaromatic ring is (in addition to the -$L^1$- and —C(O)N($R^3$)—Z moieties shown) optionally further substituted with one or more substituents $R^a$, wherein each $R^a$ (when present) is independently selected from the group consisting of halo, —OH, —SF$_5$, —OSF$_5$, alkyl, haloalkyl, heteroalkyl, hydroxyalkyl, alkoxy and —O-haloalkyl, or ring B is a 6-membered heteroaromatic ring containing from 1 to 3 ring nitrogen atoms, wherein said 6-membered heteroaromatic ring is (in addition to -$L^1$- and —C(O)N($R^3$)Z moieties shown) optionally further substituted with one or more substituents $R^a$, wherein each $R^a$ (when present) is independently selected from the group consisting of halo, —OH, —SF$_5$, —OSF$_5$, alkyl, haloalkyl, hydroxyalkyl, alkoxy, and —O-haloalkyl;

each V is independently selected from the group consisting of alkyl, heteroalkyl, alkenyl, alkynyl, cycloalkyl, heterocycloalkyl, cycloalkenyl, heterocycloalkenyl, aryl, and heteroaryl, wherein said heteroalkyl, said heterocycloalkyl, said heterocycloalkenyl, and said heteroaryl of V may only be connected through carbon, and wherein said alkyl, said heteroalkyl, said alkenyl, said alkynyl, said cycloalkyl, said heterocycloalkyl, said cycloalkenyl, said heterocycloalkenyl, said aryl, and said heteroaryl of V are unsubstituted or optionally substituted with one or more groups independently selected from:

(1) halo, —NH$_2$, —OH, —SH, —SO$_2$H, CO$_2$H, —SF$_5$, —OSF$_5$, cyano and —CHO, (2) cycloalkyl, —O-cycloalkyl, —C(O)-cycloalkyl, —CO$_2$-cycloalkyl, —S-cycloalkyl, —S(O)-cycloalkyl, —S(O)$_2$-cycloalkyl, —N($R^1$)-cycloalkyl, —C(O)—N($R^{21}$)-cycloalkyl, —N($R^{21}$)—C(O)-cycloalkyl, —N($R^{21}$)—C(O)—N($R^{21}$)-cycloalkyl, —N($R^{21}$)—S(O)-cycloalkyl, N($R^{21}$)—S(O)$_2$-cycloalkyl, —N($R^{21}$)—S(O)$_2$—N($R^{21}$)-cycloalkyl, —S(O)—N($R^{21}$)-cycloalkyl and —S(O)$_2$—N($R^{21}$)-cycloalkyl, (3) heterocycloalkyl, —O-heterocycloalkyl, —C(O)-heterocycloalkyl, —CO$_2$-heterocycloalkyl, —S-heterocycloalkyl, —S(O)-heterocycloalkyl, —S(O)$_2$-heterocycloalkyl, —N(R$^1$)-heterocycloalkyl, —C(O)—N(R$^{21}$)-heterocycloalkyl, —N(R$^{21}$)—C(O)-heterocycloalkyl, —N(R$^{21}$)—C(O)—N(R$^{21}$)-heterocycloalkyl, —N(R$^{21}$)—S(O)-heterocycloalkyl, —N(R$^{21}$)—S(O)$_2$-heterocycloalkyl, —N(R$^{21}$)—S(O)$_2$—N(R$^{21}$)-heterocycloalkyl, —S(O)—N(R$^{21}$)-heterocycloalkyl and —S(O)$_2$—N(R$^{21}$)-heterocycloalkyl, (4) cycloalkenyl, —O-cycloalkenyl, —C(O)-cycloalkenyl, —CO$_2$-cycloalkenyl, —S-cycloalkenyl, —S(O)-cycloalkenyl, —S(O)$_2$-cycloalkenyl, —N(R$^1$)-cycloalkenyl, —C(O)—N(R$^{21}$)-cycloalkenyl, —N(R$^{21}$)—C(O)-cycloalkenyl, —N(R$^{21}$)—C(O)—N(R$^{21}$)-cycloalkenyl, —N(R$^{21}$)—S(O)-cycloalkenyl, —N(R$^{21}$)—S(O)$_2$-cycloalkenyl, —N(R$^{21}$)—S(O)$_2$—N(R$^{21}$)-cycloalkenyl, —S(O)—N(R$^{21}$)-cycloalkenyl and —S(O)$_2$—N(R$^{21}$)-cycloalkenyl, (5) heterocycloalkenyl, —O-heterocycloalkenyl, —C(O)-heterocycloalkenyl, —CO$_2$-heterocycloalkenyl, —S-heterocycloalkenyl, —S(O)-heterocycloalkenyl, —S(O)$_2$-heterocycloalkenyl, —N(R$^1$)-heterocycloalkenyl, —C(O)—N(R$^{21}$)-heterocycloalkenyl, and —N(R$^{21}$)—C(O)-heterocycloalkenyl, —N(R$^{21}$)—C(O)—N(R$^{21}$)-heterocycloalkenyl, —N(R$^{21}$)—S(O)-heterocycloalkenyl, —N(R$^{21}$)—S(O)$_2$-heterocycloalkenyl, —N(R$^{21}$)—S(O)$_2$—N(R$^{21}$)-heterocycloalkenyl, —S(O)—N(R$^{21}$)-heterocycloalkenyl and —S(O)$_2$—N(R$^{21}$)— heterocycloalkenyl, (6) alkyl, —O-alkyl, —C(O)-alkyl, —CO$_2$-alkyl, —S-alkyl, —S(O)-alkyl, —S(O)$_2$-alkyl, —N(R$^1$)-alkyl, —C(O)—N(R$^{21}$)-alkyl, —N(R$^{21}$)—C(O)-alkyl, —N(R$^{21}$)—C(O)—N(R$^{21}$)-alkyl, —N(R$^{21}$)—S(O)-alkyl, —N(R$^{21}$)—S(O)$_2$-alkyl, —N(R$^{21}$)—S(O)$_2$—N(R$^{21}$)-alkyl, —S(O)—N(R$^{21}$)-alkyl and —S(O)$_2$—N(R$^{21}$)-alkyl, (7) heteroalkyl, —O-heteroalkyl, —C(O)-heteroalkyl, —CO$_2$-heteroalkyl, —S-heteroalkyl, —S(O)-heteroalkyl, —S(O)$_2$-heteroalkyl, —N(R$^1$)-heteroalkyl, —C(O)—N(R$^{21}$)-heteroalkyl, —N(R$^{21}$)—C(O)-heteroalkyl, —N(R$^{21}$)—C(O)—N(R$^{21}$)-heteroalkyl, —N(R$^{21}$)—S(O)-heteroalkyl, —N(R$^{21}$)—S(O)$_2$-heteroalkyl, —N(R$^{21}$)—S(O)$_2$—N(R$^{21}$)-heteroalkyl, —S(O)—N(R$^{21}$)-heteroalkyl and —S(O)$_2$—N(R$^{21}$)-heteroalkyl, (8) alkenyl, —O-alkenyl, —C(O)-alkenyl, —CO$_2$-alkenyl, —S-alkenyl, —S(O)-alkenyl, —S(O)$_2$-alkenyl, —N(R$^1$)-alkenyl, —C(O)—N(R$^{21}$)-alkenyl, —N(R$^{21}$)—C(O)-alkenyl, —N(R$^{21}$)—C(O)—N(R$^{21}$)-alkenyl, —N(R$^{21}$)—S(O)-alkenyl, —N(R$^{21}$)—S(O)$_2$-alkenyl, —N(R$^{21}$)—S(O)$_2$—N(R$^{21}$)-alkenyl, —S(O)—N(R$^{21}$)-alkenyl and —S(O)$_2$—N(R$^{21}$)-alkenyl, (9) alkynyl, —O-alkynyl, —C(O)-alkynyl, —CO$_2$-alkynyl, —S-alkynyl, S(O)-alkynyl, —S(O)$_2$-alkynyl, —N(R$^1$)-alkynyl, —C(O)—N(R$^{21}$)-alkynyl, —N(R$^{21}$)—C(O)-alkynyl, —N(R$^{21}$)—C(O)—N(R$^{21}$)-alkynyl, —N(R$^{21}$)—S(O)-alkynyl, —N(R$^{21}$)—S(O)$_2$-alkynyl, —N(R$^{21}$)—S(O)$_2$—N(R$^{21}$)-alkynyl, —S(O)—N(R$^{21}$)-alkynyl and —S(O)$_2$—N(R$^{21}$)-alkynyl,

(10) aryl, —O-aryl, —C(O)-aryl, —CO$_2$-aryl, —S-aryl, —S(O)-aryl, —S(O)$_2$-aryl, —N(R$^1$)-aryl, —C(O)—N(R$^{21}$)-aryl, —N(R$^{21}$)—C(O)-aryl, —N(R$^{21}$)—C(O)—N(R$^{21}$)-aryl, —N(R$^{21}$)—S(O)-aryl, —N(R$^{21}$)—S(O)$_2$-aryl, —N(R$^{21}$)—S(O)$_2$—N(R$^{21}$)-aryl, —S(O)—N(R$^{21}$)-aryl and —S(O)$_2$—N(R$^{21}$)-aryl,

(11) heteroaryl, —O-heteroaryl, —C(O)-heteroaryl, —CO$_2$-heteroaryl, —S-heteroaryl, —S(O)-heteroaryl, —S(O)$_2$-heteroaryl, —N(R$^{21}$)-heteroaryl, —C(O)—N(R$^{21}$)-heteroaryl, —N(R$^{21}$)—C(O)-heteroaryl, —N(R$^{21}$)—C(O)—N(R$^{21}$)-heteroaryl, —N(R$^{21}$)—S(O)-heteroaryl, —N(R$^{21}$)—S(O)$_2$-heteroaryl, —N(R$^{21}$)—S(O)$_2$—N(R$^{21}$)-heteroaryl, —S(O)—N(R$^{21}$)-heteroaryl and —S(O)$_2$—N(R$^{21}$)-heteroaryl, wherein said heteroalkyl of (7), said heterocycloalkyl of (3), said heterocycloalkenyl of (5), and said heteroaryl of (11) may be connected through any available carbon or heteroatom, and wherein said alkyl, said heteroalkyl, said cycloalkyl, said heterocycloalkyl, said aryl, said heteroaryl, said alkenyl, said alkynyl, said cycloalkenyl, and said heterocycloalkenyl of (1) through (11) are unsubstituted or substituted with one or more groups independently selected from R$^2$, G is selected from the group consisting of:

(1a) hydrogen, halo, —NH$_2$, —OH, —SH, —SO$_2$H, CO$_2$H, —SF$_5$, —OSF$_5$, cyano and —CHO, (2a) cycloalkyl, —O-cycloalkyl, —C(O)-cycloalkyl, —CO$_2$-cycloalkyl, —S-cycloalkyl, —S(O)-cycloalkyl, —S(O)$_2$-cycloalkyl, —N(R$^1$)-cycloalkyl, —C(O)—N(R$^{21}$)-cycloalkyl, —N(R$^{21}$)—C(O)-cycloalkyl, —N(R$^{21}$)—C(O)—N(R$^{21}$)-cycloalkyl, —N(R$^{21}$)—S(O)-cycloalkyl, —N(R$^{21}$)—S(O)$_2$-cycloalkyl, —N(R$^{21}$)—S(O)$_2$—N(R$^{21}$)-cycloalkyl, —S(O)—N(R$^{21}$)-cycloalkyl and —S(O)$_2$—N(R$^{21}$)-cycloalkyl, (3a) heterocycloalkyl, —O-heterocycloalkyl, —C(O)-heterocycloalkyl, —CO$_2$-heterocycloalkyl, —S-heterocycloalkyl, —S(O)-heterocycloalkyl, —S(O)$_2$-heterocycloalkyl, —N(R$^1$)-heterocycloalkyl, —C(O)—N(R$^{21}$)-heterocycloalkyl, —N(R$^{21}$)—C(O)-heterocycloalkyl, —N(R$^{21}$)—C(O)—N(R$^{21}$)-heterocycloalkyl, —N(R$^{21}$)—S(O)-heterocycloalkyl, —N(R$^{21}$)—S(O)$_2$-heterocycloalkyl, —N(R$^{21}$)—S(O)$_2$—N(R$^{21}$)-heterocycloalkyl, —S(O)—N(R$^{21}$)-heterocycloalkyl and —S(O)$_2$—N(R$^{21}$)-heterocycloalkyl, (4a) cycloalkenyl, —O-cycloalkenyl, —C(O)-cycloalkenyl, —CO$_2$-cycloalkenyl, —S-cycloalkenyl, —S(O)-cycloalkenyl, —S(O)$_2$-cycloalkenyl, —N(R$^1$)-cycloalkenyl, C(O)—N(R$^{21}$)-cycloalkenyl, —N(R$^{21}$)—C(O)-cycloalkenyl, —N(R$^{21}$)—C(O)—N(R$^{21}$)-cycloalkenyl, —N(R$^{21}$)—S(O)-cycloalkenyl, —N(R$^{21}$)—S(O)$_2$-cycloalkenyl, —N(R$^{21}$)—S(O)$_2$—N(R$^{21}$)-cycloalkenyl, —S(O)—N(R$^{21}$)-cycloalkenyl and —S(O)$_2$—N(R$^{21}$)-cycloalkenyl, (5a) heterocycloalkenyl, —O-heterocycloalkenyl, —C(O)-heterocycloalkenyl, —CO$_2$-heterocycloalkenyl, —S-heterocycloalkenyl, —S(O)-heterocycloalkenyl, —S(O)$_2$-heterocycloalkenyl, —N(R$^1$)-heterocycloalkenyl, —C(O)—N(R$^{21}$)-heterocycloalkenyl, and —N(R$^{21}$)—C(O)-heterocycloalkenyl, —N(R$^{21}$)—C(O)—N(R$^{21}$)-heterocycloalkenyl, —N(R$^{21}$)—S(O)-heterocycloalkenyl, —N(R$^{21}$)—S(O)$_2$-heterocycloalkenyl, —N(R$^{21}$)—S(O)$_2$—N(R$^{21}$)-heterocycloalkenyl, —S(O)—N(R$^{21}$)-heterocycloalkenyl and —S(O)$_2$—N(R$^{21}$)-heterocycloalkenyl, (6a) alkyl, —O-alkyl, —C(O)-alkyl, —CO$_2$-alkyl, —S-alkyl, —S(O)-alkyl, —S(O)$_2$-alkyl, —N(R$^1$)-alkyl, —C(O)—N(R$^{21}$)-alkyl, —N(R$^{21}$)—C(O)-alkyl, —N(R$^{21}$)—C(O)—N(R$^{21}$)-alkyl, —N(R$^{21}$)—S(O)-alkyl, —N(R$^{21}$)—S(O)$_2$-alkyl —N(R$^{21}$)—S(O)$_2$—N(R$^{21}$)-alkyl, —S(O)—N(R$^{21}$)-alkyl and —S(O)$_2$—N(R$^{21}$)-alkyl, (7a) heteroalkyl, —O-heteroalkyl, —C(O)-heteroalkyl, —CO$_2$-heteroalkyl, —S-heteroalkyl, —S(O)-heteroalkyl, —S(O)$_2$-heteroalkyl, —N(R$^1$)-heteroalkyl, —C(O)—N(R$^{21}$)-heteroalkyl, —N(R$^{21}$)—C(O)-heteroalkyl, —N(R$^{21}$)—C(O)—N(R$^{21}$)-heteroalkyl, —N(R$^{21}$)—S(O)-heteroalkyl, —N(R$^{21}$)—S(O)$_2$-heteroalkyl, —N(R$^{21}$)—S(O)$_2$—N(R$^{21}$)-heteroalkyl, —S(O)—N(R$^{21}$)-heteroalkyl and —S(O)$_2$—N(R$^{21}$)-heteroalkyl, (8a) alkenyl, —O-alkenyl, —C(O)-alkenyl, —CO$_2$-alkenyl, —S-alkenyl, —S(O)-alkenyl, —S(O)$_2$-alkenyl, —N(R$^1$)-alkenyl, —C(O)—N(R$^{21}$)-alkenyl, —N(R$^{21}$)—C(O)-alkenyl, —N(R$^{21}$)—C(O)—N(R$^{21}$)-alkenyl, —N(R$^{21}$)—S(O)-alkenyl, —N(R$^{21}$)—S(O)$_2$-alkenyl, —N(R$^{21}$)—S(O)$_2$—N(R$^{21}$)-alkenyl, —S(O)—N(R$^{21}$)-alkenyl and —S(O)$_2$—N(R$^{21}$)-alkenyl, (9a) alkynyl, —O-alkynyl, —C(O)-alkynyl, —CO$_2$-alkynyl, —S-alkynyl, —S(O)-alkynyl, —S(O)$_2$-alkynyl, —N(R$^1$)-alkynyl, —C(O)—N(R$^{21}$)-alkynyl, —N(R$^{21}$)—C(O)-alkynyl, —N(R$^{21}$)—C(O)—N(R$^{21}$)-alkynyl, —N(R$^{21}$)—S(O)-alkynyl, —N(R$^{21}$)—S(O)$_2$-alkynyl, —N(R$^{21}$)—S(O)$_2$—N(R$^{21}$)-alkynyl, —S(O)—N(R$^{21}$)-alkynyl and —S(O)$_2$—N(R$^{21}$)-alkynyl, (10a) aryl, —O-aryl, —C(O)-aryl, —CO$_2$-aryl, —S-aryl, —S(O)-aryl, —S(O)$_2$-aryl, —N(R$^1$)-aryl, —C(O)—N(R$^{21}$)-aryl, —N(R$^{21}$)—C(O)-aryl, —N(R$^{21}$)—C(O)—N(R$^{21}$)-aryl, —N(R$^{21}$)—S(O)-aryl, —N(R$^{21}$)—S(O)$_2$-aryl, —N(R$^{21}$)—S(O)$_2$—N(R$^{21}$)-aryl, —S(O)—N(R$^{21}$)-aryl and —S(O)$_2$—N(R$^{21}$)-aryl, (11a) heteroaryl, —O-heteroaryl, —C(O)-heteroaryl, —CO$_2$-heteroaryl, —S-heteroaryl, —S(O)-heteroaryl, —S(O)$_2$-heteroaryl, —N(R$^1$)-heteroaryl, —C(O)—N(R$^{21}$)-heteroaryl, —N(R$^{21}$)—C(O)-heteroaryl, —N(R$^{21}$)—C(O)—N(R$^{21}$)-heteroaryl, —N(R$^{21}$)—S(O)-heteroaryl, —N(R$^{21}$)—S(O)$_2$-heteroaryl, —N(R$^{21}$)—S(O)$_2$—N(R$^{21}$)-heteroaryl, —S(O)—N(R$^{21}$)-heteroaryl and —S(O)$_2$—N(R$^{21}$)-heteroaryl;

wherein said heteroalkyl, said heterocycloalkyl, said heterocycloalkenyl, and said heteroaryl of G may be connected through any available carbon or heteroatom, and wherein said alkyl, said heteroalkyl, said cycloalkyl, said heterocycloalkyl, said aryl, said heteroaryl, said alkenyl, said alkynyl, said cycloalkenyl, and said heterocycloalkenyl of G are unsubstituted or substituted with one or more groups independently selected from R$^2$, each R$^1$ is independently selected from:
(1b) hydrogen and —CHO,
(2b) cycloalkyl, —C(O)-cycloalkyl, —CO$_2$-cycloalkyl, —S(O)-cycloalkyl and —S(O)$_2$-cycloalkyl,
(3b) heterocycloalkyl, —C(O)-heterocycloalkyl, —CO$_2$-heterocycloalkyl, —S(O)-heterocycloalkyl and —S(O)$_2$-heterocycloalkyl,
(4b) cycloalkenyl, —C(O)-cycloalkenyl, —CO$_2$-cycloalkenyl, —S(O)-cycloalkenyl and —S(O)$_2$-cycloalkenyl,
(5b) heterocycloalkenyl, —C(O)-heterocycloalkenyl, —CO$_2$-heterocycloalkenyl, —S(O)-heterocycloalkenyl and —S(O)$_2$-heterocycloalkenyl,
(6b) alkyl, —C(O)-alkyl, —CO$_2$-alkyl, —S(O)-alkyl and —S(O)$_2$-alkyl,
(7b) heteroalkyl, —C(O)-heteroalkyl, —CO$_2$-heteroalkyl, —S(O)-heteroalkyl and —S(O)$_2$-heteroalkyl,
(8b) alkenyl, —C(O)-alkenyl, —CO$_2$-alkenyl, —S(O)-alkenyl and —S(O)$_2$-alkenyl,
(9b) alkynyl, —C(O)-alkynyl, —CO$_2$-alkynyl, —S(O)-alkynyl and —S(O)$_2$-alkynyl, (10b) aryl, —C(O)-aryl, —CO$_2$-aryl, —S(O)-aryl and —S(O)$_2$-aryl,
(11b) heteroaryl, —C(O)-heteroaryl, —CO$_2$-heteroaryl, —S(O)-heteroaryl and —S(O)$_2$-heteroaryl, wherein said heteroalkyl, said heterocycloalkyl, said heterocycloalkenyl, and said heteroaryl of R$^1$ may be connected through any available carbon or heteroatom, and wherein said alkyl, said heteroalkyl, said cycloalkyl, said heterocycloalkyl, said aryl, said heteroaryl, said alkenyl, said alkynyl, said cycloalkenyl, and said heterocycloalkenyl of R$^1$ are unsubstituted or substituted with one or more groups independently selected from R$^2$;

each R$^{21}$ is independently selected from H and C$_{1-6}$alkyl;
each R$^2$ is independently selected from:

(1c) halo, —NH$_2$, —OH, —SH, —SO$_2$H, —CO$_2$H, —SF$_5$, —OSF$_5$, cyano and —CHO,
(2c) cycloalkyl, —O-cycloalkyl, —C(O)-cycloalkyl, —CO$_2$-cycloalkyl, —S-cycloalkyl, —S(O)-cycloalkyl, —S(O)$_2$-cycloalkyl, —N(R$^6$)-cycloalkyl, —C(O)—N(R$^{21}$)-cycloalkyl, —N(R$^{21}$)—C(O)-cycloalkyl, —N(R$^{21}$)—C(O)—N(R$^{21}$)-cycloalkyl, —N(R$^{21}$)—S(O)-cycloalkyl, N(R$^{21}$)—S(O)$_2$-cycloalkyl, —N(R$^{21}$)—S(O)$_2$—N(R$^{21}$)-cycloalkyl, —S(O)—N(R$^{21}$)-cycloalkyl and —S(O)$_2$—N(R$^{21}$)-cycloalkyl,
(3c) heterocycloalkyl, —O-heterocycloalkyl, —C(O)-heterocycloalkyl, —CO$_2$-heterocycloalkyl, —S-heterocycloalkyl, —S(O)-heterocycloalkyl, —S(O)$_2$-heterocycloalkyl, —N(R$^6$)-heterocycloalkyl, —C(O)—N(R$^{21}$)-heterocycloalkyl, —N(R$^{21}$)—C(O)-heterocycloalkyl, —N(R$^{21}$)—C(O)—N(R$^{21}$)-heterocycloalkyl, —N(R$^{21}$)—S(O)-heterocycloalkyl, —N(R$^{21}$)—S(O)$_2$-heterocycloalkyl, —N(R$^{21}$)—S(O)$_2$—N(R$^{21}$)-heterocycloalkyl, —S(O)—N(R$^{21}$)-heterocycloalkyl and —S(O)$_2$—N(R$^{21}$)-heterocycloalkyl,
(4c) cycloalkenyl, —O-cycloalkenyl, —C(O)-cycloalkenyl, —CO$_2$-cycloalkenyl, —S-cycloalkenyl, —S(O)-cycloalkenyl, —S(O)$_2$-cycloalkenyl, —N(R$^6$)-cycloalkenyl, —C(O)—N(R$^{21}$)-cycloalkenyl, —N(R$^{21}$)—C(O)-cycloalkenyl, —N(R$^{21}$)—C(O)—N(R$^{21}$)-cycloalkenyl, —N(R$^{21}$)—S(O)-cycloalkenyl, —N(R$^{21}$)—S(O)$_2$-cycloalkenyl, —N(R$^{21}$)—S(O)$_2$—N(R$^{21}$)-cycloalkenyl, —S(O)—N(R$^{21}$)-cycloalkenyl and —S(O)$_2$—N(R$^{21}$)-cycloalkenyl,
(5c) heterocycloalkenyl, —O-heterocycloalkenyl, —C(O)-heterocycloalkenyl, —CO$_2$-heterocycloalkenyl, —S-heterocycloalkenyl, —S(O)-heterocycloalkenyl, —S(O)$_2$-heterocycloalkenyl, —N(R$^6$)-heterocycloalkenyl, —C(O)—N(R$^{21}$)-heterocycloalkenyl, and —N(R$^{21}$)—C(O)-heterocycloalkenyl, —N(R$^{21}$)—C(O)—N(R$^{21}$)-heterocycloalkenyl, —N(R$^{21}$)—S(O)-heterocycloalkenyl, —N(R$^{21}$)—S(O)$_2$-heterocycloalkenyl, —N(R$^{21}$)—S(O)$_2$—N(R$^{21}$)-heterocycloalkenyl, —S(O)—N(R$^{21}$)-heterocycloalkenyl and —S(O)$_2$—N(R$^{21}$)-heterocycloalkenyl,
(6c) alkyl, —O-alkyl, —C(O)-alkyl, —CO$_2$-alkyl, —S-alkyl, —S(O)-alkyl, —S(O)$_2$-alkyl, —N(R$^6$)-alkyl, —C(O)—N(R$^{21}$)-alkyl, —N(R$^{21}$)—C(O)-alkyl, —N(R$^{21}$)—C(O)—N(R$^{21}$)-alkyl, —N(R$^{21}$)—S(O)-alkyl, —N(R$^{21}$)—S(O)$_2$-alkyl, —N(R$^{21}$)—S(O)$_2$—N(R$^{21}$)-alkyl, —S(O)—N(R$^{21}$)-alkyl and —S(O)$_2$—N(R$^{21}$)-alkyl,
(7c) heteroalkyl, —O-heteroalkyl, —C(O)-heteroalkyl, —CO$_2$-heteroalkyl, —S-heteroalkyl, —S(O)-heteroalkyl, —S(O)$_2$-heteroalkyl, —N(R$^6$)-heteroalkyl, —C(O)—N(R$^{21}$)-heteroalkyl, —N(R$^{21}$)—C(O)-heteroalkyl, —N(R$^{21}$)—C(O)—N(R$^{21}$)-heteroalkyl, —N(R$^{21}$)—S(O)-heteroalkyl, —N(R$^{21}$)—S(O)$_2$-heteroalkyl, —N(R$^{21}$)—S(O)$_2$—N(R$^{21}$)-heteroalkyl, —S(O)—N(R$^{21}$)-heteroalkyl and —S(O)$_2$—N(R$^{21}$)-heteroalkyl,
(8c) alkenyl, —O-alkenyl, —C(O)-alkenyl, —CO$_2$-alkenyl, —S-alkenyl, —S(O)-alkenyl, —S(O)$_2$-alkenyl, —N(R$^6$)-alkenyl, —C(O)—N(R$^{21}$)-alkenyl, —N(R$^{21}$)—C(O)-alkenyl, —N(R$^{21}$)—C(O)—N(R$^{21}$)-alkenyl, —N(R$^{21}$)—S(O)-alkenyl, —N(R$^{21}$)—S(O)$_2$-alkenyl, —N(R$^{21}$)—S(O)$_2$—N(R$^{21}$)-alkenyl, —S(O)—N(R$^{21}$)-alkenyl and —S(O)$_2$—N(R$^{21}$)-alkenyl,
(9c) alkynyl, —O-alkynyl, —C(O)-alkynyl, —CO$_2$-alkynyl, —S-alkynyl, —S(O)-alkynyl, —S(O)$_2$-alkynyl, —N(R$^6$)-alkynyl, —C(O)—N(R$^{21}$)-alkynyl, —N(R$^{21}$)—C(O)-alkynyl, —N(R$^{21}$)—C(O)—N(R$^{21}$)-alkynyl, —N(R$^{21}$)—S(O)-alkynyl, —N(R$^{21}$)—S(O)$_2$-alkynyl, —N(R$^{21}$)—S(O)$_2$—N(R$^{21}$)-alkynyl, —S(O)—N(R$^{21}$)-alkynyl and —S(O)$_2$—N(R$^{21}$)-alkynyl, (10c) aryl, —O-aryl, —C(O)-aryl, —CO$_2$-aryl, —S-aryl, —S(O)-aryl, —S(O)$_2$-aryl, —N(R$^6$)-aryl, —C(O)—N(R$^{21}$)-aryl, —N(R$^{21}$)—C(O)-aryl, —N(R$^{21}$)—C(O)—N(R$^{21}$)-aryl, —N(R$^{21}$)—S(O)-aryl, —N(R$^{21}$)—S(O)$_2$-aryl, —N(R$^{21}$)—S(O)$_2$—N(R$^{21}$)-aryl, —S(O)—N(R$^{21}$)-aryl and —S(O)$_2$—N(R$^{21}$)-aryl, (11c) heteroaryl, —O-heteroaryl, —C(O)-heteroaryl, —CO$_2$-heteroaryl, —S-heteroaryl, —S(O)-heteroaryl, —S(O)$_2$-heteroaryl, —N(R$^6$)-heteroaryl, —C(O)—N(R$^{21}$)-heteroaryl, —N(R$^{21}$)—C(O)-heteroaryl, —N(R$^{21}$)—C(O)—N(R$^{21}$)-heteroaryl, —N(R$^{21}$)—S(O)-heteroaryl, —N(R$^{21}$)—S(O)$_2$-heteroaryl, —N(R$^{21}$)—S(O)$_2$—N(R$^{21}$)-heteroaryl, —S(O)—N(R$^{21}$)-heteroaryl and —S(O)$_2$—N(R$^{21}$)-heteroaryl, wherein said heteroalkyl, said heterocycloalkyl, said heterocycloalkenyl, and said heteroaryl of R$^2$ may be connected through any available carbon or heteroatom, and wherein said alkyl, said heteroalkyl, said cycloalkyl, said heterocycloalkyl, said aryl, said heteroaryl, said alkenyl, said alkynyl, said cycloalkenyl, and said heterocycloalkenyl of R$^2$ are unsubstituted or substituted with one or more groups independently selected from R$^7$, R$^3$ is selected from H and lower alkyl;

Z is a moiety selected from —(C(R$^{11}$)$_2$)—(C(R$^{12}$R$^{13}$))$_m$—C(O)OH, —(C(R$^{11}$)$_2$)—(C(R$^{14}$)$_2$)$_n$—C(O)OH, —(C(R$^{11}$)$_2$)—(C(R$^{12}$R$^{13}$))$_m$—C(O)Oalkyl, —(C(R$^{11}$)$_2$)—(C(R$^{14}$)$_2$)$_n$—C(O)Oalkyl,

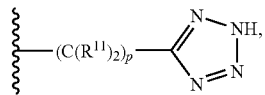

—(C(R$^{11}$)$_2$)—(C(R$^{12}$R$^{13}$))$_m$-Q, and —(C(R$^{11}$)$_2$)—(C(R$^{14}$)$_2$)$_n$-Q, wherein Q is a moiety selected from the group consisting of:

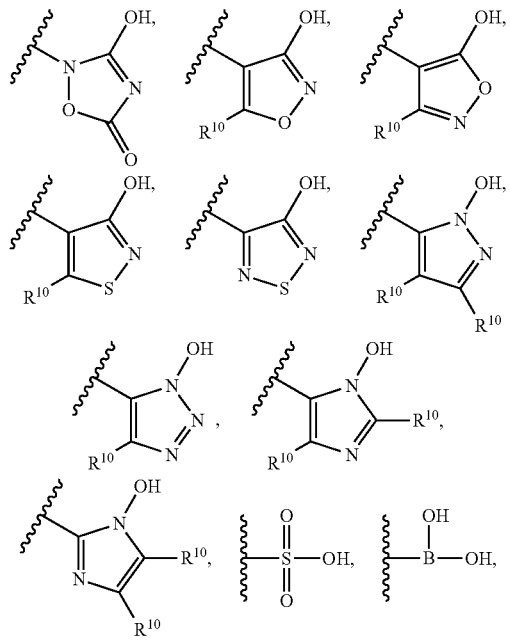

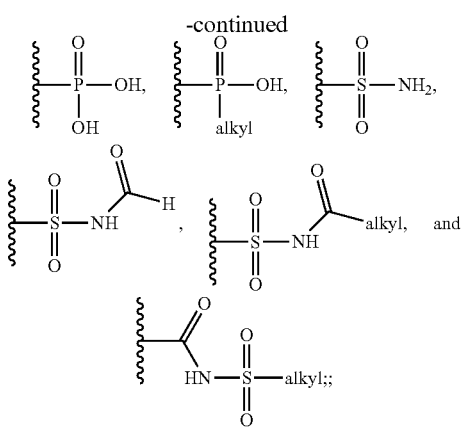

wherein each R$^{10}$ is independently H or alkyl;
m is an integer from 0 to 5;
n is an integer from 0 to 5;
p is an integer from 0 to 5;

each R$^4$ is independently selected from H, —OH, lower alkyl, haloalkyl, alkoxy, heteroalkyl, cyano-substituted lower alkyl, hydroxy-substituted lower alkyl, cycloalkyl, —O-cycloalkyl, —O-alkyl-cycloalkyl, and heterocycloalkyl, —O-heterocycloalkyl, and —O-alkyl-heterocycloalkyl;

each R$^{5A}$ is independently selected from H, alkyl, haloalkyl, heteroalkyl, cyano-substituted alkyl, hydroxy-substituted alkyl, cycloalkyl, -alkyl-cycloalkyl, and heterocycloalkyl, -alkyl-heterocycloalkyl, or, alternatively, two R$^{5A}$ groups are taken together with the carbon atom to which they are attached to form a carbonyl group, a spirocycloalkyl group, a spiroheterocycloalkyl group, an oxime group, or a substituted oxime group, said oxime substituents being independently selected from alkyl, haloalkyl, hydroxyl-substituted alkyl, and cycloalkyl;

each R$^5$ is independently selected from H, —OH, alkyl, haloalkyl, alkoxy, heteroalkyl, cyano-substituted alkyl, hydroxy-substituted alkyl, cycloalkyl, -alkyl-cycloalkyl, —O-cycloalkyl, —O-alkyl-cycloalkyl, and heterocycloalkyl, -alkyl-heterocycloalkyl, —O-heterocycloalkyl, and —O-alkyl-heterocycloalkyl, or, alternatively, two R$^5$ groups bound to the same carbon atom are taken together with the carbon atom to which they are attached to form a carbonyl group, a spirocycloalkyl group, a spiroheterocycloalkyl group, an oxime group, or a substituted oxime group, said oxime substituents being independently selected from alkyl, haloalkyl, hydroxyl-substituted alkyl, and cycloalkyl;

each R$^6$ is independently selected from:
(1d) hydrogen, —CHO,
(2d) cycloalkyl, —C(O)-cycloalkyl, —CO$_2$-cycloalkyl, —S(O)-cycloalkyl, —S(O)$_2$-cycloalkyl,
(3d) heterocycloalkyl, —C(O)-heterocycloalkyl, —CO$_2$-heterocycloalkyl, —S(O)-heterocycloalkyl, —S(O)$_2$-heterocycloalkyl,
(4d) cycloalkenyl, —C(O)-cycloalkenyl, —CO$_2$-cycloalkenyl, —S(O)-cycloalkenyl, —S(O)$_2$-cycloalkenyl,
(5d) heterocycloalkenyl, —C(O)-heterocycloalkenyl, —CO$_2$-heterocycloalkenyl, —S(O)-heterocycloalkenyl, —S(O)$_2$-heterocycloalkenyl,
(6d) alkyl, —C(O)-alkyl, —CO$_2$-alkyl, —S(O)-alkyl, —S(O)$_2$-alkyl,
(7d) heteroalkyl, —C(O)-heteroalkyl, —CO$_2$-heteroalkyl, —S(O)-heteroalkyl, —S(O)$_2$-heteroalkyl, (8d) alkenyl, —C(O)-alkenyl, —CO₂-alkenyl, —S(O)-alkenyl, —S(O)₂-alkenyl, (9d) alkynyl, —C(O)-alkynyl, —CO₂-alkynyl, —S(O)-alkynyl, —S(O)₂-alkynyl, (10d) aryl, —C(O)-aryl, —CO₂-aryl, —S(O)-aryl, —S(O)₂-aryl, (11d) heteroaryl, —C(O)-heteroaryl, —CO₂-heteroaryl, —S(O)-heteroaryl, —S(O)₂-heteroaryl, each $R^7$ is independently selected from:

(1e) halo, —NH₂, —OH, —SH, —SO₂H, CO₂H, —SF₅, —OSF₅, cyano and —CHO, (2e) cycloalkyl, —O-cycloalkyl, —C(O)-cycloalkyl, —CO₂-cycloalkyl, —S-cycloalkyl, —S(O)-cycloalkyl, —S(O)₂-cycloalkyl, —N(R⁶)-cycloalkyl, —C(O)—N(R²¹)-cycloalkyl, —N(R²¹)—C(O)-cycloalkyl, —N(R²¹)—C(O)—N(R²¹)-cycloalkyl, —N(R²¹)—S(O)-cycloalkyl, —N(R²¹)—S(O)₂-cycloalkyl, —N(R²¹)—S(O)₂—N(R²¹)-cycloalkyl, —S(O)—N(R²¹)-cycloalkyl and —S(O)₂—N(R²¹)-cycloalkyl, (3e) heterocycloalkyl, —O-heterocycloalkyl, —C(O)-heterocycloalkyl, —CO₂-heterocycloalkyl, —S-heterocycloalkyl, —S(O)-heterocycloalkyl, —S(O)₂-heterocycloalkyl, —N(R⁶)-heterocycloalkyl, —C(O)—N(R²¹)-heterocycloalkyl, —N(R²¹)—C(O)-heterocycloalkyl, —N(R²¹)—C(O)—N(R²¹)-heterocycloalkyl, —N(R²¹)—S(O)-heterocycloalkyl, —N(R²¹)—S(O)₂-heterocycloalkyl, —N(R²¹)—S(O)₂—N(R²¹)-heterocycloalkyl, —S(O)—N(R²¹)-heterocycloalkyl and —S(O)₂—N(R²¹)-heterocycloalkyl, (4e) cycloalkenyl, —O-cycloalkenyl, —C(O)-cycloalkenyl, —CO₂-cycloalkenyl, —S-cycloalkenyl, —S(O)-cycloalkenyl, —S(O)₂-cycloalkenyl, —N(R⁶)-cycloalkenyl, —C(O)—N(R²¹)-cycloalkenyl, —N(R²¹)—C(O)-cycloalkenyl, —N(R²¹)—C(O)—N(R²¹)-cycloalkenyl, —N(R²¹)—S(O)-cycloalkenyl, —N(R²¹)—S(O)₂-cycloalkenyl, —N(R²¹)—S(O)₂—N(R²¹)-cycloalkenyl, —S(O)—N(R²¹)-cycloalkenyl and —S(O)₂—N(R²¹)-cycloalkenyl, (5e) heterocycloalkenyl, —O-heterocycloalkenyl, —C(O)-heterocycloalkenyl, —CO₂-heterocycloalkenyl, —S-heterocycloalkenyl, —S(O)-heterocycloalkenyl, —S(O)₂-heterocycloalkenyl, —N(R⁶)-heterocycloalkenyl, —C(O)—N(R²¹)-heterocycloalkenyl, —N(R²¹)—C(O)-heterocycloalkenyl, —N(R²¹)—C(O)—N(R²¹)-heterocycloalkenyl, —N(R²¹)—S(O)-heterocycloalkenyl, —N(R²¹)—S(O)₂-heterocycloalkenyl, —N(R²¹)—S(O)₂—N(R²¹)-heterocycloalkenyl, —S(O)—N(R²¹)-heterocycloalkenyl and —S(O)₂—N(R²¹)-heterocycloalkenyl, (6e) alkyl, —O-alkyl, —C(O)-alkyl, —CO₂-alkyl, —S-alkyl, —S(O)-alkyl, —S(O)₂-alkyl, —N(R⁶)-alkyl, —C(O)—N(R²¹)-alkyl, —N(R²¹)—C(O)-alkyl, —N(R²¹)—C(O)—N(R²¹)-alkyl, —N(R²¹)—S(O)-alkyl, —N(R²¹)—S(O)₂-alkyl, —N(R²¹)—S(O)₂—N(R²¹)-alkyl, —S(O)—N(R²¹)-alkyl and —S(O)₂—N(R²¹)-alkyl, (7e) heteroalkyl, —O-heteroalkyl, —C(O)-heteroalkyl, —CO₂-heteroalkyl, —S-heteroalkyl, —S(O)-heteroalkyl, —S(O)₂-heteroalkyl, —N(R⁶)-heteroalkyl, —C(O)—N(R²¹)-heteroalkyl, —N(R²¹)—C(O)-heteroalkyl, —N(R²¹)—C(O)—N(R²¹)-heteroalkyl, —N(R²¹)—S(O)-heteroalkyl, —N(R²¹)—S(O)₂-heteroalkyl, —N(R²¹)—S(O)₂—N(R²¹)-heteroalkyl, —S(O)—N(R²¹)-heteroalkyl and —S(O)₂—N(R²¹)-heteroalkyl, (8e) alkenyl, —O-alkenyl, —C(O)-alkenyl, —CO₂-alkenyl, —S-alkenyl, —S(O)-alkenyl, —S(O)₂-alkenyl, —N(R⁶)-alkenyl, —C(O)—N(R²¹)-alkenyl, —N(R²¹)—C(O)-alkenyl, —N(R²¹)—C(O)—N(R²¹)-alkenyl, —N(R²¹)—S(O)-alkenyl, —N(R²¹)—S(O)₂-alkenyl, —N(R²¹)—S(O)₂—N(R²¹)-alkenyl, —S(O)—N(R²¹)-alkenyl and —S(O)₂—N(R²¹)-alkenyl, (9e) alkynyl, —O-alkynyl, —C(O)-alkynyl, —CO₂-alkynyl, —S-alkynyl, —S(O)-alkynyl, —S(O)₂-alkynyl, —N(R⁶)-alkynyl, —C(O)—N(R⁶)-alkynyl, —N(R²¹)—C(O)-alkynyl, —N(R²¹)—C(O)—N(R²¹)-alkynyl, —N(R²¹)—S(O)-alkynyl, —N(R²¹)—S(O)₂-alkynyl, —N(R²¹)—S(O)₂—N(R²¹)-alkynyl, —S(O)—N(R²¹)-alkynyl and —S(O)₂—N(R²¹)-alkynyl, (10e) aryl, —O-aryl, —C(O)-aryl, —CO₂-aryl, —S-aryl, —S(O)-aryl, —S(O)₂-aryl, —N(R⁶)-aryl, —C(O)—N(R²¹)-aryl, —N(R²¹)—C(O)-aryl, —N(R²¹)—C(O)—N(R²¹)-aryl, —N(R²¹)—S(O)-aryl, —N(R²¹)—S(O)₂-aryl, —N(R²¹)—S(O)₂—N(R²¹)-aryl, —S(O)—N(R²¹)-aryl, —S(O)₂—N(R²¹)-aryl, (11e) heteroaryl, —O-heteroaryl, —C(O)-heteroaryl, —CO₂-heteroaryl, —S-heteroaryl, —S(O)-heteroaryl, —S(O)₂-heteroaryl, —N(R⁶)-heteroaryl, —C(O)—N(R²¹)-heteroaryl, —N(R²¹)—C(O)-heteroaryl, —N(R²¹)—C(O)—N(R²¹)-heteroaryl, —N(R²¹)—S(O)-heteroaryl, —N(R²¹)—S(O)₂-heteroaryl, —N(R²¹)—S(O)₂—N(R²¹)-heteroaryl, —S(O)—N(R²¹)-heteroaryl, —S(O)₂—N(R²¹)-heteroaryl, wherein said heteroalkyl, said heterocycloalkyl, said heterocycloalkenyl, and said heteroaryl of $R^7$ may be connected through any available carbon or heteroatom, each $R^{11}$ is independently selected from H and lower alkyl;

each $R^{12}$ is independently selected from H, lower alkyl, —OH, hydroxy-substituted lower alkyl;

each $R^{13}$ is independently selected from H, unsubstituted lower alkyl, lower alkyl substituted with one or more groups each independently selected from hydroxyl and alkoxy, or $R^{12}$ and $R^{13}$ are taken together to form an oxo; and each $R^{14}$ is independently selected from H and fluoro.

In one embodiment of the invention, each V is independently selected from the group consisting of: alkyl, heteroalkyl, cycloalkyl, heterocycloalkyl, cycloalkenyl, aryl, and heteroaryl, wherein said heterocycloalkyl and heteroaryl are connected through a carbon atom, and wherein said alkyl, alkenyl, cycloalkyl, heterocycloalkyl, cycloalkenyl, aryl, and heteroaryl of V are unsubstituted or substituted with one or more groups independently selected from:

(1) halo, —NH₂, —OH, —SH, —SO₂H, CO₂H, —SF₅, —OSF₅, cyano, —CHO;

(2) cycloalkyl, —O-cycloalkyl, —C(O)-cycloalkyl, —CO₂-cycloalkyl, —S-cycloalkyl, —S(O)-cycloalkyl, —S(O)₂-cycloalkyl, —N(R¹)-cycloalkyl, —C(O)—N(R²¹)-cycloalkyl, —N(R²¹)—C(O)-cycloalkyl, —N(R²¹)—C(O)—N(R²¹)-cycloalkyl, —N(R²¹)—S(O)-cycloalkyl, —N(R²¹)—S(O)₂-cycloalkyl, —N(R²¹)—S(O)₂—N(R²¹)-cycloalkyl, —S(O)—N(R²¹)-cycloalkyl and —S(O)₂—N(R²¹)-cycloalkyl;

(3) heterocycloalkyl, —O-heterocycloalkyl, —C(O)-heterocycloalkyl, —CO₂-heterocycloalkyl, —S-heterocycloalkyl, —S(O)-heterocycloalkyl, —S(O)₂-heterocycloalkyl, —N(R¹)-heterocycloalkyl, —C(O)—N(R²¹)-heterocycloalkyl, —N(R²¹)—C(O)-heterocycloalkyl, —N(R²¹)—C(O)—N(R²¹)-heterocycloalkyl, —N(R²¹)—S(O)-heterocycloalkyl, —N(R²¹)—S(O)₂-heterocycloalkyl, —N(R²¹)—S(O)₂—N(R²¹)-heterocycloalkyl, —S(O)—N(R²¹)-heterocycloalkyl and —S(O)₂—N(R²¹)-heterocycloalkyl;

(4) cycloalkenyl, —O-cycloalkenyl, —C(O)-cycloalkenyl, —CO₂-cycloalkenyl, —S-cycloalkenyl, —S(O)-cycloalkenyl, —S(O)₂-cycloalkenyl, —N(R¹)-cycloalkenyl, —C(O)—N(R²¹)-cycloalkenyl, —N(R²¹)—C(O)-cycloalkenyl, —N(R²¹)—C(O)—N(R²¹)-cycloalkenyl, —N(R²¹)—

S(O)-cycloalkenyl, —N(R²¹)—S(O)₂-cycloalkenyl, —N(R²¹)—S(O)₂—N(R²¹)— cycloalkenyl, —S(O)—N(R²¹)-cycloalkenyl and —S(O)₂—N(R²¹)-cycloalkenyl;

(5) heterocycloalkenyl, —O-heterocycloalkenyl, —C(O)-heterocycloalkenyl, —CO₂-heterocycloalkenyl, —S-heterocycloalkenyl, —S(O)-heterocycloalkenyl, —S(O)₂-heterocycloalkenyl, —N(R¹)-heterocycloalkenyl, —C(O)—N(R²¹)-heterocycloalkenyl, and —N(R²¹)—C(O)-heterocycloalkenyl, —N(R²¹)—C(O)—N(R²¹)-heterocycloalkenyl, —N(R²¹)—S(O)-heterocycloalkenyl, —N(R²¹)—S(O)₂-heterocycloalkenyl, —N(R²¹)—S(O)₂—N(R²¹)-heterocycloalkenyl, —S(O)—N(R²¹)-heterocycloalkenyl and —S(O)₂—N(R²¹)-heterocycloalkenyl;

(6) alkyl, —O-alkyl, —C(O)-alkyl, —CO₂-alkyl, —S-alkyl, —S(O)-alkyl, —S(O)₂-alkyl, —N(R¹)-alkyl, —C(O)—N(R²¹)-alkyl, —N(R²¹)—C(O)-alkyl, —N(R²¹)—C(O)—N(R²¹)-alkyl, —N(R²¹)—S(O)-alkyl, —N(R²¹)—S(O)₂-alkyl, —N(R²¹)—S(O)₂—N(R²¹)-alkyl, —S(O)—N(R²¹)-alkyl and —S(O)₂—N(R²¹)-alkyl;

(7) heteroalkyl, —O-heteroalkyl, —C(O)-heteroalkyl, —CO₂-heteroalkyl, —S-heteroalkyl, —S(O)-heteroalkyl, —S(O)₂-heteroalkyl, —N(R¹)-heteroalkyl, —C(O)—N(R²¹)-heteroalkyl, —N(R²¹)—C(O)-heteroalkyl, —N(R²¹)—C(O)—N(R²¹)-heteroalkyl, —N(R²¹)—S(O)-heteroalkyl, —N(R²¹)—S(O)₂-heteroalkyl, —N(R²¹)—S(O)₂—N(R²¹)-heteroalkyl, —S(O)—N(R²¹)-heteroalkyl and —S(O)₂—N(R²¹)-heteroalkyl;

(8) alkenyl, —O-alkenyl, —C(O)-alkenyl, —CO₂-alkenyl, —S-alkenyl, —S(O)-alkenyl, —S(O)₂-alkenyl, —N(R¹)-alkenyl, —C(O)—N(R²¹)-alkenyl, —N(R²¹)—C(O)-alkenyl, —N(R²¹)—C(O)—N(R²¹)-alkenyl, —N(R²¹)—S(O)-alkenyl, —N(R²¹)—S(O)₂-alkenyl, —N(R²¹)—S(O)₂—N(R²¹)-alkenyl, —S(O)—N(R²¹)-alkenyl and —S(O)₂—N(R²¹)-alkenyl;

(9) alkynyl, —O-alkynyl, —C(O)-alkynyl, —CO₂-alkynyl, —S-alkynyl, —S(O)-alkynyl, —S(O)₂-alkynyl, —N(R¹)-alkynyl, —C(O)—N(R²¹)-alkynyl, —N(R²¹)—C(O)-alkynyl, —N(R²¹)—C(O)—N(R²¹)-alkynyl, —N(R²¹)—S(O)-alkynyl, —N(R²¹)—S(O)₂-alkynyl, —N(R²¹)—S(O)₂—N(R²¹)-alkynyl, —S(O)—N(R²¹)-alkynyl and —S(O)₂—N(R²¹)-alkynyl;

(10) aryl, —O-aryl, —C(O)-aryl, —CO₂-aryl, —S-aryl, —S(O)-aryl, —S(O)₂-aryl, —N(R¹)-aryl, —C(O)—N(R²¹)-aryl, —N(R²¹)—C(O)-aryl, —N(R²¹)—C(O)—N(R²¹)-aryl, —N(R²¹)—S(O)-aryl, —N(R²¹)—S(O)₂-aryl, —N(R²¹)—S(O)₂—N(R²¹)-aryl, —S(O)—N(R²¹)-aryl and —S(O)₂—N(R²¹)-aryl;

(11) heteroaryl, —O-heteroaryl, —C(O)-heteroaryl, —CO₂-heteroaryl, —S-heteroaryl, —S(O)-heteroaryl, —S(O)₂-heteroaryl, —N(R¹)-heteroaryl, —C(O)—N(R²¹)-heteroaryl, —N(R²¹)—C(O)-heteroaryl, —N(R²¹)—C(O)—N(R²¹)-heteroaryl, —N(R²¹)—S(O)-heteroaryl, —N(R²¹)—S(O)₂-heteroaryl, —N(R²¹)—S(O)₂—N(R²¹)-heteroaryl, —S(O)—N(R²¹)-heteroaryl and —S(O)₂—N(R²¹)-heteroaryl;

wherein said heteroalkyl of (7), heterocycloalkyl of (3), heterocycloalkenyl of (5), and heteroaryl of (11) are connected through any available carbon atom or heteroatom, and wherein said alkyl, heteroalkyl, cycloalkyl, heterocycloalkyl, aryl, heteroaryl, alkenyl, alkynyl, cycloalkenyl, and heterocycloalkenyl of (1) through (11) are unsubstituted or substituted with one or more groups independently selected from R².

In another embodiment of the invention, each V is independently selected from the group consisting of: alkyl, heteroalkyl, cycloalkyl, heterocycloalkyl, aryl, and heteroaryl, wherein said heterocycloalkyl, and heteroaryl of V are connected through a carbon atom, and wherein said alkyl, cycloalkyl, heterocycloalkyl, aryl, and heteroaryl of V are unsubstituted or substituted with one or more groups independently selected from:

(1) halo, —NH₂, —OH, —SH, —SO₂H, CO₂H, —SF₅, —OSF₅, cyano and —CHO;

(2) cycloalkyl, —O-cycloalkyl, —C(O)-cycloalkyl, —CO₂-cycloalkyl, —S-cycloalkyl, —S(O)-cycloalkyl, —S(O)₂-cycloalkyl, —N(R¹)-cycloalkyl, —C(O)—N(R²¹)-cycloalkyl, —N(R²¹)—C(O)-cycloalkyl, —N(R²¹)—C(O)—N(R²¹)-cycloalkyl, —N(R²¹)—S(O)-cycloalkyl, —N(R²¹)—S(O)₂-cycloalkyl, —N(R²¹)—S(O)₂—N(R²¹)-cycloalkyl, —S(O)—N(R²¹)-cycloalkyl and —S(O)₂—N(R²¹)-cycloalkyl;

(3) heterocycloalkyl, —O-heterocycloalkyl, —C(O)-heterocycloalkyl, —CO₂-heterocycloalkyl, —S-heterocycloalkyl, —S(O)-heterocycloalkyl, —S(O)₂-heterocycloalkyl, —N(R¹)-heterocycloalkyl, —C(O)—N(R²¹)-heterocycloalkyl, —N(R²¹)—C(O)-heterocycloalkyl, —N(R²¹)—C(O)—N(R²¹)-heterocycloalkyl, —N(R²¹)—S(O)-heterocycloalkyl, —N(R²¹)—S(O)₂-heterocycloalkyl, —N(R²¹)—S(O)₂—N(R²¹)-heterocycloalkyl, —S(O)—N(R²¹)-heterocycloalkyl and —S(O)₂—N(R²¹)-heterocycloalkyl;

(4) cycloalkenyl, —O-cycloalkenyl, —C(O)-cycloalkenyl, —CO₂-cycloalkenyl, —S-cycloalkenyl, —S(O)-cycloalkenyl, —S(O)₂-cycloalkenyl, —N(R¹)-cycloalkenyl, —C(O)—N(R²¹)-cycloalkenyl, —N(R²¹)—C(O)-cycloalkenyl, —N(R²¹)—C(O)—N(R²¹)-cycloalkenyl, —N(R²¹)—S(O)-cycloalkenyl, —N(R²¹)—S(O)₂-cycloalkenyl, —N(R²¹)—S(O)₂—N(R²¹)-cycloalkenyl, —S(O)—N(R²¹)-cycloalkenyl and —S(O)₂—N(R²¹)-cycloalkenyl;

(5) heterocycloalkenyl, —O-heterocycloalkenyl, —C(O)-heterocycloalkenyl, —CO₂-heterocycloalkenyl, —S-heterocycloalkenyl, —S(O)-heterocycloalkenyl, —S(O)₂-heterocycloalkenyl, —N(R¹)-heterocycloalkenyl, —C(O)—N(R²¹)-heterocycloalkenyl, —N(R²¹)—C(O)-heterocycloalkenyl, —N(R²¹)—C(O)—N(R²¹)-heterocycloalkenyl, —N(R²¹)—S(O)-heterocycloalkenyl, —N(R²¹)—S(O)₂-heterocycloalkenyl, —N(R²¹)—S(O)₂—N(R²¹)-heterocycloalkenyl, —S(O)—N(R²¹)-heterocycloalkenyl and —S(O)₂—N(R²¹)-heterocycloalkenyl;

(6) alkyl, —O-alkyl, —C(O)-alkyl, —CO₂-alkyl, —S-alkyl, —S(O)-alkyl, —S(O)₂-alkyl, —N(R¹)-alkyl, —C(O)—N(R²¹)-alkyl, —N(R²¹)—C(O)-alkyl, —N(R²¹)—C(O)—N(R²¹)-alkyl, —N(R²¹)—S(O)-alkyl, —N(R²¹)—S(O)₂-alkyl, —N(R²¹)—S(O)₂—N(R²¹)-alkyl, —S(O)—N(R²¹)-alkyl and —S(O)₂—N(R²¹)-alkyl;

(7) heteroalkyl, —O-heteroalkyl, —C(O)-heteroalkyl, —CO₂-heteroalkyl, —S-heteroalkyl, —S(O)-heteroalkyl, —S(O)₂-heteroalkyl, —N(R¹)-heteroalkyl, —C(O)—N(R²¹)-heteroalkyl, —N(R²¹)—C(O)-heteroalkyl, —N(R²¹)—C(O)—N(R²¹)-heteroalkyl, —N(R²¹)—S(O)-heteroalkyl, —N(R²¹)—S(O)₂-heteroalkyl, —N(R²¹)—S(O)₂—N(R²¹)-heteroalkyl, —S(O)—N(R²¹)-heteroalkyl and —S(O)₂—N(R²¹)-heteroalkyl;

(8) alkenyl, —O-alkenyl, —C(O)-alkenyl, —CO₂-alkenyl, —S-alkenyl, —S(O)-alkenyl, —S(O)₂-alkenyl, —N(R¹)-alkenyl, —C(O)—N(R²¹)-alkenyl, —N(R²¹)—C(O)-alkenyl, —N(R²¹)—C(O)—N(R²¹)-alkenyl, —N(R²¹)—S(O)-alkenyl, —N(R²¹)—S(O)₂-alkenyl, —N(R²¹)—S(O)₂—N(R²¹)-alkenyl, —S(O)—N(R²¹)-alkenyl and —S(O)₂—N(R²¹)-alkenyl;

(9) alkynyl, —O-alkynyl, —C(O)-alkynyl, —CO₂-alkynyl, —S-alkynyl, —S(O)-alkynyl, —S(O)₂-alkynyl, —N(R¹)-alkynyl, —C(O)—N(R²¹)-alkynyl, —N(R²¹)—C (O)-alkynyl, —N($R^{21}$)—C(O)—N($R^{21}$)-alkynyl, —N($R^{21}$)—S(O)-alkynyl, —N($R^{21}$)—S(O)$_2$-alkynyl, —N($R^{21}$)—S(O)$_2$—N($R^{21}$)-alkynyl, —S(O)—N($R^{21}$)-alkynyl, and —S(O)$_2$—N($R^{21}$)-alkynyl;

(10) aryl, —O-aryl, —C(O)-aryl, —CO$_2$-aryl, —S-aryl, —S(O)-aryl, —S(O)$_2$-aryl, —N($R^1$)-aryl, —C(O)—N($R^{21}$)-aryl, —N($R^{21}$)—C(O)-aryl, —N($R^{21}$)—C(O)—N($R^{21}$)-aryl, —N($R^{21}$)—S(O)-aryl, —N($R^{21}$)—S(O)$_2$-aryl, —N($R^{21}$)—S(O)$_2$—N($R^{21}$)-aryl, —S(O)—N($R^{21}$)-aryl and —S(O)$_2$—N($R^{21}$)-aryl;

(11) heteroaryl, —O-heteroaryl, —C(O)-heteroaryl, —CO$_2$-heteroaryl, —S-heteroaryl, —S(O)-heteroaryl, —S(O)$_2$-heteroaryl, —N($R^1$)-heteroaryl, —C(O)—N($R^{21}$)-heteroaryl, —N($R^{21}$)—C(O)-heteroaryl, —N($R^{21}$)—C(O)—N($R^{21}$)-heteroaryl, —N($R^{21}$)—S(O)-heteroaryl, —N($R^{21}$)—S(O)$_2$-heteroaryl, —N($R^{21}$)—S(O)$_2$—N($R^{21}$)-heteroaryl, —S(O)—N($R^{21}$)-heteroaryl and —S(O)$_2$—N($R^{21}$)-heteroaryl;

wherein said heteroalkyl of (7), heterocycloalkyl of (3), heterocycloalkenyl of (5), and said heteroaryl of (11) are connected through any available carbon or heteroatom, and wherein said alkyl, heteroalkyl, cycloalkyl, heterocycloalkyl, aryl, heteroaryl, alkenyl, alkynyl, cycloalkenyl, and heterocycloalkenyl of (1) through (11) are unsubstituted or substituted with one or more groups independently selected from $R^2$.

In another embodiment of the invention, each V is independently selected from the group consisting of: alkyl and cycloalkyl, each being unsubstituted or substituted with one to three groups independently selected from:

(1) halo, —NH$_2$, —OH, —SH, —SO$_2$H, CO$_2$H, —SF$_5$, —OSF$_5$, cyano and —CHO;

(2) cycloalkyl, —O-cycloalkyl, —C(O)-cycloalkyl, —CO$_2$-cycloalkyl, —S-cycloalkyl, —S(O)-cycloalkyl, —S(O)$_2$-cycloalkyl, —N($R^1$)-cycloalkyl, —C(O)—N($R^{21}$)-cycloalkyl, —N($R^{21}$)—C(O)-cycloalkyl, —N($R^{21}$)—C(O)—N($R^{21}$)-cycloalkyl, —N($R^{21}$)—S(O)-cycloalkyl, —N($R^{21}$)—S(O)$_2$-cycloalkyl, —N($R^{21}$)—S(O)$_2$—N($R^{21}$)-cycloalkyl, —S(O)—N($R^{21}$)-cycloalkyl and —S(O)$_2$—N($R^{21}$)-cycloalkyl;

(3) heterocycloalkyl, —O-heterocycloalkyl, —C(O)-heterocycloalkyl, —CO$_2$-heterocycloalkyl, —S-heterocycloalkyl, —S(O)-heterocycloalkyl, —S(O)$_2$-heterocycloalkyl, —N($R^1$)-heterocycloalkyl, —C(O)—N($R^{21}$)-heterocycloalkyl, —N($R^{21}$)—C(O)-heterocycloalkyl, —N($R^{21}$)—C(O)—N($R^{21}$)-heterocycloalkyl, —N($R^{21}$)—S(O)-heterocycloalkyl, —N($R^{21}$)—S(O)$_2$-heterocycloalkyl, —N($R^{21}$)—S(O)$_2$—N($R^{21}$)-heterocycloalkyl, —S(O)—N($R^{21}$)-heterocycloalkyl and —S(O)$_2$—N($R^{21}$)-heterocycloalkyl;

(4) cycloakenyl, —O-cycloalkenyl, —C(O)-cycloalkenyl, —CO$_2$-cycloalkenyl, —S-cycloalkenyl, —S(O)-cycloalkenyl, —S(O)$_2$-cycloalkenyl, —N($R^1$)-cycloalkenyl, —C(O)—N($R^{21}$)-cycloalkenyl, —N($R^{21}$)—C(O)-cycloalkenyl, —N($R^{21}$)—C(O)—N($R^{21}$)-cycloalkenyl, —N($R^{21}$)—S(O)-cycloalkenyl, —N($R^{21}$)—S(O)$_2$-cycloalkenyl, —N($R^{21}$)—S(O)$_2$—N($R^{21}$)-cycloalkenyl, —S(O)—N($R^{21}$)-cycloalkenyl and —S(O)$_2$—N($R^{21}$)-cycloalkenyl;

(5) heterocycloalkenyl, —O-heterocycloalkenyl, —C(O)-heterocycloalkenyl, —CO$_2$-heterocycloalkenyl, —S-heterocycloalkenyl, —S(O)-heterocycloalkenyl, —S(O)$_2$-heterocycloalkenyl, —N($R^1$)-heterocycloalkenyl, —C(O)—N($R^{21}$)-heterocycloalkenyl, —N($R^{21}$)—C(O)-heterocycloalkenyl, —N($R^{21}$)—C(O)—N($R^{21}$)-heterocycloalkenyl, —N($R^{21}$)—S(O)-heterocycloalkenyl, —N($R^{21}$)—S(O)$_2$-heterocycloalkenyl, —N($R^{21}$)—S(O)$_2$—N($R^{21}$)-heterocycloalkenyl, —S(O)—N($R^{21}$)-heterocycloalkenyl and —S(O)$_2$—N($R^{21}$)-heterocycloalkenyl;

(6) alkyl, —O-alkyl, —C(O)-alkyl, —CO$_2$-alkyl, —S-alkyl, —S(O)-alkyl, —S(O)$_2$-alkyl, —N($R^1$)-alkyl, —C(O)—N($R^{21}$)-alkyl, —N($R^{21}$)—C(O)-alkyl, —N($R^{21}$)—C(O)—N($R^{21}$)-alkyl, —N($R^{21}$)—S(O)-alkyl, —N($R^{21}$)—S(O)$_2$-alkyl, —N($R^{21}$)—S(O)$_2$—N($R^{21}$)-alkyl, —S(O)—N($R^{21}$)-alkyl and —S(O)$_2$—N($R^{21}$)-alkyl;

(7) heteroalkyl, —O-heteroalkyl, —C(O)-heteroalkyl, —CO$_2$-heteroalkyl, —S-heteroalkyl, —S(O)-heteroalkyl, —S(O)$_2$-heteroalkyl, —N($R^1$)-heteroalkyl, —C(O)—N($R^{21}$)-heteroalkyl, —N($R^{21}$)—C(O)-heteroalkyl, —N($R^{21}$)—C(O)—N($R^{21}$)-heteroalkyl, —N($R^{21}$)—S(O)-heteroalkyl, —N($R^{21}$)—S(O)$_2$-heteroalkyl, —N($R^{21}$)—S(O)$_2$—N($R^{21}$)-heteroalkyl, —S(O)—N($R^{21}$)-heteroalkyl and —S(O)$_2$—N($R^{21}$)-heteroalkyl;

(8) alkenyl, —O-alkenyl, —C(O)-alkenyl, —CO$_2$-alkenyl, —S-alkenyl, —S(O)-alkenyl, —S(O)$_2$-alkenyl, —N($R^1$)-alkenyl, —C(O)—N($R^{21}$)-alkenyl, —N($R^{21}$)—C(O)-alkenyl, —N($R^{21}$)—C(O)—N($R^{21}$)-alkenyl, —N($R^{21}$)—S(O)-alkenyl, —N($R^{21}$)—S(O)$_2$-alkenyl, —N($R^{21}$)—S(O)$_2$—N($R^{21}$)-alkenyl, —S(O)—N($R^{21}$)-alkenyl and —S(O)$_2$—N($R^{21}$)-alkenyl;

(9) alkynyl, —O-alkynyl, —C(O)-alkynyl, —CO$_2$-alkynyl, —S-alkynyl, —S(O)-alkynyl, —S(O)$_2$-alkynyl, —N($R^1$)-alkynyl, —C(O)—N($R^{21}$)-alkynyl, —N($R^{21}$)—C(O)-alkynyl, —N($R^{21}$)—C(O)—N($R^{21}$)-alkynyl, —N($R^{21}$)—S(O)-alkynyl, —N($R^{21}$)—S(O)$_2$-alkynyl, —N($R^{21}$)—S(O)$_2$—N($R^{21}$)-alkynyl, —S(O)—N($R^{21}$)-alkynyl and —S(O)$_2$—N($R^{21}$)-alkynyl;

(10) aryl, —O-aryl, —C(O)-aryl, —CO$_2$-aryl, —S-aryl, —S(O)-aryl, —S(O)$_2$-aryl, —N($R^1$)-aryl, —C(O)—N($R^{21}$)-aryl, —N($R^{21}$)—C(O)-aryl, —N($R^{21}$)—C(O)—N($R^{21}$)-aryl, —N($R^{21}$)—S(O)-aryl, —N($R^{21}$)—S(O)$_2$-aryl, —N($R^{21}$)—S(O)$_2$—N($R^{21}$)-aryl, —S(O)—N($R^{21}$)-aryl and —S(O)$_2$—N($R^{21}$)-aryl;

(11) heteroaryl, —O-heteroaryl, —C(O)-heteroaryl, —CO$_2$-heteroaryl, —S-heteroaryl, —S(O)-heteroaryl, —S(O)$_2$-heteroaryl, —N($R^1$)-heteroaryl, —C(O)—N($R^{21}$)-heteroaryl, —N($R^{21}$)—C(O)-heteroaryl, —N($R^{21}$)—C(O)—N($R^{21}$)-heteroaryl, —N($R^{21}$)—S(O)-heteroaryl, —N($R^{21}$)—S(O)$_2$-heteroaryl, —N($R^{21}$)—S(O)$_2$—N($R^{21}$)-heteroaryl, —S(O)—N($R^{21}$)-heteroaryl and —S(O)$_2$—N($R^{21}$)-heteroaryl;

wherein said heteroalkyl of (7), heterocycloalkyl of (3), heterocycloalkenyl of (5), and heteroaryl of (11) are connected through any available carbon atom or heteroatom;

and wherein said alkyl, heteroalkyl, cycloalkyl, heterocycloalkyl, aryl, heteroaryl, alkenyl, alkynyl, cycloalkenyl, and heterocycloalkenyl of (1) through (11) are unsubstituted or substituted with one or more groups independently selected from $R^2$.

In another embodiment of the invention, each V is independently selected from the group consisting of: alkyl unsubstituted or substituted with one to three groups independently selected from:

(1) halo, —NH$_2$, —OH, —SH, —SO$_2$H, CO$_2$H, —SF$_5$, —OSF$_5$, cyano and —CHO;

(2) cycloalkyl, —O-cycloalkyl, —C(O)-cycloalkyl, —CO$_2$-cycloalkyl, —S-cycloalkyl, —S(O)-cycloalkyl, —S(O)$_2$-cycloalkyl, —N($R^1$)-cycloalkyl, —C(O)—N($R^{21}$)-cycloalkyl, —N($R^{21}$)—C(O)-cycloalkyl, —N($R^{21}$)—C(O)—N($R^{21}$)-cycloalkyl, —N($R^{21}$)—S(O)-cycloalkyl, —N($R^{21}$)—S(O)$_2$-cycloalkyl, —N($R^{21}$)—S(O)$_2$—N($R^{21}$)-cycloalkyl, —S(O)—N($R^{21}$)-cycloalkyl and —S(O)$_2$—N($R^{21}$)-cycloalkyl;

(3) heterocycloalkyl, —O-heterocycloalkyl, —C(O)-heterocycloalkyl, —CO$_2$-heterocycloalkyl, —S-heterocycloalkyl, —S(O)-heterocycloalkyl, —S(O)$_2$-heterocycloalkyl, —N(R$^1$)-heterocycloalkyl, —C(O)—N(R$^{21}$)-heterocycloalkyl, —N(R$^{21}$)—C(O)-heterocycloalkyl, —N(R$^{21}$)—C(O)—N(R$^{21}$)-heterocycloalkyl, —N(R$^{21}$)—S(O)-heterocycloalkyl, —N(R$^{21}$)—S(O)$_2$-heterocycloalkyl, —N(R$^{21}$)—S(O)$_2$—N(R$^{21}$)-heterocycloalkyl, —S(O)—N(R$^{21}$)-heterocycloalkyl and —S(O)$_2$—N(R$^{21}$)-heterocycloalkyl;

(4) cycloalkenyl, —O-cycloalkenyl, —C(O)-cycloalkenyl, —CO$_2$-cycloalkenyl, —S-cycloalkenyl, —S(O)-cycloalkenyl, —S(O)$_2$-cycloalkenyl, —N(R$^1$)-cycloalkenyl, —C(O)—N(R$^{21}$)-cycloalkenyl, —N(R$^{21}$)—C(O)-cycloalkenyl, —N(R$^{21}$)—C(O)—N(R$^{21}$)-cycloalkenyl, —N(R$^{21}$)—S(O)-cycloalkenyl, —N(R$^{21}$)—S(O)$_2$-cycloalkenyl, —N(R$^{21}$)—S(O)$_2$—N(R$^{21}$)— cycloalkenyl, —S(O)—N(R$^{21}$)-cycloalkenyl and —S(O)$_2$—N(R$^{21}$)-cycloalkenyl;

(5) heterocycloalkenyl, —O-heterocycloalkenyl, —C(O)-heterocycloalkenyl, —CO$_2$-heterocycloalkenyl, —S-heterocycloalkenyl, —S(O)-heterocycloalkenyl, —S(O)$_2$-heterocycloalkenyl, —N(R$^1$)-heterocycloalkenyl, —C(O)—N(R$^{21}$)-heterocycloalkenyl, and —N(R$^{21}$)—C(O)-heterocycloalkenyl, —N(R$^{21}$)—C(O)—N(R$^{21}$)-heterocycloalkenyl, —N(R$^{21}$)—S(O)-heterocycloalkenyl, —N(R$^{21}$)—S(O)$_2$-heterocycloalkenyl, —N(R$^{21}$)—S(O)$_2$—N(R$^{21}$)-heterocycloalkenyl, —S(O)—N(R$^{21}$)-heterocycloalkenyl and —S(O)$_2$—N(R$^{21}$)-heterocycloalkenyl;

(6) alkyl, —O-alkyl, —C(O)-alkyl, —CO$_2$-alkyl, —S-alkyl, —S(O)-alkyl, —S(O)$_2$-alkyl, —N(R$^1$)-alkyl, —C(O)—N(R$^{21}$)-alkyl, —N(R$^{21}$)—C(O)-alkyl, —N(R$^{21}$)—C(O)—N(R$^{21}$)-alkyl, —N(R$^{21}$)—S(O)-alkyl, —N(R$^{21}$)—S(O)$_2$-alkyl, —N(R$^{21}$)—S(O)$_2$—N(R$^{21}$)-alkyl, —S(O)—N(R$^{21}$)-alkyl and —S(O)$_2$—N(R$^{21}$)-alkyl;

(7) heteroalkyl, —O-heteroalkyl, —C(O)-heteroalkyl, —CO$_2$-heteroalkyl, —S-heteroalkyl, —S(O)-heteroalkyl, —S(O)$_2$-heteroalkyl, —N(R$^1$)-heteroalkyl, —C(O)—N(R$^{21}$)-heteroalkyl, —N(R$^{21}$)—C(O)-heteroalkyl, —N(R$^{21}$)—C(O)—N(R$^{21}$)-heteroalkyl, —N(R$^{21}$)—S(O)-heteroalkyl, —N(R$^{21}$)—S(O)$_2$-heteroalkyl, —N(R$^{21}$)—S(O)$_2$—N(R$^{21}$)-heteroalkyl, —S(O)—N(R$^{21}$)-heteroalkyl and —S(O)$_2$—N(R$^{21}$)-heteroalkyl;

(8) alkenyl, —O-alkenyl, —C(O)-alkenyl, —CO$_2$-alkenyl, —S-alkenyl, —S(O)-alkenyl, —S(O)$_2$-alkenyl, —N(R$^1$)-alkenyl, —C(O)—N(R$^{21}$)-alkenyl, —N(R$^{21}$)—C(O)-alkenyl, —N(R$^{21}$)—C(O)—N(R$^{21}$)-alkenyl, —N(R$^{21}$)—S(O)-alkenyl, —N(R$^{21}$)—S(O)$_2$-alkenyl, —N(R$^{21}$)—S(O)$_2$—N(R$^{21}$)-alkenyl, —S(O)—N(R$^{21}$)-alkenyl and —S(O)$_2$—N(R$^{21}$)-alkenyl;

(9) alkynyl, —O-alkynyl, —C(O)-alkynyl, —CO$_2$-alkynyl, —S-alkynyl, —S(O)-alkynyl, —S(O)$_2$-alkynyl, —N(R$^1$)-alkynyl, —C(O)—N(R$^{21}$)-alkynyl, —N(R$^{21}$)—C(O)-alkynyl, —N(R$^{21}$)—C(O)—N(R$^{21}$)-alkynyl, —N(R$^{21}$)—S(O)-alkynyl, —N(R$^{21}$)—S(O)$_2$-alkynyl, —N(R$^{21}$)—S(O)$_2$—N(R$^{21}$)-alkynyl, —S(O)—N(R$^{21}$)-alkynyl and —S(O)$_2$—N(R$^{21}$)-alkynyl;

(10) aryl, —O-aryl, —C(O)-aryl, —CO$_2$-aryl, —S-aryl, —S(O)-aryl, —S(O)$_2$-aryl, —N(R$^1$)-aryl, —C(O)—N(R$^{21}$)-aryl, —N(R$^{21}$)—C(O)-aryl, —N(R$^{21}$)—C(O)—N(R$^{21}$)-aryl, —N(R$^{21}$)—S(O)-aryl, —N(R$^{21}$)—S(O)$_2$-aryl, —N(R$^{21}$)—S(O)$_2$—N(R$^{21}$)-aryl, —S(O)—N(R$^{21}$)-aryl and —S(O)$_2$—N(R$^{21}$)-aryl;

(11) heteroaryl, —O-heteroaryl, —C(O)-heteroaryl, —CO$_2$-heteroaryl, —S-heteroaryl, —S(O)-heteroaryl, —S(O)$_2$-heteroaryl, —N(R$^1$)-heteroaryl, —C(O)—N(R$^{21}$)-heteroaryl, —N(R$^{21}$)—C(O)-heteroaryl, —N(R$^{21}$)—C(O)—N(R$^{21}$)-heteroaryl, —N(R$^{21}$)—S(O)-heteroaryl, —N(R$^{21}$)—S(O)$_2$-heteroaryl, —N(R$^{21}$)—S(O)$_2$—N(R$^{21}$)-heteroaryl, —S(O)—N(R$^{21}$)-heteroaryl and —S(O)$_2$—N(R$^{21}$)-heteroaryl, wherein said heteroalkyl of (7), heterocycloalkyl of (3), heterocycloalkenyl of (5), and heteroaryl of (11) are connected through any available carbon or heteroatom, and wherein said alkyl, heteroalkyl, cycloalkyl, heterocycloalkyl, aryl, heteroaryl, alkenyl, alkynyl, cycloalkenyl, and heterocycloalkenyl of (1) through (11) are unsubstituted or substituted with one or more groups independently selected from R$^2$.

In another embodiment, each V is independently selected from the group consisting of: C$_{1-6}$alkyl and cycloalkyl.

In one embodiment of the invention, G is selected from the group consisting of:
(1a) hydrogen, halo, —NH$_2$, —OH, CO$_2$H and cyano;
(2a) cycloalkyl, —O-cycloalkyl and —N(R$^1$)-cycloalkyl;
(3a) heterocycloalkyl, —O-heterocycloalkyl and —N(R$^1$)-heterocycloalkyl;
(6a) alkyl, —O-alkyl and —N(R$^1$)alkyl;
(7a) heteroalkyl, —O-heteroalkyl and —N(R$^1$)-heteroalkyl;
(8a) alkenyl, —O-alkenyl and —N(R$^1$)-alkenyl,
(9a) alkynyl, —O-alkynyl and —N(R$^1$)-alkynyl;
(10a) aryl, —O-aryl, —C(O)-aryl, —S-aryl, —S(O)-aryl, —S(O)$_2$-aryl, —N(R$^1$)-aryl and —C(O)—N(R$^{21}$)-aryl;
(11a) heteroaryl, —O-heteroaryl, —C(O)-heteroaryl, —S-heteroaryl, —S(O)-heteroaryl, —S(O)$_2$-heteroaryl, —N(R$^1$)-heteroaryl and —C(O)—N(R$^{21}$)-heteroaryl;
wherein said heteroalkyl, heterocycloalkyl, and heteroaryl of G are connected through any available carbon or heteroatom, and wherein said alkyl, heteroalkyl, cycloalkyl, heterocycloalkyl, aryl, said heteroaryl, alkenyl, and alkynyl of G are unsubstituted or substituted with one or more groups independently selected from R$^2$.

In another embodiment of the invention, G is selected from the group consisting of:
(1a) hydrogen;
(2a) cycloalkyl and —N(R$^1$)-cycloalkyl;
(3a) heterocycloalkyl and —N(R$^1$)-heterocycloalkyl;
(6a) alkyl and —N(R$^1$)-alkyl;
(7a) heteroalkyl and —N(R$^1$)-heteroalkyl;
(8a) alkenyl and —N(R$^1$)-alkenyl;
(10a) aryl and —N(R$^1$)-aryl;
(11a) heteroaryl and —N(R$^1$)-heteroaryl,
wherein said heteroalkyl, heterocycloalkyl and heteroaryl of G are connected through any available carbon or heteroatom, and wherein said alkyl, heteroalkyl, cycloalkyl, heterocycloalkyl, aryl, heteroaryl and alkenyl of G are unsubstituted or substituted with one or more groups independently selected from R$^2$.

In another embodiment of the invention, G is selected from the group consisting of:
(1a) hydrogen;
(2a) cycloalkyl and —N(R$^1$)-cycloalkyl;
(3a) heterocycloalkyl;
(6a) alkyl;
(10a) aryl, and
(11a) heteroaryl,
wherein said heterocycloalkyl, and heteroaryl of G are connected through any available carbon or heteroatom, and wherein said alkyl, cycloalkyl, heterocycloalkyl, aryl, and heteroaryl, of G are unsubstituted or substituted with one to three groups independently selected from R$^2$.

In another embodiment, G represents a phenyl group optionally substituted with 1-3 groups selected from halo, $C_{1-3}$alkyl, $C_{1-3}$alkoxy, halo$C_{1-3}$alkyl and halo$C_{1-3}$alkoxy, or with a phenyl ring optionally substituted with 1-3 halo atoms.

In the various embodiments of the compounds of the invention described herein, functional groups for $L^1$ are to be read from left to right unless otherwise stated.

In another embodiment of the invention, $L^1$ is selected from the group consisting of —N($R^4$)—(C($R^{5A}$)$_2$)—(C($R^5$)$_2$)$_q$—, —(C($R^{5A}$)$_2$)—(C($R^5$)$_2$)$_r$—(C($R^{5A}$)$_2$)—N($R^4$)—, —O—(C($R^{5A}$)$_2$)—(C($R^5$)$_2$)$_q$—, —(C($R^{5A}$)$_2$)—(C($R^5$)$_2$)$_r$—(C($R^{5A}$)$_2$)—O—, and —(C($R^{5A}$)$_2$)—(C($R^5$)$_2$)$_s$—.

In another embodiment of the invention, $L^1$ is selected from the group consisting of —(C($R^{5A}$)$_2$)—(C($R^5$)$_2$)$_r$—(C($R^{5A}$)$_2$)—N($R^4$)—, —(C($R^{5A}$)$_2$)—(C($R^5$)$_2$)$_r$—(C($R^{5A}$)$_2$)—O— and —(C($R^{5A}$)$_2$)—(C($R^5$)$_2$)$_s$—.

In another embodiment of the invention, $L^1$ represents —(C($R^{5A}$)$_2$)—(C($R^5$)$_2$)$_s$—.

In another embodiment, $L^1$ is selected from the group consisting of a bond, —NH—(CH$_2$)$_2$—, —O—(CH$_2$)$_2$—, —O—, —NH—, —N(CH$_3$)—, —CH$_2$—, —CH(C$_{1-6}$alkyl)- and —CH(C$_{3-6}$cycloalkyl)-.

In another embodiment, $L^1$ is selected from the group consisting of: —CH$_2$—, —CH(CH$_3$)—, —CH$_2$CH$_2$—, —CH(CH$_2$CH$_2$CH$_2$CH$_3$)—, —CH(CH(CH$_3$)$_2$)—, —CH(cyclopropyl)- and —CH(CH$_2$CH$_2$(CH$_3$)$_2$)—.

In another embodiment, $L^1$ is selected from the group consisting of: —CH(cycloalkylalkyl)- and —CH(heterocycloalkylalkyl)-.

In another embodiment, $L^1$ is —C($R^{5A}$)$_2$—, wherein each $R^{5A}$ is independently selected from the group consisting of H, lower alkyl, haloalkyl, heteroalkyl, cyano-substituted lower alkyl, hydroxy-substituted lower alkyl, cycloalkyl, -alkylcycloalkyl, heterocycloalkyl and -alkylheterocycloalkyl.

In another embodiment, $L^1$ is —CH($R^{5A}$)—, wherein $R^{5A}$ is selected from the group consisting of H, lower alkyl, haloalkyl, heteroalkyl, cyano-substituted lower alkyl, hydroxy-substituted lower alkyl, cycloalkyl, -alkylcycloalkyl, heterocycloalkyl, and -alkylheterocycloalkyl.

In another embodiment, $L^1$ is selected from the group consisting of:

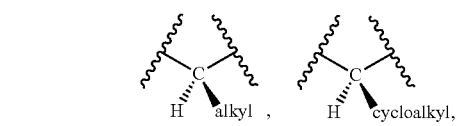

and —(CH$_2$)$_{1-3}$—.

In another embodiment, $L^1$ is selected from the group consisting of:

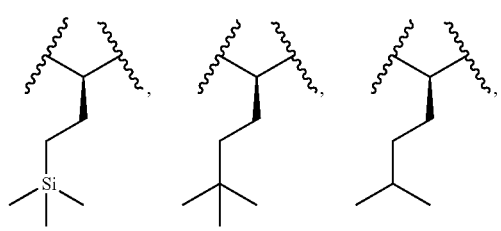

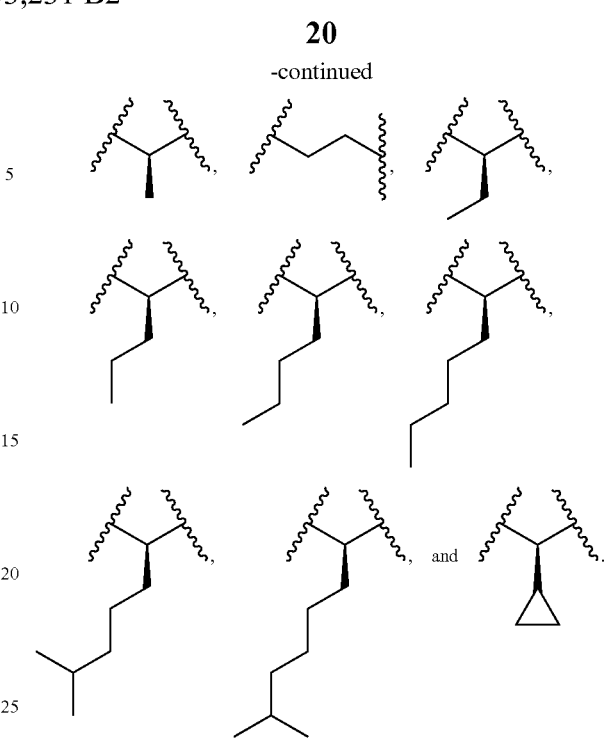

In another embodiment, $L^1$ is selected from the group consisting of:

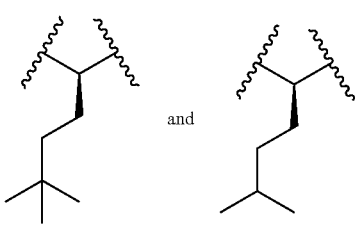

In another embodiment, $L^1$ is selected from the group consisting of:

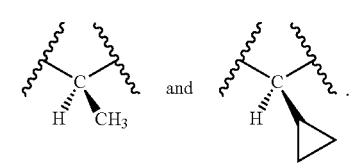

In another embodiment, $L^1$ is selected from the group consisting of:

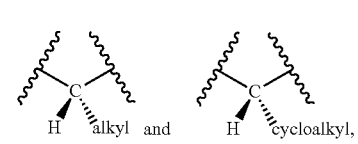

In another embodiment, $L^1$ is selected from the group consisting of:

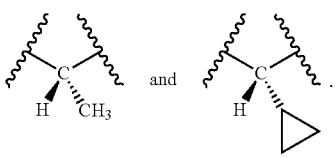

In another embodiment, $L^1$ is selected from the group consisting of:

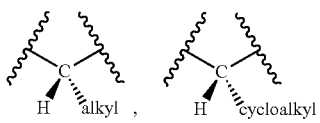

and —$(CH_2)_{1-3}$—.

In another embodiment, $L^1$ is selected from the group consisting of:

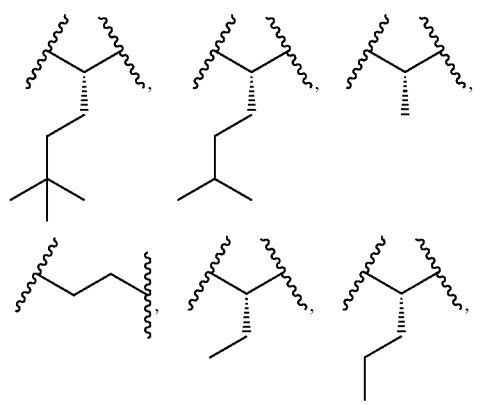

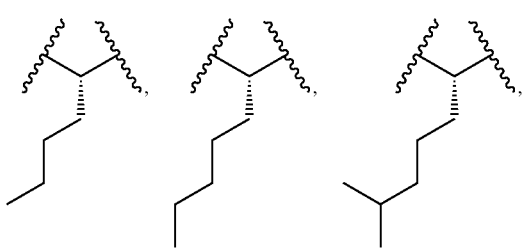

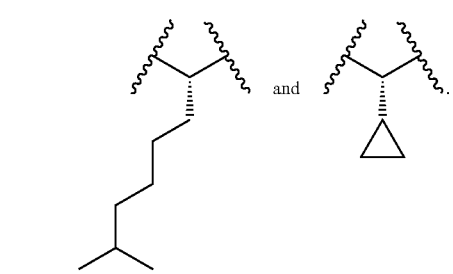

In another embodiment, $L^1$ is selected from the group consisting of:

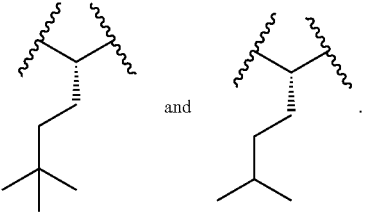

In another embodiment, ring B is phenyl.

In another embodiment, ring B is a phenyl ring wherein the -$L^1$- and the —$C(O)N(R^3)Z$ moieties shown in the formula are bound to said phenyl ring in a 1,4-relationship, and wherein said phenyl ring is (in addition to the -$L^1$- and —$C(O)N(R^3)$—Z moieties shown) optionally further substituted with one or more substituents $R^a$, wherein each $R^a$ (when present) is independently selected from the group consisting of halo, alkyl, and haloalkyl.

In another embodiment, ring B is phenyl which, in addition to the moieties and —$C(O)N(R^3)$—Z shown in the formula, is further substituted with one or more independently selected $R^a$ groups.

In another embodiment, ring B is a phenyl which, in addition to the moieties $L^1$- and —$C(O)N(R^3)$—Z shown in the formula, is further substituted with from 1 to 2 substituents, each independently selected from halo, alkyl, and haloalkyl.

In another embodiment, ring B is a 5-6 membered heteroaromatic ring having from 1 to 3 ring heteroatoms independently selected from N, O, and S, wherein said ring B is not further substituted.

In one embodiment, ring B is a 5-membered heteroaromatic ring having from 1 to 3 ring heteroatoms independently selected from N, O, and S, wherein said ring B is further substituted with one or more substituents. Said further substituents in such embodiments may be bound to one or more available ring carbon atoms and/or ring nitrogen atoms.

In another embodiment, ring B is a 5-membered heteroaromatic ring containing from 1 to 3 ring heteroatoms independently selected from N, O, and S, wherein the -$L^1$- and the —$C(O)N(R^3)$—Z moieties shown in the formula are bound to said 5-membered ring in a 1,3-relationship, and wherein said 5-membered heteroaromatic ring is (in addition to the -$L^1$- and —$C(O)N(R^3)$—Z moieties shown) optionally further substituted with one or more substituents $R^a$, wherein each $R^a$ (when present) is independently selected from the group consisting of halo, alkyl, and haloalkyl.

In one embodiment, ring B is a 5-membered heteroaromatic ring having from 1 to 3 ring heteroatoms independently selected from N, O, and S, wherein said 5-membered heteroaromatic ring is further substituted with from 1 to 2 substituents, each substituent being independently selected from halo, alkyl, and haloalkyl. In one such embodiment, ring B contains two said substituents. In another such embodiment, ring B contains one said substitutent.

In one embodiment, ring B is a 5-membered heteroaromatic ring, selected from the group consisting of: furan, thiophene, pyrrole, imidazole, pyrazole, 1,2,3-triazole, 1,2,4-triazole, thiazole, thiadiazole, oxazole, oxadiazole, and isoxazole, each of which may be optionally further substituted as described herein. Non-limiting examples of ring B (shown connected to moieties $L^1$ and —C(O)—N($R^3$)—Z) include:

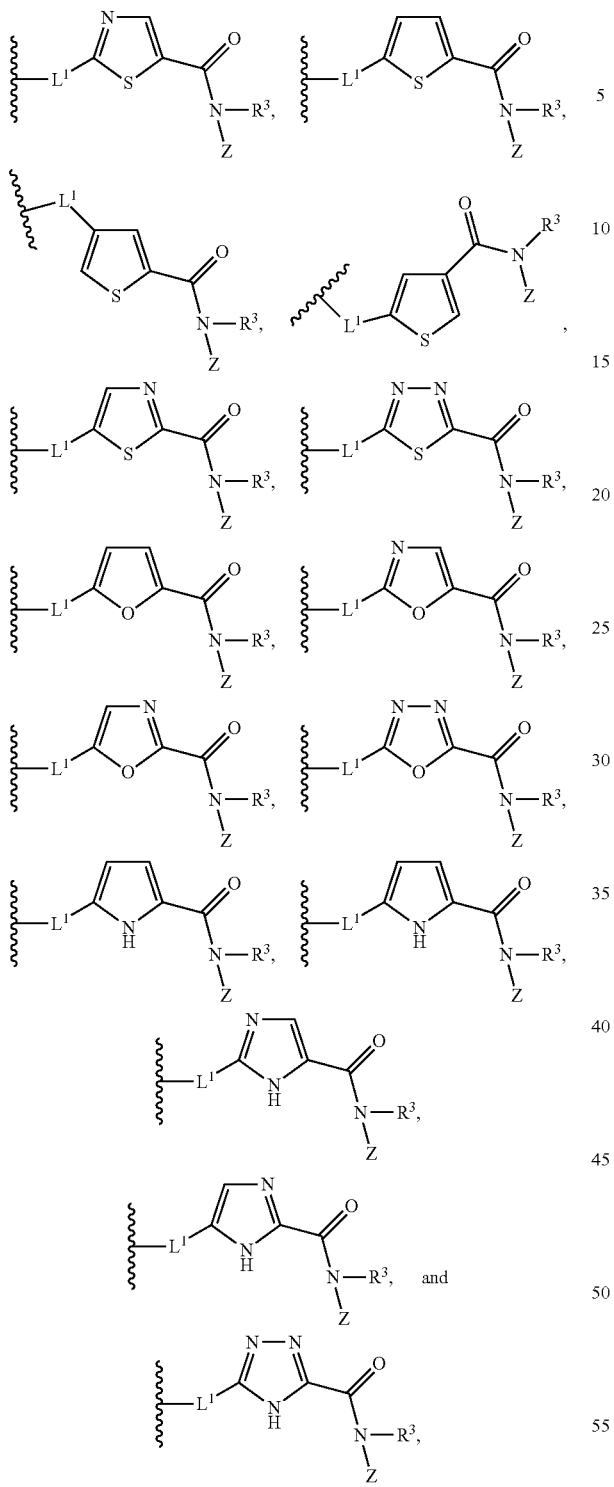

wherein each ring B shown is optionally further substituted on an available ring carbon atom or ring nitrogen atom with one or more groups $R^a$, wherein each $R^a$, when attached to a ring carbon atom, is independently selected from halo, alkyl, and haloalkyl, and wherein each $R^a$, when attached to a ring nitrogen atom, is independently selected from alkyl, and haloalkyl. Non-limiting examples of such groups substituted on an available ring nitrogen atom include:

In one embodiment, ring B is a 6-membered heteroaromatic ring having from 1 to 3 ring nitrogen atoms, wherein said ring B is not further substituted.

In one embodiment, ring B is a 6-membered heteroaromatic ring having from 1 to 3 ring nitrogen atoms wherein said ring B is further substituted with one or more substituents. Said further substituents in such embodiments may be bound to one or more available ring carbon atoms and/or ring nitrogen atoms.

In another embodiment, ring B is a 6-membered heteroaromatic ring containing from 1 to 3 ring nitrogen atoms, wherein the -$L^1$- and the —C(O)N($R^3$)—Z moieties shown in the formula are bound to said 6-membered ring in a 1,4-relationship, and wherein said 6-membered heteroaromatic ring is (in addition to -$L^1$- and —C(O)N($R^3$)Z moieties shown) optionally further substituted with one or more substituents $R^a$, wherein each $R^a$ (when present) is independently selected from the group consisting of halo, alkyl, and haloalkyl.

In another embodiment, ring B is a 6-membered heteroaromatic ring having from 1 to 3 ring nitrogen atoms, wherein said ring B is further substituted with from 1 to 3 substituents, each substituent being independently selected from halo, alkyl, and haloalkyl. In one such embodiment, ring B contains three said substituents. In one such embodiment, ring B contains two said substituents. In another such embodiment, ring B contains one said substitutent.

In another embodiment, ring B is a 5-6 membered heteroaromatic ring selected from the group consisting of: thiophene, pyridine, pyrimidine, pyrazine, pyridazine, and triazine, each of which may be optionally further substituted as described herein. Non-limiting examples of ring B (shown connected to moieties $L^1$ and —C(O)—N($R^3$)—Z) include

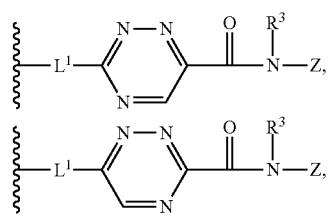

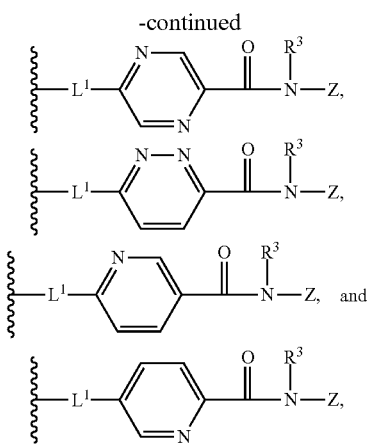

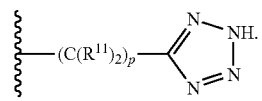

wherein any of such moieties may be optionally further substituted with one or more groups $R^a$, wherein each $R^a$ is independently selected from halo, alkyl, and haloalkyl.

In another embodiment $R^3$ is H.

In another embodiment $R^3$ is selected from methyl, ethyl, n-propyl and isopropyl.

In another embodiment Z is a moiety selected from the group consisting of: —$C(R^{11})_2$)—$(C(R^{12}R^{13}))_m$—C(O)OH, —$(C(R^{11})_2)$—$(C(R^{14})_2)_n$—C(O)OH, —$(C(R^{11})_2)$—$(C(R^{12}R^{13}))_m$—C(O)Oalkyl, —$(C(R^{11})_2)$—$(C(R^{14})_2)_n$—C(O)Oalkyl and

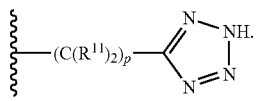

In another embodiment Z is a moiety selected from the group consisting of: —$(C(R^{11})_2)$—$(C(R^{12}R^{13}))_m$—C(O)OH, —$(C(R^{11})_2)$—$(C(R^{14})_2)_n$—C(O)OH, —$(C(R^{11})_2)$—$(C(R^{12}R^{13}))_m$—C(O)Oalkyl and —$(C(R^{11})_2)$—$(C(R^{14})_2)_n$—C(O)Oalkyl.

In another embodiment, Z is —$(C(R^{11})_2)$—$(C(R^{12})(R^{13}))_m$—C(O)OH.

Pharmaceutically acceptable salts of such acids are also contemplated as being within the scope of the invention. Thus, in another embodiment, Z is —$(C(R^{11})_2)$—$(C(R^{12})(R^{13}))_m$—C(O)O⁻Na⁺. Additional non-limiting salts contemplated as alternatives to the sodium salt are known to those of ordinary skill in the art and/or are as described herein.

In another embodiment, Z is —CH$_2$—(CH(CH$_3$))C(O)OH.

In another embodiment, Z is —CH$_2$CH$_2$—(CH$_2$)C(O)OH.
In another embodiment, Z is —CH$_2$—C(CH$_3$)$_2$C(O)OH.
In another embodiment, Z is —CH$_2$—C(CH$_3$)(OH)C(O)OH.
In another embodiment, Z is —CH$_2$CH$_2$C(O)OH.
In another embodiment, Z is —CH$_2$—CH(OH)C(O)OH.
In another embodiment, Z is —CH(CH$_3$)—CH$_2$C(O)OH.
In another embodiment, Z is —C(CH$_3$)$_2$—CH$_2$C(O)OH.
In another embodiment, Z is —$(C(R^{11})_2)$—$(C(R^{14})_2)_n$—C(O)OH.
In another embodiment, Z is —CH$_2$CH(F)C(O)OH.
In another embodiment, Z is —CH$_2$CF$_2$C(O)OH.
In another embodiment, Z is —CH(CH$_3$)CF$_2$C(O)OH.
In another embodiment, Z is —CH$_2$CH$_2$CF$_2$C(O)OH.
In another embodiment, Z is

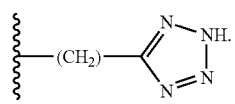

In another embodiment, Z is

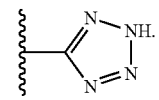

In another embodiment, Z is

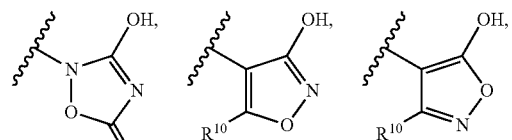

In another embodiment when Z is a moiety selected from —$(C(R^{11})_2)$—$(C(R^{12}R^{13}))_m$—C(O)OH, or —$(C(R^{11})_2)$—$(C(R^{14})_2)_n$—C(O)OH, the —C(O)OH group may be replaced by a moiety -Q, wherein Q is selected from the group consisting of:

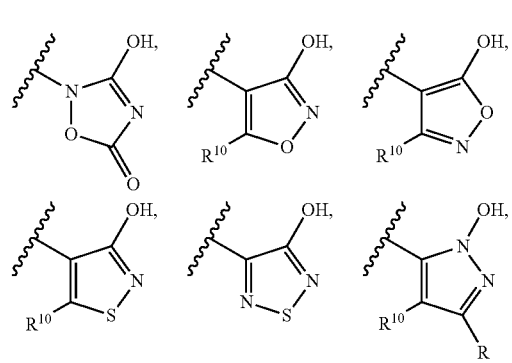

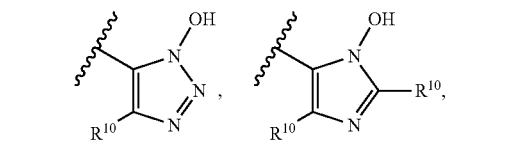

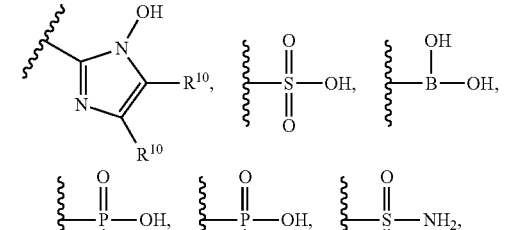

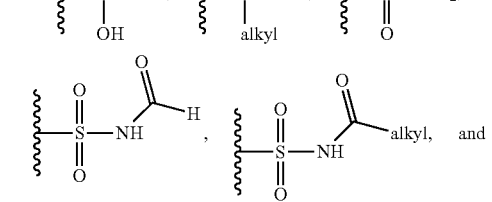

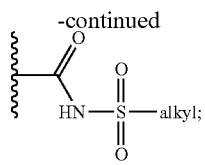

Such moieties Q are readily available to those skilled in the art and may be made, for example, by methods according to Stensbol et al., J. Med. Chem., 2002, 45, 19-31, or according to Moreira Lima et al., Current Med. Chem., 2005, 12, 23-49.

As indicated above, tautomers of the compounds of the various formulas of the invention described herein are embraced by the present invention. For example, it shall be understood that tetrazoles (such as those described in variable "Z") written as:

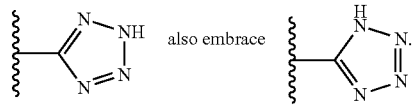

In another embodiment, q is 0.
In another embodiment, q is 1.
In another embodiment, q is 2.
In another embodiment, —$(C(R^5)_2)_s$— is selected from the group consisting of —$(C(CH_3)_2)_s$—, —$(CH(CH_3))_s$—, and —$(CH_2)_s$—, wherein s is 1-3.
In another embodiment, —$(C(R^5)_2)_s$— is selected from the group consisting of —$(C(CH_3)_2)_s$—, —$(CH(CH_3))_s$—, and —$(CH_3)_s$—, wherein s is 1-2.
In another embodiment, —$(C(R^5)_2)_s$— is selected from the group consisting of —$(C(CH_3)_2)_s$—, —$(CH(CH_3))_s$—, and —$(CH_2)_s$—, wherein s is 1.
In another embodiment, —$(C(R^5)_2)_s$— is selected from the group consisting of —$(CH(CH_3))_s$— and —$(CH_2)_s$—, wherein s is 1.
In another embodiment, —$(C(R^5)_2)_s$— is —$(CH(CH_3))$—.
In another embodiment, each $R^1$ is independently selected from:
(1b) hydrogen,
(2b) cycloalkyl,
(3b) heterocycloalkyl,
(4b) cycloalkenyl,
(6b) alkyl, —C(O)-alkyl, —$CO_2$-alkyl, —S(O)-alkyl and —$S(O)_2$-alkyl,
(7b) heteroalkyl,
(8b) alkenyl,
(9b) alkynyl,
(10b) aryl,
(11b) heteroaryl,
wherein said heteroalkyl, heterocycloalkyl, and heteroaryl of $R^1$ may be connected through any available carbon or heteroatom,
and wherein said alkyl, heteroalkyl, cycloalkyl, heterocycloalkyl, aryl, heteroaryl, said alkenyl, said alkynyl, said cycloalkenyl, and said heterocycloalkenyl of $R^1$ are unsubstituted or substituted with one or more groups independently selected from $R^2$.
In another embodiment, each $R^1$ is independently selected from:
(1b) hydrogen,
(2b) cycloalkyl,
(3b) heterocycloalkyl,
(6b) alkyl,
(7b) heteroalkyl,
(8b) alkenyl,
(10b) aryl,
(11b) heteroaryl,
wherein said heteroalkyl, heterocycloalkyl, and heteroaryl of $R^1$ may be connected through any available carbon or heteroatom,
and wherein said alkyl, heteroalkyl, cycloalkyl, heterocycloalkyl, aryl and heteroaryl of $R^1$ are unsubstituted or substituted with one to three groups independently selected from $R^2$.
In another embodiment, each $R^1$ is independently selected from:
(1b) hydrogen, and
(6b) alkyl, said alkyl being unsubstituted or substituted with one to three groups independently selected from $R^2$.
In another embodiment, each $R^2$ is independently selected from:
(1c) halo, —$NH_2$, —OH, —SH, —$SO_2H$, $CO_2H$, cyano and —CHO,
(2c) cycloalkyl, —O-cycloalkyl, —C(O)-cycloalkyl, —$CO_2$-cycloalkyl, —S-cycloalkyl, —S(O)-cycloalkyl, —$S(O)_2$-cycloalkyl, —$N(R^6)$-cycloalkyl, —C(O)—$N(R^{21})$-cycloalkyl and —$N(R^{21})$—C(O)-cycloalkyl,
(3c) heterocycloalkyl, —O-heterocycloalkyl, —C(O)-heterocycloalkyl, —$CO_2$-heterocycloalkyl, —S-heterocycloalkyl, —S(O)-heterocycloalkyl, —$S(O)_2$-heterocycloalkyl, —$N(R^6)$-heterocycloalkyl, —C(O)—$N(R^{21})$-heterocycloalkyl and —$N(R^{21})$—C(O)-heterocycloalkyl,
(4c) cycloalkenyl, —O-cycloalkenyl, —C(O)-cycloalkenyl, —$CO_2$-cycloalkenyl, —S-cycloalkenyl, —S(O)-cycloalkenyl, —$S(O)_2$-cycloalkenyl, —$N(R^6)$-cycloalkenyl, —C(O)—$N(R^{21})$-cycloalkenyl and —$N(R^{21})$—C(O)-cycloalkenyl,
(5c) heterocycloalkenyl, —O-heterocycloalkenyl, —C(O)-heterocycloalkenyl, —$CO_2$-heterocycloalkenyl, —S-heterocycloalkenyl, —S(O)-heterocycloalkenyl, —$S(O)_2$-heterocycloalkenyl, —$N(R^6)$-heterocycloalkenyl, —C(O)—$N(R^{21})$-heterocycloalkenyl, and —$N(R^{21})$—C(O)-heterocycloalkenyl,
(6c) alkyl, —O-alkyl, —C(O)-alkyl, —$CO_2$-alkyl, —S-alkyl, —S(O)-alkyl, —$S(O)_2$-alkyl, —$N(R^6)$-alkyl, —C(O)—$N(R^{21})$-alkyl, —$N(R^{21})$—C(O)-alkyl, —$N(R^{21})$—C(O)—$N(R^{21})$-alkyl, —$N(R^{21})$—S(O)-alkyl, —$N(R^{21})$—$S(O)_2$-alkyl, —$N(R^{21})$—$S(O)_2$—$N(R^{21})$-alkyl, —S(O)—$N(R^{21})$-alkyl, —$S(O)_2$—$N(R^{21})$-alkyl,
(7c) heteroalkyl, —O-heteroalkyl, —C(O)-heteroalkyl, —$CO_2$-heteroalkyl, —S-heteroalkyl, —S(O)-heteroalkyl, —$S(O)_2$-heteroalkyl, —$N(R^6)$-heteroalkyl, —C(O)—N($R^{21}$)-heteroalkyl and —$N(R^{21})$—C(O)-heteroalkyl,
(8c) alkenyl, —O-alkenyl, —C(O)-alkenyl, —$CO_2$-alkenyl, —S-alkenyl, —S(O)-alkenyl, —$S(O)_2$-alkenyl, —$N(R^6)$-alkenyl, —C(O)—$N(R^{21})$-alkenyl and —$N(R^{21})$—C(O)-alkenyl,
(9c) alkynyl, —O-alkynyl, —C(O)-alkynyl, —$CO_2$-alkynyl, —S-alkynyl, —S(O)-alkynyl, —$S(O)_2$-alkynyl, —$N(R^6)$-alkynyl, —C(O)—$N(R^{21})$-alkynyl and —$N(R^{21})$—C(O)-alkynyl,
(10c) aryl, —O-aryl, —C(O)-aryl, —$CO_2$-aryl, —S-aryl, —S(O)-aryl, —$S(O)_2$-aryl, —$N(R^6)$-aryl, —C(O)—$N(R^{21})$-aryl and —$N(R^{21})$—C(O)-aryl,
(11c) heteroaryl, —O-heteroaryl, —C(O)-heteroaryl, —$CO_2$-heteroaryl, —S-heteroaryl, —S(O)-heteroaryl, —$S(O)_2$-heteroaryl, —$N(R^6)$-heteroaryl, —C(O)—$N(R^{21})$-heteroaryl and —$N(R^{21})$—C(O)-heteroaryl, wherein said heteroalkyl, said heterocycloalkyl, said heterocycloalkenyl, and said heteroaryl of $R^2$ may be connected through any available carbon or heteroatom, and wherein said alkyl, said heteroalkyl, said cycloalkyl, said heterocycloalkyl, said aryl, said heteroaryl, said alkenyl, said alkynyl, said cycloalkenyl, and said heterocycloalkenyl of $R^2$ are unsubstituted or substituted with one or more groups independently selected from $R^7$.

In another embodiment, each $R^1$ is independently selected from:
- (1b) hydrogen,
- (2b) cycloalkyl,
- (3b) heterocycloalkyl,
- (4b) cycloalkenyl, —C(O)-cycloalkenyl, —$CO_2$-cycloalkenyl,
- (6b) alkyl, —C(O)-alkyl, —$CO_2$-alkyl, —S(O)-alkyl, —$S(O)_2$-alkyl,
- (7b) heteroalkyl, —C(O)-heteroalkyl, —$CO_2$-heteroalkyl, —S(O)-heteroalkyl, —$S(O)_2$-heteroalkyl,
- (8b) alkenyl, —C(O)-alkenyl, —$CO_2$-alkenyl, —S(O)-alkenyl, —$S(O)_2$-alkenyl,
- (9b) alkynyl,
- (10b) aryl, —C(O)-aryl, —$CO_2$-aryl,
- (11b) heteroaryl, —C(O)-heteroaryl, —$CO_2$-heteroaryl, wherein said heteroalkyl, said heterocycloalkyl, said heterocycloalkenyl, and said heteroaryl of $R^1$ may be connected through any available carbon or heteroatom, and wherein said alkyl, said heteroalkyl, said cycloalkyl, said heterocycloalkyl, said aryl, said heteroaryl, said alkenyl, said alkynyl, said cycloalkenyl, and said heterocycloalkenyl of $R^1$ are unsubstituted or substituted with one or more groups independently selected from $R^2$.

In another embodiment, each $R^1$ is independently selected from:
- (1b) hydrogen,
- (2b) cycloalkyl,
- (3b) heterocycloalkyl,
- (6b) alkyl,
- (7b) heteroalkyl,
- (8b) alkenyl,
- (10b) aryl, and
- (11b) heteroaryl, wherein said heteroalkyl, heterocycloalkyl, heterocycloalkenyl, and heteroaryl of $R^1$ may be connected through any available carbon or heteroatom, and wherein said alkyl, heteroalkyl, cycloalkyl, heterocycloalkyl, aryl, and heteroaryl of $R^1$ are unsubstituted or substituted with one to three groups independently selected from $R^2$.

In another embodiment, each $R^1$ is independently selected from:
- (1b) hydrogen,
- (2b) cycloalkyl,
- (3b) heterocycloalkyl, and
- (6b) alkyl, wherein said heteroalkyl, heterocycloalkyl, heterocycloalkenyl, and heteroaryl of $R^1$ may be connected through any available carbon or heteroatom, and wherein said alkyl, cycloalkyl, heterocycloalkyl, aryl, and heteroaryl of $R^1$ are unsubstituted or substituted with one to three groups independently selected from $R^2$.

In another embodiment each $R^2$ is independently selected from:
- (1c) halo, —$NH_2$, —OH, —SH, —$SO_2H$ and $CO_2H$,
- (2c) cycloalkyl, —O-cycloalkyl, —C(O)-cycloalkyl, —$CO_2$-cycloalkyl, —S-cycloalkyl, —S(O)-cycloalkyl, —$S(O)_2$-cycloalkyl, —$N(R^6)$-cycloalkyl, —C(O)—$N(R^6)$-cycloalkyl and —$N(R^6)$—C(O)-cycloalkyl,
- (3c) heterocycloalkyl, —O-heterocycloalkyl, —C(O)-heterocycloalkyl, —$CO_2$-heterocycloalkyl, —S-heterocycloalkyl, —S(O)-heterocycloalkyl, —$S(O)_2$-heterocycloalkyl, —$N(R^6)$-heterocycloalkyl, —C(O)—$N(R^{21})$-heterocycloalkyl and —$N(R^{21})$—C(O)-heterocycloalkyl,
- (4c) cycloalkenyl, —O-cycloalkenyl, —C(O)-cycloalkenyl, —$CO_2$-cycloalkenyl, —S-cycloalkenyl, —S(O)-cycloalkenyl, —$S(O)_2$-cycloalkenyl, —$N(R^6)$-cycloalkenyl, —C(O)—$N(R^{21})$-cycloalkenyl and —$N(R^{21})$—C(O)-cycloalkenyl,
- (5c) heterocycloalkenyl, —O-heterocycloalkenyl, —C(O)-heterocycloalkenyl, —$CO_2$-heterocycloalkenyl, —S-heterocycloalkenyl, —S(O)-heterocycloalkenyl, —$S(O)_2$-heterocycloalkenyl, —$N(R^6)$-heterocycloalkenyl, —C(O)—$N(R^{21})$-heterocycloalkenyl, and —$N(R^{21})$—C(O)-heterocycloalkenyl,
- (6c) alkyl, —O-alkyl, —C(O)-alkyl, —$CO_2$-alkyl, —S-alkyl, —S(O)-alkyl, —$S(O)_2$-alkyl, —$N(R^6)$-alkyl, —C(O)—$N(R^{21})$-alkyl, —$N(R^{21})$—C(O)-alkyl, —$N(R^{21})$—C(O)—$N(R^{21})$-alkyl, —$N(R^{21})$—S(O)-alkyl, —$N(R^{21})$—$S(O)_2$-alkyl, —$N(R^{21})$—$S(O)_2$—$N(R^{21})$-alkyl and —S(O)—$N(R^{21})$-alkyl, —$S(O)_2$—$N(R^{21})$-alkyl,
- (7c) heteroalkyl, —O-heteroalkyl, —C(O)-heteroalkyl, —$CO_2$-heteroalkyl, —S-heteroalkyl, —S(O)-heteroalkyl, —$S(O)_2$-heteroalkyl, —$N(R^6)$-heteroalkyl, —C(O)—$N(R^{21})$-heteroalkyl and —$N(R^{21})$—C(O)-heteroalkyl,
- (8c) alkenyl, —O-alkenyl, —C(O)-alkenyl, —$CO_2$-alkenyl, —S-alkenyl, —S(O)-alkenyl, —$S(O)_2$-alkenyl, —$N(R^6)$-alkenyl, —C(O)—$N(R^{21})$-alkenyl and —$N(R^{21})$—C(O)-alkenyl,
- (9c) alkynyl, —O-alkynyl, —C(O)-alkynyl, —$CO_2$-alkynyl, —S-alkynyl, —S(O)-alkynyl, —$S(O)_2$-alkynyl, —$N(R^6)$-alkynyl, —C(O)—$N(R^{21})$-alkynyl and —$N(R^{21})$—C(O)-alkynyl,
- (10c) aryl, —O-aryl, —C(O)-aryl, —$CO_2$-aryl, —S-aryl, —S(O)-aryl, —$S(O)_2$-aryl, —$N(R^6)$-aryl, —C(O)—$N(R^{21})$-aryl, —$N(R^{21})$—C(O)-aryl, —$N(R^{21})$—C(O)—$N(R^{21})$-aryl, —$N(R^{21})$—S(O)-aryl, —$N(R^{21})$—$S(O)_2$-aryl, —$N(R^{21})$—$S(O)_2$—$N(R^{21})$-aryl, —S(O)—$N(R^{21})$-aryl, —$S(O)_2$—$N(R^{21})$-aryl,
- (11c) heteroaryl, —O-heteroaryl, —C(O)-heteroaryl, —$CO_2$-heteroaryl, —S-heteroaryl, —S(O)-heteroaryl, —$S(O)_2$-heteroaryl, —$N(R^6)$-heteroaryl, —C(O)—$N(R^{21})$-heteroaryl, —$N(R^{21})$—C(O)-heteroaryl, —$N(R^{21})$—C(O)—$N(R^{21})$-heteroaryl, —$N(R^{21})$—S(O)-heteroaryl, —$N(R^{21})$—$S(O)_2$-heteroaryl, —$N(R^{21})$—$S(O)_2$—$N(R^{21})$-heteroaryl, —S(O)—$N(R^{21})$-heteroaryl and —$S(O)_2$—$N(R^{21})$-heteroaryl, wherein said heteroalkyl, said heterocycloalkyl, said heterocycloalkenyl, and said heteroaryl of $R^2$ may be connected through any available carbon or heteroatom, and wherein said alkyl, said heteroalkyl, said cycloalkyl, said heterocycloalkyl, said aryl, said heteroaryl, said alkenyl, said alkynyl, said cycloalkenyl, and said heterocycloalkenyl of $R^2$ are unsubstituted or substituted with one or more groups independently selected from $R^7$.

In another embodiment each $R^2$ is independently selected from:
- (1c) halo, —$NH_2$, —OH, —SH, —$SO_2H$ and $CO_2H$,
- (2c) cycloalkyl, —O-cycloalkyl, —C(O)-cycloalkyl, —S-cycloalkyl and —$N(R^6)$-cycloalkyl,
- (3c) heterocycloalkyl, —O-heterocycloalkyl, —C(O)-heterocycloalkyl, —S-heterocycloalkyl, —S(O)-heterocycloalkyl, —$S(O)_2$-heterocycloalkyl and —$N(R^6)$-heterocycloalkyl, (6c) alkyl, —O-alkyl, —C(O)-alkyl, —CO$_2$-alkyl, —S-alkyl, —S(O)-alkyl, —S(O)$_2$-alkyl, —N(R$^6$)-alkyl, —C(O)—N(R$^{21}$)-alkyl, —N(R$^{21}$)—C(O)-alkyl, —N(R$^{21}$)—C(O)—N(R$^{21}$)-alkyl, —N(R$^{21}$)—S(O)-alkyl, —N(R$^{21}$)—S(O)$_2$-alkyl, —N(R$^{21}$)—S(O)$_2$—N(R$^{21}$)-alkyl, —S(O)—N(R$^{21}$)-alkyl and —S(O)$_2$—N(R$^{21}$)-alkyl, (7c) heteroalkyl, —O-heteroalkyl, —C(O)-heteroalkyl and —S-heteroalkyl, (8c) alkenyl, —O-alkenyl and —C(O)-alkenyl, (10c) aryl, —O-aryl, —C(O)-aryl, —S-aryl, —S(O)-aryl, —S(O)$_2$-aryl, —N(R$^6$)-aryl, —C(O)—N(R$^{21}$)-aryl and —N(R$^{21}$)—C(O)-aryl, (11c) heteroaryl, —O-heteroaryl, —C(O)-heteroaryl, —CO$_2$-heteroaryl, —S-heteroaryl, —S(O)-heteroaryl, —S(O)$_2$-heteroaryl, —N(R$^6$)-heteroaryl, —C(O)—N(R$^{21}$)-heteroaryl and —N(R$^{21}$)—C(O)-heteroaryl, wherein said heteroalkyl, heterocycloalkyl, heterocycloalkenyl, and heteroaryl of R$^2$ may be connected through any available carbon or heteroatom, and wherein said alkyl, heteroalkyl, cycloalkyl, heterocycloalkyl, aryl, heteroaryl, alkenyl, and said heterocycloalkenyl of R$^2$ are unsubstituted or substituted with one to three groups independently selected from R$^7$.

In another embodiment each R$^2$ is independently selected from:

(1c) halo, —NH$_2$, —OH, —SH, —SO$_2$H and CO$_2$H, (2c) cycloalkyl, (3c) heterocycloalkyl, (6c) alkyl, —O-alkyl, —C(O)-alkyl, —S-alkyl, —S(O)$_2$-alkyl, —N(R$^6$)-alkyl, —C(O)—N(R$^{21}$)-alkyl and —N(R$^{21}$)—C(O)-alkyl, (7c) heteroalkyl and —O-heteroalkyl, (8c) alkenyl, (10c) aryl, —O-aryl and —C(O)-aryl, (11c) heteroaryl, —O-heteroaryl, —C(O)-heteroaryl, —S-heteroaryl, —S(O)$_2$-heteroaryl, —N(R$^6$)-heteroaryl, —C(O)—N(R$^{21}$)-heteroaryl and —N(R$^{21}$)—C(O)-heteroaryl, wherein said heteroalkyl, heterocycloalkyl, heterocycloalkenyl, and heteroaryl of R$^2$ may be connected through any available carbon or heteroatom, and wherein said alkyl, heteroalkyl, cycloalkyl, heterocycloalkyl, aryl, heteroaryl, alkenyl, and said heterocycloalkenyl of R$^2$ are unsubstituted or substituted with one to three groups independently selected from R$^7$.

In another embodiment, each R$^2$ is independently selected from:

(1c) halo, —NH$_2$, —OH, —SH, —SO$_2$H, CO$_2$H and cyano, (2c) cycloalkyl, (3c) heterocycloalkyl, (6c) alkyl, —O-alkyl, —C(O)-alkyl, —CO$_2$-alkyl, —S-alkyl, —S(O)-alkyl, —S(O)$_2$-alkyl, —N(R$^6$)-alkyl, —C(O)—N(R$^{21}$)-alkyl, —N(R$^{21}$)—C(O)-alkyl, —N(R$^{21}$)—C(O)—N(R$^{21}$)-alkyl, —N(R$^{21}$)—S(O)-alkyl, —N(R$^{21}$)—S(O)$_2$-alkyl, —N(R$^{21}$)—S(O)$_2$—N(R$^{21}$)-alkyl, —S(O)—N(R$^{21}$)-alkyl and —S(O)$_2$—N(R$^{21}$)-alkyl, (7c) heteroalkyl, (10c) aryl, —O-aryl, —C(O)-aryl, —CO$_2$-aryl, —S-aryl, —S(O)-aryl, —S(O)$_2$-aryl, —N(R$^6$)-aryl, —C(O)—N(R$^{21}$)-aryl and —N(R$^{21}$)—C(O)-aryl, (11c) heteroaryl, —O-heteroaryl, —C(O)-heteroaryl, —CO$_2$-heteroaryl, —S-heteroaryl, —S(O)-heteroaryl, —S(O)$_2$-heteroaryl, —N(R$^6$)-heteroaryl, —C(O)—N(R$^{21}$)-heteroaryl and —N(R$^{21}$)—C(O)-heteroaryl, wherein said heteroalkyl, heterocycloalkyl, and heteroaryl of R$^2$ may be connected through any available carbon or heteroatom, and wherein said alkyl, heteroalkyl, cycloalkyl, heterocycloalkyl, aryl, and heteroaryl of R$^2$ are unsubstituted or substituted with one to three groups independently selected from R$^7$.

In another embodiment, R$^3$ is H.

In another embodiment, R$^3$ is selected from the group consisting of methyl, ethyl, n-propyl, and isopropyl.

In another embodiment, Z is —(C(R$^{11}$)$_2$)—(C(R$^{12}$)(R$^{13}$))$_m$—C(O)OH.

In another embodiment, Z is —(CH$_2$)—(CH(CH$_3$))—C(O)OH.

In another embodiment, Z is —(CH$_2$)—(CH$_2$)—(CH$_2$)—C(O)OH.

In another embodiment, Z is —(CH$_2$)—C(CH$_3$)$_2$—C(O)OH.

In another embodiment, Z is —(CH$_2$)—C(CH$_3$)(OH)—C(O)OH.

In another embodiment, Z is —CH$_2$—CH$_2$—C(O)OH.

In another embodiment, Z is —CH$_2$—CH(OH)—C(O)OH.

In another embodiment, Z is —CH(CH$_3$)—CH$_2$—C(O)OH.

In another embodiment, Z is —C(CH$_3$)$_2$—CH$_2$—C(O)OH.

In another embodiment, Z is —(C(R$^{11}$)$_2$)—(C(R$^{14}$)$_2$)$_n$—, —C(O)OH.

In another embodiment, Z is —CH$_2$—CH(F)—C(O)OH.

In another embodiment, Z is —CH$_2$—CF$_2$—C(O)OH.

In another embodiment, Z is —CH(CH$_3$)—CF$_2$—C(O)OH.

In another embodiment, Z is —CH$_2$—CH$_2$—CF$_2$—C(O)OH.

In another embodiment, Z is

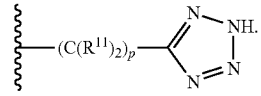

In another embodiment, Z is

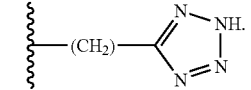

In another embodiment, Z is

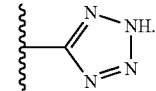

In another embodiment, each R$^6$ is independently selected from:

(1d) hydrogen, (2d) cycloalkyl, (3d) heterocycloalkyl, (6d) alkyl, and (7d) heteroalkyl, In another embodiment, each $R^7$ is independently selected from:
(1e) halo, $-NH_2$, $-OH$, $-SH$, $-SO_2H$, $CO_2H$, $-SF_5$, $-OSF_5$, cyano and $-CHO$,
(2e) cycloalkyl and $-O$-cycloalkyl,
(3e) heterocycloalkyl,
(6e) alkyl, $-O$-alkyl, $-C(O)$-alkyl, $-CO_2$-alkyl, $-S$-alkyl, $-S(O)$-alkyl, $-S(O)_2$-alkyl, $-N(R^6)$-alkyl, $-C(O)-N(R^{21})$-alkyl and $-N(R^{21})-C(O)$-alkyl,
(7e) heteroalkyl,
(10e) aryl, $-O$-aryl, $-C(O)$-aryl, $-CO_2$-aryl, $-S$-aryl, $-S(O)$-aryl, $-S(O)_2$-aryl, $-N(R^6)$-aryl, $-C(O)-N(R^{21})$-aryl and $-N(R^{21})-C(O)$-aryl,
(11e) heteroaryl, $-O$-heteroaryl, $-C(O)$-heteroaryl, $-CO_2$-heteroaryl, $-S$-heteroaryl, $-S(O)$-heteroaryl, $-S(O)_2$-heteroaryl, $-N(R^6)$-heteroaryl, $-C(O)-N(R^{21})$-heteroaryl and $-N(R^{21})-C(O)$-heteroaryl, wherein said heteroalkyl, heterocycloalkyl, and heteroaryl of $R^7$ may be connected through any available carbon or heteroatom.

In another embodiment, each $R^{11}$ is independently selected from H and $C_{1-3}$ alkyl.

In another embodiment, each $R^{12}$ is independently selected from H and $C_{1-3}$ alkyl, and hydroxy-substituted $C_{1-3}$ alkyl;

In another embodiment, each $R^{13}$ is independently selected from H, unsubstituted $C_{1-3}$ alkyl, $C_{1-3}$ alkyl substituted with hydroxyl or $C_{1-3}$ alkoxy.

In another embodiment, each $R^{14}$ is H.

In another embodiment, Q is a moiety selected from the group consisting of:

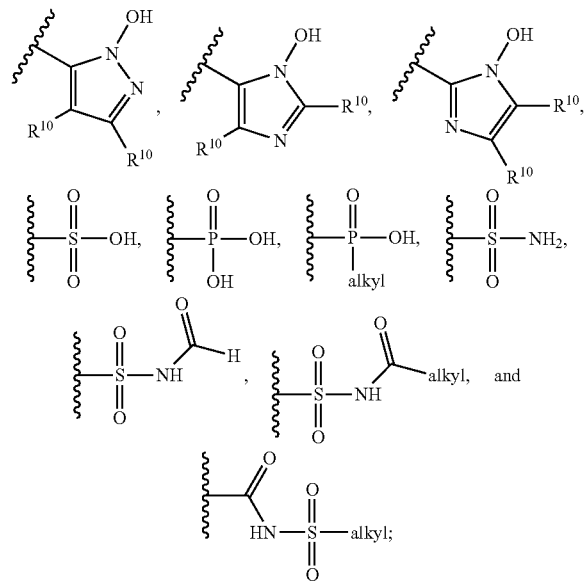

wherein each $R^{10}$ is independently H or $C_{1-3}$ alkyl.
In another embodiment, m is an integer from 0 to 2.
In another embodiment, m is 0.
In another embodiment, m is 1.
In another embodiment, m is 2.
In another embodiment, n is an integer from 0 to 2.
In another embodiment, n is 0.
In another embodiment, n is 1.
In another embodiment, n is 2.
In another embodiment, p is an integer from 0 to 2,
In another embodiment, p is 0.
In another embodiment, p is 1.
In another embodiment, p is 2.

In another embodiment, each $R^4$ is independently selected from the group consisting of: H, $-OH$, $C_{1-3}$ alkyl, $haloC_{1-3}$alkyl, $C_{1-3}$alkoxy, heteroalkyl, cyano-substituted $C_{1-3}$alkyl, hydroxy-substituted $C_{1-3}$alkyl, $C_{3-6}$cycloalkyl, $-O-C_{3-6}$cycloalkyl, heterocycloalkyl, $-O$-heterocycloalkyl, and $-O-C_{1-3}$alkyl-heterocycloalkyl.

In another embodiment, each $R^{5A}$ is independently selected from H, $C_{1-3}$ alkyl, $haloC_{1-3}$alkyl, heteroalkyl, cyano-substituted $C_{1-3}$alkyl, hydroxy-substituted $C_{1-3}$alkyl, $C_{3-6}$cycloalkyl, $C_{1-3}$-alkyl-$C_{3-6}$-cycloalkyl, and heterocycloalkyl, $-C_{1-3}$alkyl-heterocycloalkyl.

In another embodiment, two $R^{5A}$ groups are taken together with the carbon atom to which they are attached to form a carbonyl group, a spiro$C_{3-6}$cycloalkyl group, a spiroheterocycloalkyl group, an oxime group, or a substituted oxime group (said oxime substituents being independently selected from $haloC_{1-3}$alkyl, hydroxyl-substituted $C_{1-3}$alkyl and $C_{3-6}$cycloalkyl).

In another embodiment, each $R^5$ is independently selected from H, $-OH$, $C_{1-3}$alkyl, $haloC_{1-3}$alkyl, $C_{1-3}$alkoxy, heteroalkyl, cyano-substituted $C_{1-3}$alkyl, hydroxy-substituted $C_{1-3}$alkyl, $C_{3-6}$cycloalkyl, $C_{1-3}$alkyl-$C_{3-6}$cycloalkyl, $-O-C_{3-6}$cycloalkyl, $-O-C_{1-3}$alkyl-$C_{3-6}$cycloalkyl, and heterocycloalkyl, $-C_{1-3}$alkyl-heterocycloalkyl, $-O$-heterocycloalkyl and $-O-C_{1-3}$alkyl-heterocycloalkyl.

In another embodiment, two $R^5$ groups bound to the same carbon atom are taken together with the carbon atom to which they are attached to form a carbonyl group, a spiro$C_{3-6}$cycloalkyl group, a spiroheterocycloalkyl group, an oxime group, or a substituted oxime group (said oxime substituents being independently selected from $C_{1-3}$alkyl, $haloC_{1-3}$alkyl, hydroxyl-substituted $C_{1-3}$alkyl and $C_{3-6}$cycloalkyl).

In another embodiment, q is 0.
In another embodiment, q is 1.
In another embodiment, q is 2.
In another embodiment, r is 0.
In another embodiment, r is 1.
In another embodiment, r is 2.
In another embodiment, s is 0.
In another embodiment, s is 1.
In another embodiment, s is 2.

A subset of compounds of the invention is represented by Formula (A):

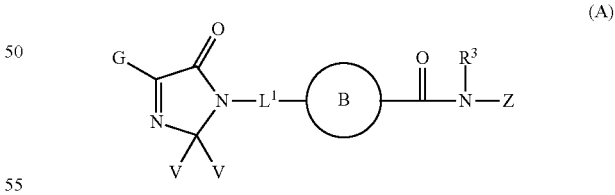

(A)

and includes pharmaceutically acceptable salts of said compounds, wherein:

each V is independently selected from the group consisting of: alkyl and cycloalkyl, each being unsubstituted or substituted with one to three groups independently selected from:
(1) halo, $-NH_2$, $-OH$, $-SH$, $-SO_2H$, $CO_2H$, $-SF_5$, $-OSF_5$, cyano and $-CHO$;
(2) cycloalkyl, $-O$-cycloalkyl, $-C(O)$-cycloalkyl, $-CO_2$-cycloalkyl, $-S$-cycloalkyl, $-S(O)$-cycloalkyl, $-S(O)_2$-cycloalkyl, $-N(R^1)$-cycloalkyl, $-C(O)-N(R^{21})$-cycloalkyl, $-N(R^{21})-C(O)$-cycloalkyl, $-N(R^{21})-C$ (O)—N(R$^{21}$)-cycloalkyl, —N(R$^{21}$)—S(O)-cycloalkyl, —N(R$^{21}$)—S(O)$_2$-cycloalkyl, —N(R$^{21}$)—S(O)$_2$—N(R$^{21}$)-cycloalkyl, —S(O)—N(R$^{21}$)-cycloalkyl and —S(O)$_2$—N(R$^{21}$)-cycloalkyl;

(3) heterocycloalkyl, —O-heterocycloalkyl, —C(O)-heterocycloalkyl, —CO$_2$-heterocycloalkyl, —S-heterocycloalkyl, —S(O)-heterocycloalkyl, —S(O)$_2$-heterocycloalkyl, —N(R$^1$)-heterocycloalkyl, —C(O)—N(R$^{21}$)-heterocycloalkyl, —N(R$^{21}$)—C(O)-heterocycloalkyl, —N(R$^{21}$)—C(O)—N(R$^{21}$)-heterocycloalkyl, —N(R$^{21}$)—S(O)-heterocycloalkyl, —N(R$^{21}$)—S(O)$_2$-heterocycloalkyl, —N(R$^{21}$)—S(O)$_2$—N(R$^{21}$)-heterocycloalkyl, —S(O)—N(R$^{21}$)-heterocycloalkyl, and —S(O)$_2$—N(R$^{21}$)-heterocycloalkyl;

(4) cycloalkenyl, —O-cycloalkenyl, —C(O)-cycloalkenyl, —CO$_2$-cycloalkenyl, —S-cycloalkenyl, —S(O)-cycloalkenyl, —S(O)$_2$-cycloalkenyl, —N(R$^1$)-cycloalkenyl, —C(O)—N(R$^{21}$)-cycloalkenyl, —N(R$^{21}$)—C(O)-cycloalkenyl, —N(R$^{21}$)—C(O)—N(R$^{21}$)-cycloalkenyl, —N(R$^{21}$)—S(O)-cycloalkenyl, —N(R$^{21}$)—S(O)$_2$-cycloalkenyl, —N(R$^{21}$)—S(O)$_2$—N(R$^{21}$)— cycloalkenyl, —S(O)—N(R$^{21}$)-cycloalkenyl and —S(O)$_2$—N(R$^{21}$)-cycloalkenyl;

(5) heterocycloalkenyl, —O-heterocycloalkenyl, —C(O)-heterocycloalkenyl, —CO$_2$-heterocycloalkenyl, —S-heterocycloalkenyl, —S(O)-heterocycloalkenyl, —S(O)$_2$-heterocycloalkenyl, —N(R$^1$)-heterocycloalkenyl, —C(O)—N(R$^{21}$)-heterocycloalkenyl, and —N(R$^{21}$)—C(O)-heterocycloalkenyl, —N(R$^{21}$)—C(O)—N(R$^{21}$)-heterocycloalkenyl, —N(R$^{21}$)—S(O)-heterocycloalkenyl, —N(R$^{21}$)—S(O)$_2$-heterocycloalkenyl, —N(R$^{21}$)—S(O)$_2$—N(R$^{21}$)-heterocycloalkenyl, —S(O)—N(R$^{21}$)-heterocycloalkenyl and —S(O)$_2$—N(R$^{21}$)-heterocycloalkenyl;

(6) alkyl, —O-alkyl, —C(O)-alkyl, —CO$_2$-alkyl, —S-alkyl, —S(O)-alkyl, —S(O)$_2$-alkyl, —N(R$^1$)-alkyl, —C(O)—N(R$^{21}$)-alkyl, —N(R$^{21}$)—C(O)-alkyl, —N(R$^{21}$)—C(O)—N(R$^{21}$)-alkyl, —N(R$^{21}$)—S(O)-alkyl, —N(R$^{21}$)—S(O)$_2$-alkyl, —N(R$^{21}$)—S(O)$_2$—N(R$^{21}$)-alkyl, —S(O)—N(R$^{21}$)-alkyl and —S(O)$_2$—N(R$^{21}$)-alkyl;

(7) heteroalkyl, —O-heteroalkyl, —C(O)-heteroalkyl, —CO$_2$-heteroalkyl, —S-heteroalkyl, —S(O)-heteroalkyl, —S(O)$_2$-heteroalkyl, —N(R$^1$)-heteroalkyl, —C(O)—N(R$^{21}$)-heteroalkyl, —N(R$^{21}$)—C(O)-heteroalkyl, —N(R$^{21}$)—C(O)—N(R$^{21}$)-heteroalkyl, —N(R$^{21}$)—S(O)-heteroalkyl, —N(R$^{21}$)—S(O)$_2$-heteroalkyl, —N(R$^{21}$)—S(O)$_2$—N(R$^{21}$)-heteroalkyl, —S(O)—N(R$^{21}$)-heteroalkyl and —S(O)$_2$—N(R$^{21}$)-heteroalkyl;

(8) alkenyl, —O-alkenyl, —C(O)-alkenyl, —CO$_2$-alkenyl, —S-alkenyl, —S(O)-alkenyl, —S(O)$_2$-alkenyl, —N(R$^1$)-alkenyl, —C(O)—N(R$^{21}$)-alkenyl, —N(R$^{21}$)—C(O)-alkenyl, —N(R$^{21}$)—C(O)—N(R$^{21}$)-alkenyl, —N(R$^{21}$)—S(O)-alkenyl, —N(R$^{21}$)—S(O)$_2$-alkenyl, —N(R$^{21}$)—S(O)$_2$—N(R$^{21}$)-alkenyl, —S(O)—N(R$^{21}$)-alkenyl and —S(O)$_2$—N(R$^{21}$)-alkenyl;

(9) alkynyl, —O-alkynyl, —C(O)-alkynyl, —CO$_2$-alkynyl, —S-alkynyl, —S(O)-alkynyl, —S(O)$_2$-alkynyl, —N(R$^1$)-alkynyl, —C(O)—N(R$^{21}$)-alkynyl, —N(R$^{21}$)—C(O)-alkynyl, —N(R$^{21}$)—C(O)—N(R$^{21}$)-alkynyl, —N(R$^{21}$)—S(O)-alkynyl, —N(R$^{21}$)—S(O)$_2$-alkynyl; —N(R$^{21}$)—S(O)$_2$—N(R$^{21}$)-alkynyl, —S(O)—N(R$^{21}$)-alkynyl and —S(O)$_2$—N(R$^{21}$)-alkynyl;

(10) aryl, —O-aryl, —C(O)-aryl, —CO$_2$-aryl, —S-aryl, —S(O)-aryl, —S(O)$_2$-aryl, —N(R$^1$)-aryl, —C(O)—N(R$^{21}$)-aryl, —N(R$^{21}$)—C(O)-aryl, —N(R$^{21}$)—C(O)—N(R$^{21}$)-aryl, —N(R$^{21}$)—S(O)-aryl, —N(R$^{21}$)—S(O)$_2$-aryl, —N(R$^{21}$)—S(O)$_2$—N(R$^{21}$)-aryl, —S(O)—N(R$^{21}$)-aryl and —S(O)$_2$—N(R$^{21}$)-aryl;

(11) heteroaryl, —O-heteroaryl, —C(O)-heteroaryl, —CO$_2$-heteroaryl, —S-heteroaryl, —S(O)-heteroaryl, —S(O)$_2$-heteroaryl, —N(R$^1$)-heteroaryl, —C(O)—N(R$^{21}$)-heteroaryl, —N(R$^{21}$)—C(O)-heteroaryl, —N(R$^{21}$)—C(O)—N(R$^{21}$)-heteroaryl, —N(R$^{21}$)—S(O)-heteroaryl, —N(R$^{21}$)—S(O)$_2$-heteroaryl, —N(R$^{21}$)—S(O)$_2$—N(R$^{21}$)-heteroaryl, —S(O)—N(R$^{21}$)-heteroaryl and —S(O)$_2$—N(R$^{21}$)-heteroaryl;

wherein said heteroalkyl of (7), heterocycloalkyl of (3), heterocycloalkenyl of (5), and heteroaryl of (11) are connected through any available carbon atom or heteroatom;

and wherein said alkyl, heteroalkyl, cycloalkyl, heterocycloalkyl, aryl, heteroaryl, alkenyl, alkynyl, cycloalkenyl, and heterocycloalkenyl of (1) through (11) are unsubstituted or substituted with one or more groups independently selected from R$^2$;

G is selected from the group consisting of:
(1a) hydrogen, halo, —NH$_2$ and —OH;
(2a) cycloalkyl and —N(R$^1$)-cycloalkyl;
(3a) heterocycloalkyl and —N(R$^1$)-heterocycloalkyl;
(6a) alkyl and —N(R$^1$)-alkyl;
(7a) heteroalkyl;
(10a) aryl and —N(R$^1$)-aryl;
(11a) heteroaryl and —N(R$^1$)-heteroaryl;

wherein said heterocycloalkyl and heteroaryl of G are connected through any available carbon or heteroatom, and wherein said alkyl, cycloalkyl, heterocycloalkyl, aryl, and heteroaryl, of G are unsubstituted or substituted with one to three groups independently selected from R$^2$;

L$^1$ represents —(C(R$^{5A}$)$_2$)—(C(R$^5$)$_2$)$_s$—;

ring B is phenyl;

R$^3$ is H;

Z is selected from the group consisting of:
—(C(R$^{11}$)$_2$)—(C(R$^{12}$R$^{13}$))$_m$—C(O)OH, —(C(R$^{11}$)$_2$)—(C(R$^{14}$)$_2$)$_n$—C(O)OH,
—(C(R$^{11}$)$_2$)—(C(R$^{12}$R$^{13}$))$_m$C(O)Oalkyl, —(C(R$^{11}$)$_2$)—(C(R$^{14}$)$_2$)$_n$—C(O)Oalkyl and

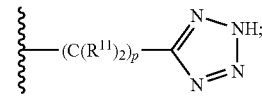

each R$^1$ is independently selected from:
(1b) hydrogen,
(2b) cycloalkyl,
(3b) heterocycloalkyl,
(6b) alkyl,
(7b) heteroalkyl;
(10b) aryl, and
(11b) heteroaryl, wherein said heteroalkyl, heterocycloalkyl, heterocycloalkenyl, and heteroaryl of R$^1$ may be connected through any available carbon or heteroatom, and wherein said alkyl, cycloalkyl, heterocycloalkyl, aryl, and heteroaryl of R$^1$ are unsubstituted or substituted with one to three groups independently selected from R$^2$;

each R$^2$ is independently selected from:
(1c) halo, —NH$_2$, —OH, —SH, —SO$_2$H and CO$_2$H,
(2c) cycloalkyl and —O-cycloalkyl;
(3c) heterocycloalkyl and —O-heterocycloalkyl;
(6e) alkyl and —O-alkyl,
(7c) heteroalkyl and —O-heteroalkyl,
(8c) alkenyl,
(10c) aryl, —O-aryl and —C(O)-aryl, (11c) heteroaryl, —O-heteroaryl, —C(O)-heteroaryl, —S-heteroaryl, —S(O)$_2$-heteroaryl, —N(R$^6$)-heteroaryl, —C(O)—N(R$^{21}$)-heteroaryl and —N(R$^{21}$)—C(O)-heteroaryl, wherein said heteroalkyl, heterocycloalkyl, heterocycloalkenyl, and heteroaryl of R$^2$ may be connected through any available carbon or heteroatom, and wherein said alkyl, heteroalkyl, cycloalkyl, heterocycloalkyl, aryl, heteroaryl, alkenyl, and said heterocycloalkenyl of R$^2$ are unsubstituted or substituted with one to three groups independently selected from R$^7$;

each R$^7$ is independently selected from:
(1e) halo,
(2e) cycloalkyl and —O-cycloalkyl,
(3e) heterocycloalkyl and —O-heterocycloalkyl;
(6e) alkyl and —O-alkyl,
(7e) heteroalkyl and —O-heteroalkyl;
(10e) aryl and —O-aryl,
(11e) heteroaryl and —O-heteroaryl, wherein said heteroalkyl, heterocycloalkyl, and heteroaryl of R$^7$ may be connected through any available carbon or heteroatom;

each R$^{11}$ is independently selected from H and C$_{1-3}$alkyl;
each R$^{12}$ is independently selected from H and C$_{1-3}$alkyl, and hydroxy-substituted C$_{1-3}$alkyl;
each R$^{13}$ is independently selected from H, unsubstituted C$_{1-3}$alkyl, C$_{1-3}$alkyl substituted with hydroxyl and C$_{1-3}$alkoxy;
each R$^{14}$ is H; and p, s, m and n each independently represent 0-2.

Another subset of compounds of the invention is represented by Formula (A):

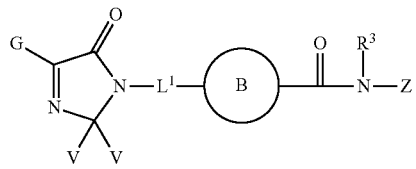

(A)

and includes pharmaceutically acceptable salts of said compounds, wherein:

each V is independently selected from the group consisting of: C$_{1-6}$alkyl and cycloalkyl;

G represents a phenyl group optionally substituted with 1-3 groups selected from halo, C$_{1-3}$alkyl, C$_{1-3}$alkoxy, haloC$_{1-3}$alkyl and haloC$_{1-3}$alkoxy, or with one phenyl ring which is optionally substituted with 1-3 halo atoms;

L$^1$ represents —(C(R$^{5A}$)$_2$)—(C(R$^5$)$_2$)$_s$—; wherein s is 0-1, each R$^{5A}$ represents H, C$_{1-6}$alkyl or C$_{3-6}$cycloalkyl, and when present, each R$^5$ represents H;

ring B is phenyl;
R$^3$ is H;
Z is selected from the group consisting of: CH$_2$CH$_2$CO$_2$H and

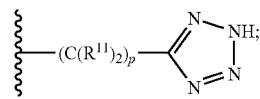

wherein p is 0-2 and when present each R$^{11}$ is H.

Examples of compounds that are of interest are set forth below in Table 1.

TABLE 1

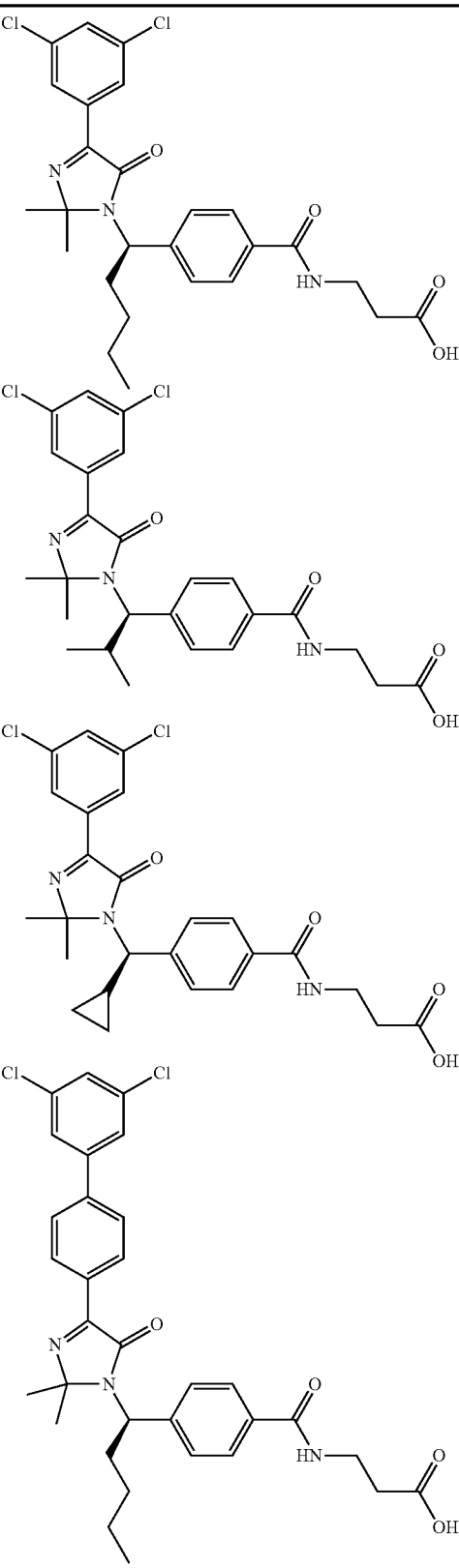

TABLE 1-continued
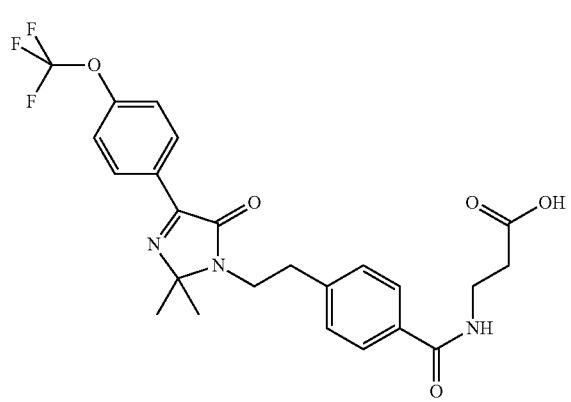 [SMILES: CC1(C)N=C(c2ccc(OC(F)(F)F)cc2)C(=O)N1CCc1ccc(C(=O)NCCC(=O)O)cc1]
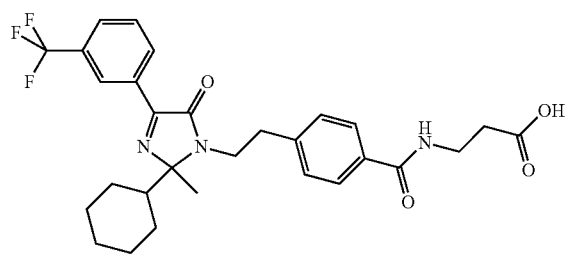 [SMILES: CC1(C2CCCCC2)N=C(c2cccc(C(F)(F)F)c2)C(=O)N1CCc1ccc(C(=O)NCCC(=O)O)cc1]
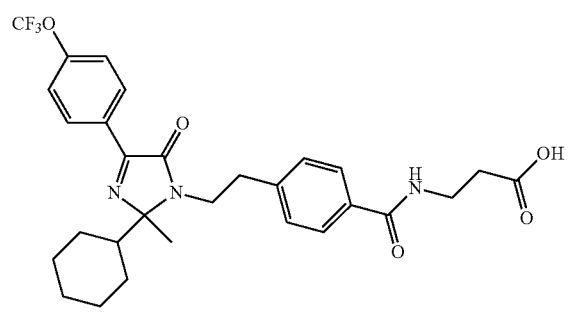
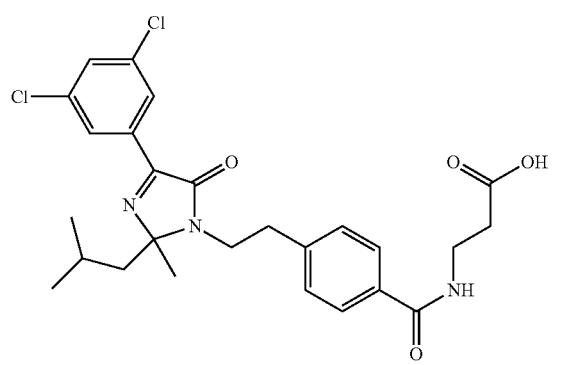 [SMILES: CC(C)CC1(C)N=C(c2cc(Cl)cc(Cl)c2)C(=O)N1CCc1ccc(C(=O)NCCC(=O)O)cc1]
TABLE 1-continued
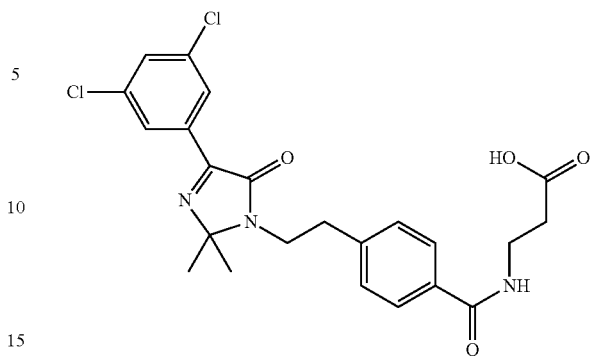
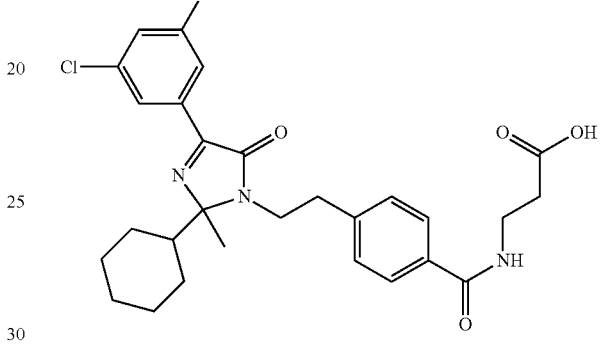
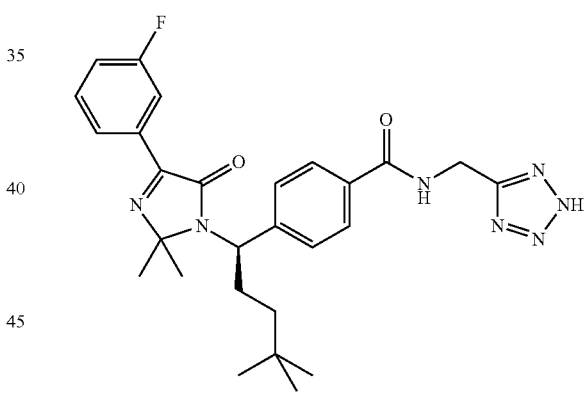
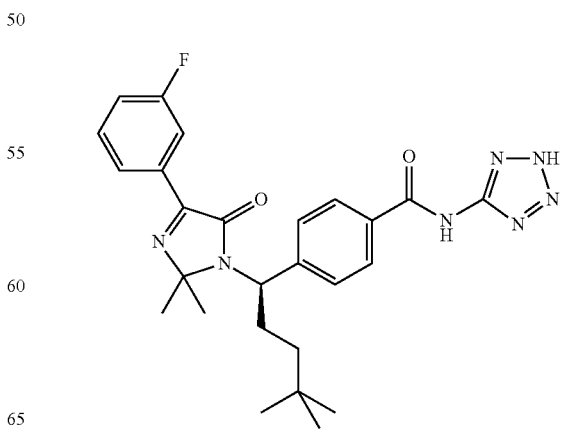

TABLE 1-continued
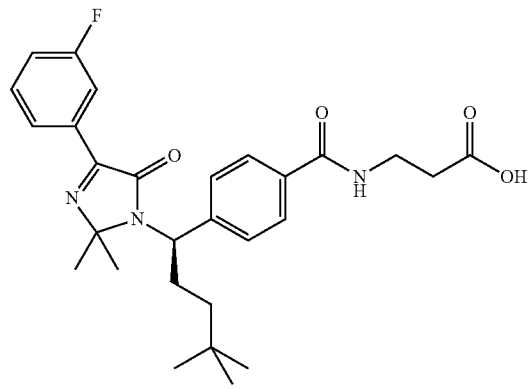 [SMILES: CC(C)(C)CC[C@H](c1ccc(C(=O)NCCC(=O)O)cc1)N1C(=O)C(c2cccc(F)c2)=NC1(C)C]
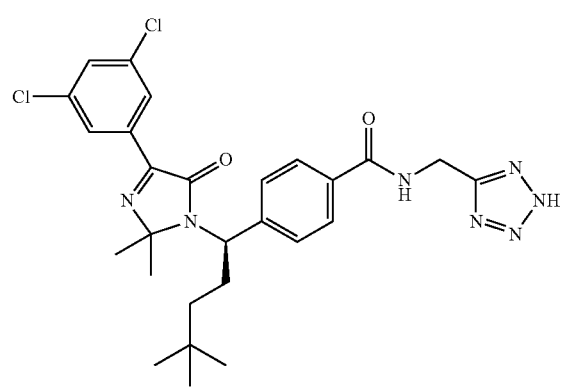 [SMILES: CC(C)(C)CC[C@H](c1ccc(C(=O)NCc2nn[nH]n2)cc1)N1C(=O)C(c2cc(Cl)cc(Cl)c2)=NC1(C)C]
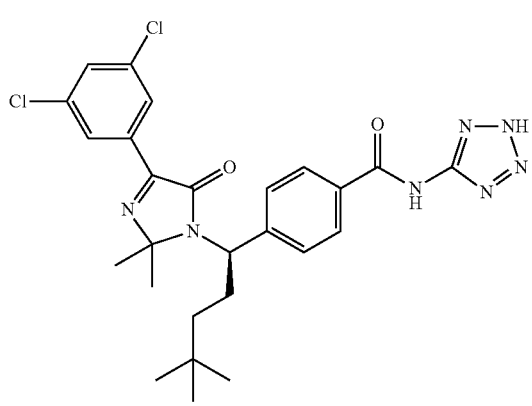 [SMILES: CC(C)(C)CC[C@H](c1ccc(C(=O)Nc2nn[nH]n2)cc1)N1C(=O)C(c2cc(Cl)cc(Cl)c2)=NC1(C)C]
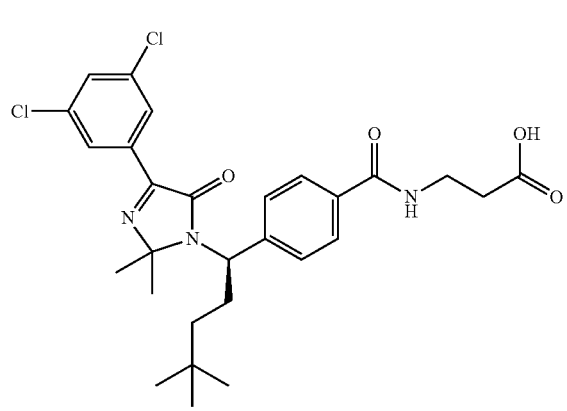 [SMILES: CC(C)(C)CC[C@H](c1ccc(C(=O)NCCC(=O)O)cc1)N1C(=O)C(c2cc(Cl)cc(Cl)c2)=NC1(C)C]
TABLE 1-continued
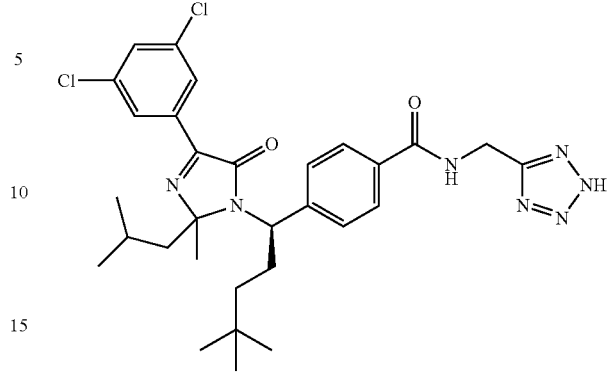
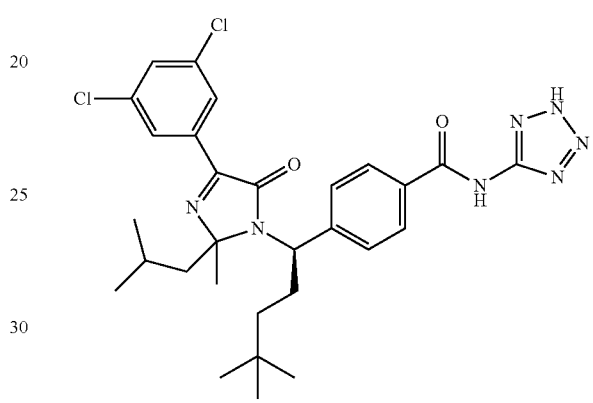
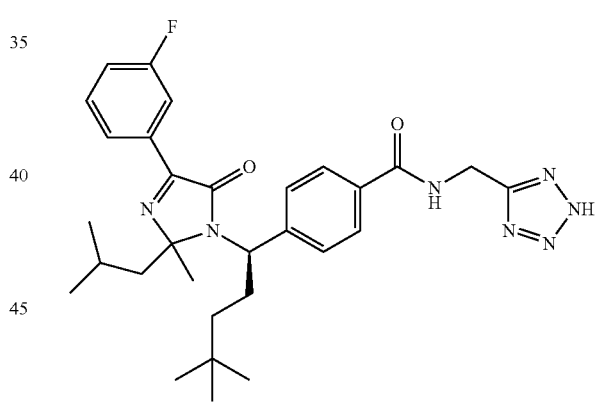
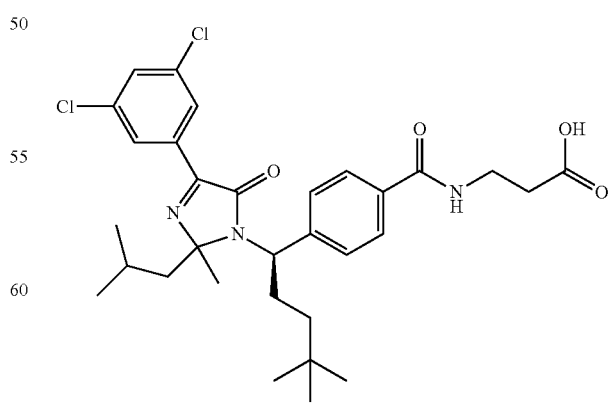
as well as the pharmaceutically acceptable salts thereof.

In the various embodiments described herein, variables of each of the general formulas not explicitly defined in the context of the respective formula are as defined in Formula (A).

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

"Mammal" means humans and other mammalian animals.

A "patient" is a human or non-human mammal. In one embodiment, a patient is a human. In another embodiment, a patient is a non-human mammal, including, but not limited to, a monkey, baboon, mouse, rat, horse, dog, cat or rabbit. In another embodiment, a patient is a companion animal, including but not limited to a dog, cat, rabbit, horse or ferret. In one embodiment, a patient is a dog. In another embodiment, a patient is a cat.

The term "obesity" as used herein, refers to a patient being overweight and having a body mass index (BMI) of 25 or greater. In one embodiment, an obese patient has a BMI of 25 or greater. In another embodiment, an obese patient has a BMI from 25 to 30. In another embodiment, an obese patient has a BMI greater than 30. In still another embodiment, an obese patient has a BMI greater than 40.

The term "impaired glucose tolerance" (IGT) as used herein, is defined as a two-hour glucose level of 140 to 199 mg per dL (7.8 to 11.0 mmol) as measured using the 75-g oral glucose tolerance test. A patient is said to be under the condition of impaired glucose tolerance when he/she has an intermediately raised glucose level after 2 hours, wherein the level is less than would qualify for type 2 diabetes mellitus.

The term "impaired fasting glucose" (IFG) as used herein, is defined as a fasting plasma glucose level of 100 to 125 mg/dL; normal fasting glucose values are below 100 mg per dL.

The term "effective amount" as used herein, refers to an amount of Compound of Formula (I) and/or an additional therapeutic agent, or a composition thereof that is effective in producing the desired therapeutic, ameliorative, inhibitory or preventative effect when administered to a patient suffering from a Condition. In the combination therapies of the present invention, an effective amount can refer to each individual agent or to the combination as a whole, wherein the amounts of all agents administered are together effective, but wherein the component agent of the combination may not be present individually in an effective amount.

"Halogen" means fluorine, chlorine, bromine, or iodine. Preferred are fluorine, chlorine and bromine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being as described herein or independently selected from the group consisting of halo, alkyl, haloalkyl, spirocycloalkyl, aryl, cycloalkyl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

The term "haloalkyl" as used herein, refers to an alkyl group, as defined above, wherein one or more of the alkyl group's hydrogen atoms have been independently replaced with —F, —Cl, —Br or —I. Non-limiting illustrative examples of haloalkyl groups include —CH$_2$F, —CHF$_2$, —CF$_3$, —CH$_2$CHF$_2$, —CH$_2$CF$_3$, —CCl$_3$, —CHCl$_2$, —CH$_2$Cl, and —CH$_2$CHCl$_2$.

"Heteroalkyl" means an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical. Suitable such heteroatoms include O, S, S(O), S(O)$_2$, and —NH—, —N(alkyl)-. Non-limiting examples include ethers, thioethers, amines, hydroxymethyl, 3-hydroxypropyl, 1,2-dihydroxyethyl, 2-methoxyethyl, 2-aminoethyl, 2-dimethylaminoethyl, and the like. The bond to the parent moiety may be through either an available carbon or heteroatom.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. Further non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$— and —CH$_2$CH(CH$_3$)CH$_2$—. In one embodiment, an alkylene group has from 1 to about 6 carbon atoms. In another embodiment, an alkylene group is branched. In another embodiment, an alkylene group is linear. More generally, the suffix "ene" on alkyl, aryl, heterocycloalkyl, etc. indicates a divalent moiety, e.g., —CH$_2$CH$_2$— is ethylene, and

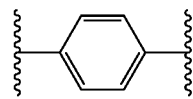

is para-phenylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Alkenylene" means a Bifunctional group obtained by removal of a hydrogen from an alkenyl group that is defined above. Non-limiting examples of alkenylene include —CH=CH—, —C(CH$_3$)=CH—, and —CH=CHCH$_2$—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The bond to the parent moiety may be through an available carbon or nitrogen atom.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like. Further non-limiting examples of cycloalkyl include the following:

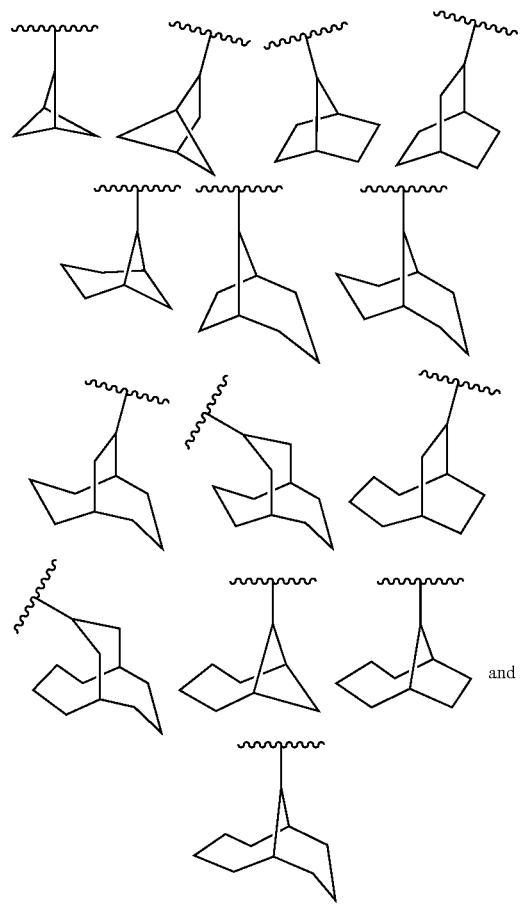

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH— in a heterocyclyl ring may exist protected such as, for example, as an —N(Boc)-, —N(CBz)-, —N(Tos)- group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Thus, the term "oxide,"

when it appears in a definition of a variable in a general structure described herein, refers to the corresponding N-oxide, S-oxide, or S,S-dioxide. Non-limiting examples of suitable monocyclic heterocyclyl rings include piperidinyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes rings wherein =O replaces two available hydrogens on the same carbon atom (i.e., heterocyclyl includes rings having a carbonyl group in the ring). Such =O groups may be referred to herein as "oxo." Example of such moiety is pyrrolidinone (or pyrrolidone):

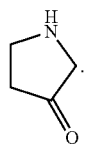

"Heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined herein. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom (i.e., heterocyclyl includes rings having a carbonyl group in the ring). Example of such moiety is pyrrolidenone (or pyrrolone):

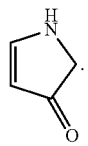

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

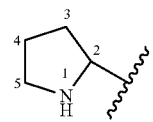

there is no —OH attached directly to carbons marked 2 and 5.

It should also be noted that tautomeric forms such as, for example, the moieties:

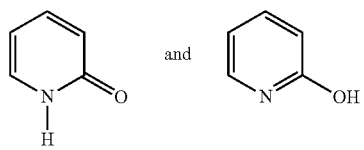 [SMILES: O=c1cccc[nH]1 ; Oc1ccccn1]

are considered equivalent in certain embodiments of this invention.

It should be understood that for hetero-containing functional groups described herein, e.g., heterocycloalkyl, heterocycloalkenyl, heteroalkyl, heteroaryl, and arylheterocycloalkyl (e.g., benzo-fused heterocycloalkyl), the bond to the parent moiety can be through an available carbon or heteroatom (e.g., nitrogen atom).

"Arylcycloalkyl" (or "arylfused cycloalkyl") means a group derived from a fused aryl and cycloalkyl as defined herein. Preferred arylcycloalkyls are those wherein aryl is phenyl (which may be referred to as "benzofused") and cycloalkyl consists of about 5 to about 6 ring atoms. The arylcycloalkyl can be optionally substituted as described herein. Non-limiting examples of suitable arylcycloalkyls include indanyl (a benzofused cycloalkyl) and 1,2,3,4-tetrahydronaphthyl and the like. The bond to the parent moiety is through a non-aromatic carbon atom.

"Arylheterocycloalkyl" (or "arylfused heterocycloalkyl") means a group derived from a fused aryl and heterocycloalkyl as defined herein. Preferred arylheterocycloalkyls are those wherein aryl is phenyl (which may be referred to as "benzofused") and heterocycloalkyl consists of about 5 to about 6 ring atoms. The arylheterocycloalkyl can be optionally substituted, and/or contain the oxide or oxo, as described herein. Non-limiting examples of suitable arylfused heterocycloalkyls include:

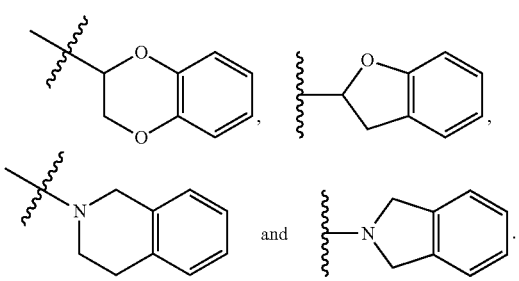

The bond to the parent moiety is through a non-aromatic carbon or nitrogen atom.

It is also understood that the terms "arylfused aryl", "arylfused cycloalkyl", "arylfused cycloalkenyl", "arylfused heterocycloalkyl", arylfused heterocycloalkenyl", "arylfused heteroaryl", "cycloalkylfused aryl", "cycloalkylfused cycloalkyl", "cycloalkylfused cycloalkenyl", "cycloalkylfused heterocycloalkyl", "cycloalkylfused heterocycloalkenyl", "cycloalkylfused heteroaryl, "cycloalkenylfused aryl", "cycloalkenylfused cycloalkyl", "cycloalkenylfused cycloalkenyl", "cycloalkenylfused heterocycloalkyl", "cycloalkenylfused heterocycloalkenyl", "cycloalkenylfused heteroaryl", "heterocycloalkylfused aryl", "heterocycloalkylfused cycloalkyl", "heterocycloalkylfused cycloalkenyl", "heterocycloalkylfused heterocycloalkyl", "heterocycloalkylfused heterocycloalkenyl", "heterocycloalkylfused heteroaryl", "heterocycloalkenylfused aryl", "heterocycloalkenylfused cycloalkyl", "heterocycloalkenylfused cycloalkenyl", "heterocycloalkenylfused heterocycloalkyl", "heterocycloalkenylfused heterocycloalkenyl", "heterocycloalkenylfused heteroaryl", "heteroarylfused aryl", "heteroarylfused cycloalkyl", "heteroarylfused cycloalkenyl", "heteroarylfused heterocycloalkyl", "heteroarylfused heterocycloalkenyl", and "heteroarylfused heteroaryl" are similarly represented by the combination of the groups aryl, cycloalkyl, cycloalkenyl, heterocycloalkyl, heterocycloalkenyl, and heteroaryl, as previously described. Any such groups may be unsubstituted or substituted with one or more ring system substituents at any available position as described herein.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl. The term (and similar terms) may be written as "arylalkyl-" to indicate the point of attachment to the parent moiety.

Similarly, "heteroarylalkyl", "cycloalkylalkyl", "cycloalkenylalkyl", "heterocycloalkylalkyl", "heterocycloalkenylalkyl", etc., mean a heteroaryl, cycloalkyl, cycloalkenyl, heterocycloalkyl, heterocycloalkenyl, etc. as described herein bound to a parent moiety through an alkyl group. Preferred groups contain a lower alkyl group. Such alkyl groups may be straight or branched, unsubstituted and/or substituted as described herein.

Similarly, "arylfused arylalkyl-", arylfused cycloalkylalkyl-, etc., means an arylfused aryl group, arylfused cycloalkyl group, etc. linked to a parent moiety through an alkyl group. Preferred groups contain a lower alkyl group. Such alkyl groups may be straight or branched, unsubstituted and/or substituted as described herein.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkylether" means a non-aromatic ring of 3 to 7 members comprising an oxygen atom and 2 to 7 carbon atoms. Ring carbon atoms can be substituted, provided that substituents adjacent to the ring oxygen do not include halo or substituents joined to the ring through an oxygen, nitrogen or sulfur atom.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl, adamantylpropyl, and the like.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclylalkyl" (or "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenylalkyl" means a heterocyclenyl moiety as defined above linked via an alkyl moiety (defined above) to a parent core.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Cyanoalkyl" means a NC-alkyl- group in which alkyl is as previously defined. Preferred cyanoalkyls contain lower alkyl. Non-limiting examples of suitable cyanoalkyl groups include cyanomethyl and 2-cyanoethyl.

"Acyl" means an H—C(O)—, alkyl-C(O)— or cycloalkyl-C(O)—, group in which the various groups are as previously described. The bond to the parent moiety is through the carbonyl carbon. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl carbon. Non-limiting examples of suitable groups include benzoyl and 1-naphthoyl.

"Heteroaroyl" means an heteroaryl-C(O)— group in which the heteroaryl group is as previously described. The bond to the parent moiety is through the carbonyl carbon. Non-limiting examples of suitable groups include pyridoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkyoxyalkyl" means a group derived from an alkoxy and alkyl as defined herein. The bond to the parent moiety is through the alkyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" (or "arylalkyloxy") means an aralkyl-O— group (an arylalkyl-O— group) in which the aralkyl group is as previously described. Non-limiting examples of suitable aralkyloxy groups include benzyloxy and 1- or 2-naphthalenemethoxy. The bond to the parent moiety is through the ether oxygen.

"Arylalkenyl" means a group derived from an aryl and alkenyl as defined herein. Preferred arylalkenyls are those wherein aryl is phenyl and the alkenyl consists of about 3 to about 6 atoms. The arylalkynyl can be optionally substituted by one or more substituents. The bond to the parent moiety is through a non-aromatic carbon atom.

"Arylalkynyl" means a group derived from a aryl and alkenyl as defined herein. Preferred arylalkynyls are those wherein aryl is phenyl and the alkynyl consists of about 3 to about 6 atoms. The arylalkynyl can be optionally substituted by one or more substituents. The bond to the parent moiety is through a non-aromatic carbon atom.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl carbon.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl carbon.

"Aralkoxycarbonyl" means an aralkyl-O—C(O)— group. Non-limiting example of a suitable aralkoxycarbonyl group is benzyloxycarbonyl. The bond to the parent moiety is through the carbonyl carbon.

"Alkylsulfonyl" means an alkyl-S($O_2$)— group. Preferred groups are those in which the alkyl group is lower alkyl. The bond to the parent moiety is through the sulfur atom of the sulfonyl.

"Arylsulfonyl" means an aryl-S($O_2$)— group. The bond to the parent moiety is through the sulfur atom of the sulfonyl.

"Spirocycloalkyl" means a cycloalkyl group attached to a parent moiety at a single carbon atom. Non-limiting examples of spirocycloalkyl wherein the parent moiety is a cycloalkyl include spiro [2.5] octane, spiro [2.4] heptane, etc. Non-limiting examples of spirocycloalkyl wherein the parent moiety is an The alkyl moiety linking fused ring systems (such as the alkyl moiety in heteroarylfused heteroarylalkyl-) may optionally be substituted with spirocycloalkyl or other groups as described herein. Non-limiting spirocycloalkyl groups include spirocyclopropyl, spriorcyclobutyl, spirocycloheptyl, and spirocyclohexyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl- moiety or the like includes substitution on any ring portion and/or on the alkyl portion of the group.

When a variable appears more than once in a group, e.g., $R^8$ in —$N(R^8)_2$, or a variable appears more than once in a structure presented herein such as Formula (I), the variables can be the same or different.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. Examples of "one or more" include one to six, one to four, one to three, one or two, and one substituent. With respect to the compositions and methods comprising the use of "at least one compound of the invention, e.g., of Formula (I)," one to three compounds of the invention, e.g., of Formula (I) can be administered at the same time, preferably one.

Compounds of the invention may contain one or more rings having one or more ring system substituents. "Ring system substituent" means a substituent attached to an aromatic or non-aromatic ring system which, for example, replaces an available hydrogen on the ring system. Ring system substituents may be the same or different, each being as described herein or independently selected from the group consisting of alkyl, alkenyl, alkynyl, haloalkyl, heteroalkyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—$NH_2$, —C(=NH)—$NH_2$, —C(=NH)—NH(alkyl), $Y_1Y_2N$—, $Y_1Y_2N$-alkyl-, $Y_1Y_2NC(O)$—, $Y_1Y_2NSO_2$— and —$SO_2NY_1Y_2$, wherein $Y_1$ and $Y_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moieties are rings such as heteroaryl, cycloalkyl, cycloalkenyl, heterocycloalkyl, and heterocycloalkenyl rings. Additional non-limiting examples include methylene dioxy, ethylenedioxy, —C($CH_3$)$_2$— and the like which form moieties such as, for example:

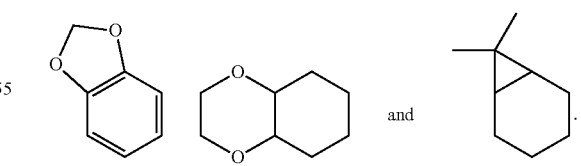

As used herein, the term "composition" is intended to encompass a product comprising the specified ingredients in the specified amounts, as well as any product which results, directly or indirectly, from combination of the specified ingredients in the specified amounts.

The line ---- as a bond generally indicates a mixture of, or either of, the possible isomers, e.g. containing (R)- and (S)-stereochemistry. For example:

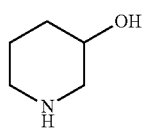

means containing both

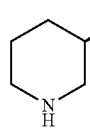 and 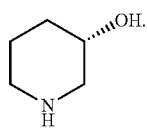.

The wavy line ～～ as used herein, indicates a point of attachment to the rest of the compound. For example, each wavy line in the following structure:

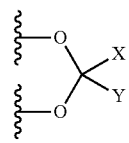

indicates a point of attachment to the core structure, as described herein.

Lines drawn into the ring systems, such as, for example:

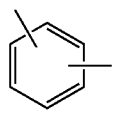

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

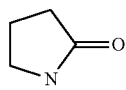

In this specification, where there are multiple oxygen and/or sulfur atoms in a ring system, there cannot be any adjacent oxygen and/or sulfur present in said ring system.

It is noted that the carbon atoms for compounds of the invention may be replaced with 1 to 3 silicon atoms so long as all valency requirements are satisfied.

As well known in the art, a bond drawn from a particular atom wherein no moiety is depicted at the terminal end of the bond indicates a methyl group bound through that bond to the atom, unless stated otherwise. For example:

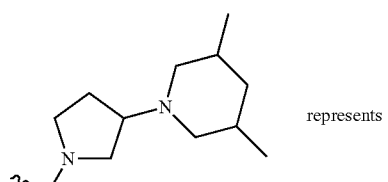 represents

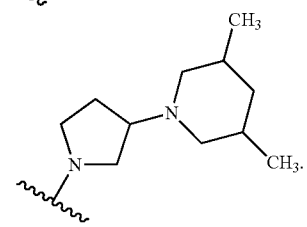

In one embodiment, a compound or compounds of the invention is/are in isolated or purified form.

The term "purified" "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1999), Wiley, New York.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-(C1-C2)alkyl and piperidino-, pyrrolidino- or morpholino$(C_2-C_3)$ alkyl, and the like.

Similarly, if a compound of the invention contains an alcohol functional group, a prodrug can be formed by the replacement of the hydrogen atom of the alcohol group with a group such as, for example, $(C_1-C_6)$alkanoyloxymethyl, 1-(($C_1-C_6$) alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1-C_6$)alkyl)$_2$ or glycosyl (the radical resulting from the removal of a hydroxyl group of the hemiacetal form of a carbohydrate), and the like.

If a compound of the invention incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1$-$C_4)$ alkyl and Y$^3$ is $(C_1-C_6)$alkyl, carboxy $(C_1-C_6)$alkyl, amino$(C_1-C_4)$alkyl or mono-N- or di-N,N—$(C_1-C_6)$alkylaminoalkyl, —C(Y$^4$)Y$^5$ wherein Y$^4$ is H or methyl and Y$^5$ is mono-N- or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

One or more compounds of the invention may optionally be converted to a solvate. Preparation of solvates is generally known. Thus, for example, M. Caira et al., *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of the invention can form salts which are also within the scope of this invention. Reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the invention may be formed, for example, by reacting a compound of the invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of the invention, and salts, solvates, esters and prodrugs thereof, may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of a chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of the invention (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of the invention can generally be prepared by following procedures analogous to those disclosed in the Schemes and/or in the Examples hereinbelow, by substituting an appropriate isotopically labelled reagent for a non-isotopically labelled reagent.

Suitable hydrogen atoms of the compounds of the invention which may be deuterated include one or more hydrogen atoms of the lower alkyl group(s) and/or hydroxyl-substituted lower alkyl groups of $R^5$. Additional suitable hydrogen atoms which may be deuterated include, in each of Formula (A), Formula (I), Formula (III), Formula (IV), Formula (V), and/or Formula (VI), one or more hydrogen atoms of the groups $R^{11}$, $R^{12}$ and/or $R^{13}$ of Z.

Polymorphic forms of the compounds of the invention, and of the salts, solvates, esters and prodrugs of the compounds of the invention, are intended to be included in the present invention. For example, the term "compounds of formula (A)" as used herein includes the solvates, esters, prodrugs, tautomers and isomers of the depicted genus.

In another embodiment, the present invention provides a pharmaceutical composition comprising a compound of the invention described above in combination with a pharmaceutically acceptable carrier.

In another embodiment, the present invention provides a method for inhibiting glucagon receptors comprising exposing an effective amount of a compound or a composition comprising a compound of the invention to glucagon receptors. In one embodiment, said glucagon receptors are part of a glucagon receptor assay. Non-limiting examples of such assays include glucagon receptor assays and glucagon-stimulated intracellular cAMP formation assays such as those described herein. In one embodiment, said glucagon receptors are expressed in a population of cells. In one embodiment, the population of cells is in in vitro. In one embodiment, the population of cells is in ex vivo. In one embodiment, the population of cells is in a patient.

Methods of Treatment, Compositions, and Combination Therapy

In another embodiment, the present invention provides a method of treating type 2 diabetes mellitus in a patient in need of such treatment comprising administering to said patient a compound of the invention or a composition comprising a compound of the invention in an amount effective to treat type 2 diabetes mellitus.

In another embodiment, the present invention provides a method of delaying the onset of type 2 diabetes mellitus in a patient in need of such treatment comprising administering to said patient a compound of the invention or a composition comprising a compound of the invention in an amount effective to delay the onset of type 2 diabetes mellitus.

In another embodiment, the present invention provides a method of treating hyperglycemia, diabetes, or insulin resistance in a patient in need of such treatment comprising administering to said patient a compound of the invention, or a composition comprising a compound of the invention, in an amount that is effective to treat hyperglycemia, diabetes, or insulin resistance.

In another embodiment, the present invention provides a method of treating non-insulin dependent diabetes mellitus in a patient in need of such treatment comprising administering to said patient an anti-diabetic effective amount of a compound of the invention or a composition comprising an effective amount of a compound of the invention.

In another embodiment, the present invention provides a method of treating obesity in a patient in need of such treatment comprising administering to said patient a compound of the invention or a composition comprising a compound of the invention in an amount that is effective to treat obesity.

In another embodiment, the present invention provides a method of treating one or more conditions associated with Syndrome X (also known as metabolic syndrome, metabolic syndrome X, insulin resistance syndrome, Reaven's syndrome) in a patient in need of such treatment comprising administering to said patient a compound of the invention or a composition comprising an effective amount of a compound of the invention in an amount that is effective to treat Syndrome X.

In another embodiment, the present invention provides a method of treating a lipid disorder in a patient in need of such treatment comprising administering to said patient a compound of the invention, or a composition comprising a compound of the invention, in an amount that is effective to treat said lipid disorder. Non-limiting examples of such lipid disorders include: dyslipidemia, hyperlipidemia, hypertriglyceridemia, hypercholesterolemia, low HDL and high LDL, and metabolic syndrome.

In another embodiment, the present invention provides a method of treating atherosclerosis in a patient in need of such treatment comprising administering to said patient a compound of the invention or a composition comprising a compound of the invention, in an amount effective to treat atherosclerosis.

In another embodiment, the present invention provides a method of delaying the onset of, or reducing the risk of developing, atherosclerosis in a patient in need of such treatment comprising administering to said patient a compound of the invention or a composition comprising a compound of the invention, in an amount effective to delay the onset of, or reduce the risk of developing, atherosclerosis.

In another embodiment, the present invention provides a method of treating a condition or a combination of conditions selected from hyperglycemia, low glucose tolerance, insulin resistance, obesity, abdominal obesity, lipid disorders, dyslipidemia, hyperlipidemia, hypertriglyceridemia, hypercholesterolemia, low HDL levels, high LDL levels, atherosclerosis, atherosclerosis and its sequelae, vascular restenosis, pancreatitis, neurodegenerative disease, retinopathy, nephropathy, neuropathy, Syndrome X and other conditions where insulin resistance is a component, in a patient in need thereof, comprising administering to said patient a compound of the invention, or a composition comprising a compound of the invention, in an amount that is effective to treat said condition or conditions.

In another embodiment, the present invention provides a method of delaying the onset of a condition or a combination of conditions selected from hyperglycemia, low glucose tolerance, insulin resistance, obesity, abdominal obesity, lipid disorders, dyslipidemia, hyperlipidemia, hypertriglyceridemia, hypercholesterolemia, low HDL levels, high LDL levels, atherosclerosis, atherosclerosis and its sequelae, vascular restenosis, pancreatitis, neurodegenerative disease, retinopathy, nephropathy, neuropathy, Syndrome X and other conditions where insulin resistance is a component, in a patient in need thereof, comprising administering to said patient a compound of the invention, or a composition comprising a compound of the invention, in an amount that is effective to delay the onset said condition or conditions.

In another embodiment, the present invention provides a method of reducing the risk of developing a condition or a combination of conditions selected from hyperglycemia, low glucose tolerance, insulin resistance, obesity, abdominal obesity, lipid disorders, dyslipidemia, hyperlipidemia, hypertriglyceridemia, hypercholesterolemia, low HDL levels, high LDL levels, atherosclerosis, atherosclerosis and its sequelae, vascular restenosis, pancreatitis, neurodegenerative disease, retinopathy, nephropathy, neuropathy, Syndrome X and other conditions where insulin resistance or hyperglycemia is a component, in a patient in need thereof, comprising administering to said patient a compound of the invention, or a composition comprising a compound of the invention, in an amount that is effective to reduce the risk of developing said condition or conditions.

In another embodiment, the present invention provides a method of treating a condition selected from type 2 diabetes mellitus, hyperglycemia, low glucose tolerance, insulin resistance, obesity, abdominal obesity, lipid disorders, dyslipidemia, hyperlipidemia, hypertriglyceridemia, hypercholesterolemia, low HDL levels, high LDL levels, atherosclerosis, atherosclerosis and its sequelae, vascular restenosis, pancreatitis, neurodegenerative disease, retinopathy, nephropathy, neuropathy, Syndrome X and other conditions where insulin resistance is a component, in a patient in need thereof, comprising administering to said patient effective amounts of a compound of the invention and one or more additional active agents.

Non-limiting examples of such additional active agents include the following:

DPP-IV inhibitors. Non-limiting examples of DPP-IV inhibitors include alogliptin (Takeda), saxagliptin (Brystol-Myers Squibb), sitagliptin (Januvia™, Merck), vildagliptin (Galvus™ Novartis), denagliptin (GlaxoSmithKline), ABT-279 and ABT-341 (Abbott), ALS-2-0426 (Alantos), ARI-2243 (Arisaph), BI-A and BI-B (Boehringer Ingelheim), SYR-322 (Takeda), compounds disclosed in U.S. Pat. No. 6,699,871, MP-513 (Mitsubishi), DP-893 (Pfizer), RO-0730699 (Roche) and combinations thereof. Non-limiting examples of such combinations include Janumet™, a combination of sitagliptin/metformin HCl (Merck).

Insulin sensitizers. Non-limiting examples of insulin sensitizers include PPAR agonists and biguanides. Non-limiting examples of PPAR agonists include glitazone and thiaglitazone agents such as rosiglitazone, rosiglitazone maleate (AVANDIA™, GlaxoSmithKline), pioglitazone, pioglitazone hydrochloride (ACTOS™, Takeda), ciglitazone and MCC-555 (Mitstubishi Chemical Co.), troglitazone and englitazone. Non-limiting example of biguanides include phenformin, metformin, metformin hydrochloride (such as GLUCOPHAGE®, Bristol-Myers Squibb), metformin hydrochloride with glyburide (such as GLUCOVANCE™, Bristol-Myers Squibb) and buformin. Other non-limiting examples of insulin sensitizers include PTP-1 B inhibitors; and glucokinase activators, such as miglitol, acarbose, and voglibose.

Insulin and insulin mimetics. Non-limiting examples of orally administrable insulin and insulin containing compositions include AL-401 (Autoimmune), and the compositions disclosed in U.S. Pat. Nos. 4,579,730; 4,849,405; 4,963,526; 5,642,868; 5,763,396; 5,824,638; 5,843,866; 6,153,632; 6,191,105; and International Publication No. WO 85/05029, each of which is incorporated herein by reference.

Sulfonylureas and other insulin secretagogues. Non-limiting examples of sulfonylureas and other secretagogues include glipizide, tolbutamide, glyburide, glimepiride, chlorpropamide, acetohexamide, gliamilide, gliclazide, glibenclamide, tolazamide, GLP-1, GLP-1 mimetics, exendin, GIP, secretin, nateglinide, meglitinide, glibenclamide, and repaglinide. Non-limiting examples of GLP-1 mimetics include Byetta™ (exenatide), Liraglutinide, CJC-1131 (ConjuChem), exenatide-LAR (Amylin), BIM-51077 (Ipsen/LaRoche), ZP-10 (Zealand Pharmaceuticals), and compounds disclosed in International Publication No. WO 00/07617.

Glucosidase inhibitors and alpha glucosidase inhibitors.

Glucagon receptor antagonists other than compounds of the invention.

Hepatic glucose output lowering agents other than a glucagon receptor antagonist. Non-limiting examples of hepatic glucose output lowering agents include Glucophage and Glucophage XR.

An antihypertensive agent. Non-limiting examples of antihypertensive agents include beta-blockers and calcium channel blockers (for example diltiazem, verapamil, nifedipine, amlopidine, and mybefradil), ACE inhibitors (for example captopril, lisinopril, enalapril, spirapril, ceranopril, zefenopril, fosinopril, cilazopril, and quinapril), AT-1 receptor antagonists (for example losartan, irbesartan, and valsartan), renin inhibitors and endothelin receptor antagonists (for example sitaxsentan).

A meglitinide. Non-limiting examples of meglitinides useful in the present methods for treating diabetes include repaglinide and nateglinide.

An agent that blocks or slows the breakdown of starches or sugars in vivo. Non-limiting examples of antidiabetic agents that slow or block the breakdown of starches and sugars in vivo include alpha-glucosidase inhibitors and certain peptides for increasing insulin production; Alpha-glucosidase inhibitors (which help the body to lower blood sugar by delaying the digestion of ingested carbohydrates, thereby resulting in a smaller rise in blood glucose concentration following meals). Non-limiting examples of alpha-glucosidase inhibitors include acarbose; miglitol; camiglibose; certain polyamines as disclosed in WO 01/47528 (incorporated herein by reference); and voglibose.

Peptides for increasing insulin production. Non-limiting examples of suitable peptides for increasing insulin production including amlintide (CAS Reg. No. 122384-88-7, Amylin); pramlintide, exendin, certain compounds having Glucagon-like peptide-1 (GLP-1) agonistic activity as disclosed in WO 00/07617 (incorporated herein by reference).

A histamine $H_3$ receptor antagonist. Non-limiting examples of histamine $H_3$ receptor antagonist agents include the following compound:

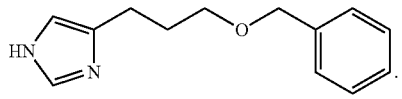 [SMILES: c1ccc(COCCCc2c[nH]cn2)cc1]

A sodium glucose uptake transporter 2 (SGLT-2) inhibitor. Non-limiting examples of SGLT-2 inhibitors useful in the present methods include dapagliflozin and sergliflozin, AVE2268 (Sanofi-Aventis) and T-1095 (Tanabe Seiyaku).

PACAP (pituitary adenylate cyclase activating polypeptide agonists) and PACAP mimetics.

Cholesterol lowering agents. Non-limiting examples of cholesterol lowering agents include HMG-CoA reducatase inhibitors, sequestrants, nicotinyl alcohol, nicotinic acid and salts thereof, PPAR alpha agonists, PPAR alpha/gamma dual agonists, inhibitors of cholesterol absorption (such as ezetimibe (Zetia®)), combinations of HMG-CoA reductase inhibitors and cholesterol absorption agents (such as Vytorin®), acyl CoA: cholesterol acyltransferase inhibitors, anti-oxidants, LXR modulators, and CETP (cholesterolester transfer protein) inhibitors such as Torcetrapib™ (Pfizer) and Anacetrapib™ (Merck).

Agents capable of raising serum HDL cholesterol levels. Non-limiting examples include niacin (vitamin B-3), such as Niaspan™ (Kos). Niacin may be administered alone or optionally combined with one or more additional active agents such as: niacin/lovastatin (Advicor™, Abbott), niacin/simvastatin (Simcor™, Abbott), and/or niacin/aspirin.

PPAR delta agonists.

Antiobesity agents. Non-limiting examples of anti-obesity agents useful in the present methods for treating diabetes include a 5-HT2C agonist, such as lorcaserin; a neuropeptide Y antagonist; an MCR4 agonist; an MCH receptor antagonist; a protein hormone, such as leptin or adiponectin; an AMP kinase activator; and a lipase inhibitor, such as orlistat.

Ileal bile acid transporter inhibitors.

Anti-inflammatory agents, such as NSAIDs. Non-limiting examples of NSAIDS include a salicylate, such as aspirin, amoxiprin, benorilate or diflunisal; an arylalkanoic acid, such as diclofenac, etodolac, indometacin, ketorolac, nabumetone, sulindac or tolmetin; a 2-arylpropionic acid (a "profen"), such as ibuprofen, carprofen, fenoprofen, flurbiprofen, loxoprofen, naproxen, tiaprofenic acid or suprofen; a fenamic acid, such as mefenamic acid or meclofenamic acid; a pyrazolidine derivative, such as phenylbutazone, azapropazone, metamizole or oxyphenbutazone; a coxib, such as celecoxib, etoricoxib, lumiracoxib or parecoxib; an oxicam, such as piroxicam, lornoxicam, meloxicam or tenoxicam; or a sulfonanilide, such as nimesulide.

Anti-pain medications, including NSAIDs as discussed above, and opiates. Non-limiting examples of opiates include an anilidopiperidine, a phenylpiperidine, a diphenylpropylamine derivative, a benzomorphane derivative, an oripavine derivative and a morphinane derivative. Additional illustrative examples of opiates include morphine, diamorphine, heroin, buprenorphine, dipipanone, pethidine, dextromoramide, alfentanil, fentanyl, remifentanil, methadone, codeine, dihydrocodeine, tramadol, pentazocine, vicodin, oxycodone, hydrocodone, percocet, percodan, norco, dilaudid, darvocet or lorcet.

Antidepressants. Non-limiting examples of tricyclic antidepressants useful in the present methods for treating pain include amitryptyline, carbamazepine, gabapentin or pregabalin.

Protein tyrosine phosphatase-1B (PTP-1B) inhibitors.

CB1 antagonists/inverse agonists. Non-limiting examples of CB1 receptor antagonists and inverse agonists include rimonabant and those disclosed in WO03/077847A2, published Sep. 25, 2003, WO05/000809, published Jan. 6, 2005, and WO2006/060461, published Jun. 8, 2006.

In another embodiment, the present invention provides a method of treating a condition selected from hypercholesterolemia, atherosclerosis, low HDL levels, high LDL levels, hyperlipidemia, hypertriglyceridemia, and dyslipidemia, in a patient in need of such treatment, comprising administering to the patient a therapeutically effective amount or amounts of a compound of the invention, or a composition comprising a compound of the invention, and an HMG-CoA reductase inhibitor.

In another embodiment, the present invention provides a method of treating a condition selected from hypercholesterolemia, atherosclerosis, low HDL levels, high LDL levels, hyperlipidemia, hypertriglyceridemia, and dyslipidemia, in a patient in need of such treatment, comprising administering to the patient a therapeutically effective amount or amounts of a compound of the invention, or a composition comprising a compound of the invention, and an HMG-CoA reductase inhibitor, wherein the HMG-CoA reductase inhibitor is a statin.

In another embodiment, the present invention provides a method of treating a condition selected from hypercholesterolemia, atherosclerosis, low HDL levels, high LDL levels, hyperlipidemia, hypertriglyceridemia, and dyslipidemia, in a patient in need of such treatment, comprising administering to the patient a therapeutically effective amount or amounts of a compound of the invention, or a composition comprising a compound of the invention, and an HMG-CoA reductase inhibitor, wherein the HMG-CoA reductase inhibitor is a statin selected from lovastatin, simvastatin, pravastatin, fluvastatin, atorvastatin, itavastatin, ZD-4522, and rivastatin.

In another embodiment, the present invention provides a method of reducing the risk of developing, or delaying the onset of, a condition selected from hypercholesterolemia, atherosclerosis, low HDL levels, high LDL levels, hyperlipidemia, hypertriglyceridemia, and dyslipidemia, in a patient in need of such treatment, comprising administering to the patient a therapeutically effective amount or amounts of a compound of the invention, or a composition comprising a compound of the invention, and an HMG-CoA reductase inhibitor.

In another embodiment, the present invention provides a method of reducing the risk of developing, or delaying the onset of, a condition selected from hypercholesterolemia, atherosclerosis, low HDL levels, high LDL levels, hyperlipidemia, hypertriglyceridemia, and dyslipidemia, in a patient in need of such treatment, comprising administering to the patient a therapeutically effective amount or amounts of a compound of the invention, or a composition comprising a compound of the invention, and an HMG-CoA reductase inhibitor, wherein the HMG-CoA reductase inhibitor is a statin.

In another embodiment, the present invention provides a method of reducing the risk of developing, or delaying the onset of, a condition selected from hypercholesterolemia, atherosclerosis, low HDL levels, high LDL levels, hyperlipidemia, hypertriglyceridemia, and dyslipidemia, in a patient in need of such treatment, comprising administering to the patient a therapeutically effective amount or amounts of a compound of the invention, or a composition comprising a compound of the invention, and an HMG-CoA reductase inhibitor, wherein the HMG-CoA reductase inhibitor is a statin selected from lovastatin, simvastatin, pravastatin, fluvastatin, atorvastatin, itavastatin, ZD-4522, and rivastatin.

In another embodiment, the present invention provides a method of reducing the risk of developing, or delaying the onset of atherosclerosis, high LDL levels, hyperlipidemia, and dyslipidemia, in a patient in need of such treatment, comprising administering to the patient a therapeutically effective amount or amounts of a compound of the invention, or a composition comprising a compound of the invention, and a cholesterol absorption inhibitor, optionally in further combination with a statin.

In another embodiment, the present invention provides a method of reducing the risk of developing, or delaying the onset of atherosclerosis, high LDL levels, hyperlipidemia, and dyslipidemia, in a patient in need of such treatment, comprising administering to the patient a therapeutically effective amount or amounts of a compound of the invention, or a composition comprising a compound of the invention, and a cholesterol absorption inhibitor, optionally in further combination with one or more statins, wherein the cholesterol absorption inhibitor is selected from ezetimibe, ezetimibe/simvastatin combination (Vytorin®), and a stanol.

In another embodiment, the present invention provides a pharmaceutical composition comprising (1) a compound according to the invention; (2) one or more compounds or agents selected from DPP-IV inhibitors, insulin sensitizers, insulin and insulin mimetics, a sulfonylurea, an insulin secretagogue, a glucosidase inhibitor, an alpha glucosidase inhibitor, a glucagon receptor antagonists other than a compound of the invention, a hepatic glucose output lowering agent other than a glucagon receptor antagonist, an antihypertensive agent, a meglitinide, an agent that blocks or slows the breakdown of starches or sugars in vivo, an alpha-glucosidase inhibitor, a peptide capable of increasing insulin production, a histamine $H_3$ receptor antagonist, a sodium glucose uptake transporter 2 (SGLT-2) inhibitor, a peptide that increases insulin production, a GIP cholesterol lowering agent, a PACAP, a PACAP mimetic, a PACAP receptor 3 agonist, a cholesterol lowering agent, a PPAR delta agonist, an antiobesity agent, an ileal bile acid transporter inhibitor, an anti-inflammatory agent, an anti-pain medication, an antidepressant, a protein tyrosine phosphatase-1B (PTP-1B) inhibitor, a CB1 antagonist, and a CB1 inverse agonist; and (3) one or more pharmaceutically acceptable carriers.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts).

In one embodiment, the one or more compounds of the invention is administered during at time when the additional therapeutic agent(s) exert their prophylactic or therapeutic effect, or vice versa.

In another embodiment, the one or more compounds of the invention and the additional therapeutic agent(s) are administered in doses commonly employed when such agents are used as monotherapy for treating a condition.

In another embodiment, the one or more compounds of the invention and the additional therapeutic agent(s) are administered in doses lower than the doses commonly employed when such agents are used as monotherapy for treating a condition.

In still another embodiment, the one or more compounds of the invention and the additional therapeutic agent(s) act synergistically and are administered in doses lower than the doses commonly employed when such agents are used as monotherapy for treating a condition.

In one embodiment, the one or more compounds of the invention and the additional therapeutic agent(s) are present in the same composition. In one embodiment, this composition is suitable for oral administration. In another embodiment, this composition is suitable for intravenous administration.

The one or more compounds of the invention and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of one or more compounds of the invention and the additional therapeutic agent(s) may inhibit the resistance of a condition to the agent(s).

In one embodiment, when the patient is treated for diabetes, a diabetic complication, impaired glucose tolerance or impaired fasting glucose, the other therapeutic is an antidiabetic agent which is not a compound of the invention. In another embodiment, when the patient is treated for pain, the other therapeutic agent is an analgesic agent which is not a compound of the invention.

In another embodiment, the other therapeutic agent is an agent useful for reducing any potential side effect of a compound of the invention. Non-limiting examples of such potential side effects include nausea, vomiting, headache, fever, lethargy, muscle aches, diarrhea, general pain, and pain at an injection site.

In one embodiment, the other therapeutic agent is used at its known therapeutically effective dose. In another embodiment, the other therapeutic agent is used at its normally prescribed dosage. In another embodiment, the other therapeutic agent is used at less than its normally prescribed dosage or its known therapeutically effective dose.

The doses and dosage regimen of the other agents used in the combination therapies of the present invention for the treatment or prevention of a condition described herein can be determined by the attending clinician, taking into consideration the approved doses and dosage regimen in the package insert; the age, sex and general health of the patient; and the type and severity of the viral infection or related disease or disorder. When administered in combination, the compound(s) of the invention and the other agent(s) for treating diseases or conditions listed above can be administered simultaneously or sequentially. This is particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the one or more compounds of the invention and the additional therapeutic agent(s) can, when administered as combination therapy, range from about 0.1 to about 2000 mg per day, although variations will necessarily occur depending on the target of the therapy, the patient and the route of administration. In one embodiment, the dosage is from about 0.2 to about 100 mg/day, administered in a single dose or in 2-4 divided doses. In another embodiment, the dosage is from about 1 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses.

As indicated above, in one embodiment, the invention provides compositions comprising an effective amount of one or more compounds of the invention or a pharmaceutically acceptable salt, solvate, ester or prodrug thereof, and a pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

In one embodiment, the compound of the invention is administered orally.

In another embodiment, the compound of the invention is administered parenterally.

In another embodiment, the compound of the invention is administered intravenously.

In one embodiment, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation is from about 0.1 to about 2000 mg. Variations will necessarily occur depending on the target of the therapy, the patient and the route of administration. In one embodiment, the unit dose dosage is from about 0.2 to about 1000 mg. In another embodiment, the unit dose dosage is from about 1 to about 500 mg. In another embodiment, the unit dose dosage is from about 1 to about 100 mg/day. In still another embodiment, the unit dose dosage is from about 1 to about 50 mg. In yet another embodiment, the unit dose dosage is from about 1 to about 10 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 75 mg/day, in two to four divided doses.

When the invention comprises a combination of at least one compound of the invention and an additional therapeutic agent, the two active components may be co-administered simultaneously or sequentially, or a single pharmaceutical composition comprising at least one compound of the invention and an additional therapeutic agent in a pharmaceutically acceptable carrier can be administered. The components of the combination can be administered individually or together in any conventional dosage form such as capsule, tablet, powder, cachet, suspension, solution, suppository, nasal spray, etc. The dosage of the additional therapeutic agent can be determined from published material, and may range from about 1 to about 1000 mg per dose. In one embodiment, when used in combination, the dosage levels of the individual components are lower than the recommended individual dosages because of the advantageous effect of the combination.

Thus, the term "pharmaceutical composition" is also intended to encompass both the bulk composition and individual dosage units comprised of more than one (e.g., two) pharmaceutically active agents such as, for example, a compound of the present invention and an additional agent selected from the various the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

In one embodiment, the components of a combination therapy regime are to be administered simultaneously, they can be administered in a single composition with a pharmaceutically acceptable carrier.

In another embodiment, when the components of a combination therapy regime are to be administered separately or sequentially, they can be administered in separate compositions, each containing a pharmaceutically acceptable carrier.

The components of the combination therapy can be administered individually or together in any conventional dosage form such as capsule, tablet, powder, cachet, suspension, solution, suppository, nasal spray, etc.

Kits

In one embodiment, the present invention provides a kit comprising a effective amount of one or more compounds of the invention, or a pharmaceutically acceptable salt or solvate thereof, and a pharmaceutically acceptable carrier, vehicle or diluent.

In another aspect the present invention provides a kit comprising an amount of one or more compounds of the invention, or a pharmaceutically acceptable salt or solvate thereof, and an amount of at least one additional therapeutic agent described above, wherein the combined amounts are effective for treating or preventing a condition described herein in a patient.

When the components of a combination therapy regime are to are to be administered in more than one composition, they can be provided in a kit comprising in a single package, one container comprising a compound of the invention in pharmaceutically acceptable carrier, and one or more separate containers, each comprising one or more additional therapeutic agents in a pharmaceutically acceptable carrier, with the active components of each composition being present in amounts such that the combination is therapeutically effective.

EXPERIMENTALS

A number of references have been cited herein, the entire disclosures of which are incorporated herein by reference.

Abbreviations used in the experimentals may include the following:

| ACN | Acetonitrile | AcOH | Acetic acid |
|---|---|---|---|
| Aq | Aqueous | Bn | Benzyl |
| BOC | tert-Butoxycarbonyl | BOC$_2$O | BOG Anhydride |
| Bu | Butyl | C. (or ° C.) | degrees Celsius |
| Cbz | benzyloxycarbonyl | DBU | 1,8-Diazabicyclo[5.4.0]undec-7-ene |
| DCM | Dichloromethane | DIPEA | Diisopropylethylamine |
| DMA | N,N-Dimethylacetamide | DMAP | 4-Dimethylaminopyridine |
| DME | 1,2-dimethoxyethane | DMF | Dimethylformamide |
| DMSO | Dimethyl sulfoxide | DPPF | 1,1'-(bis-diphenylphosphino)ferrocene |

-continued

| | | | |
|---|---|---|---|
| EDCI | 1-(3-Dimethylaminopropyl)-3-ethylcarbodiimide hydrochloride | EDC | 1-(3-Dimethylaminopropyl)-3-ethylcarbodiimide hydrochloride |
| EI | Electron ionization | Eq | Equivalents |
| Et | Ethyl | EtOAc | Ethyl acetate |
| EtOH | Ethanol | g | grams |
| h, hr | hours | $^1$H | proton |
| HATU | N,N,N',N'-Tetramethyl-O-(7-Azabenzotriazol-1-yl)uronium hexafluorophosphate | Hex | hexanes |
| HOBT | 1-Hydroxybenzotriazole | HOBT•H$_2$O | 1-Hydroxybenzotriazole hydrate |
| HOTS | para-toluene sulfonic acid (see also TsOH) | HOTS•H$_2$O | para-toluene sulfonic acid hydrate (see also TsOH•H$_2$O) |
| HMPA | hexamethylphosphoramide | HPLC | High pressure liquid chromatography |
| IPA | isopropanol, 2-propanol | LDA | lithium diisopropylamide |
| M | Molar | mmol | milimolar |
| mCPBA | meta-Chloroperoxy benzoic acid | Me | Methyl |
| MeCN | Acetonitrile | MeOH | Methanol |
| min | Minutes | mg | Milligrams |
| MHZ | Megahertz | mL (or ml) | Milliliter |
| Mol sieves | molecular sieves | N | normal |
| NMR | Nuclear Magnetic Resonance | MS | Mass Spectroscopy |
| NBS | N-Bromosuccinimide | NMM | N-Methylmorpholine |
| NMP | 1-methyl-2-pyrrolidone | ON | Overnight |
| PTLC | Preparative thin layer chromatography | PyBrOP | Bromo-tris-pyrrolidino-phosphonium hexafluorophosphate |
| PyBOP | (Benzotriazol-1-yloxy)tripyrrolidinophosphonium hexa-fluorophosphate | Pyr | Pyridine |
| Quant | quantitative | RT or rt | Room temperature |
| sat (or sat. or sat'd.) | Saturated | SFC | supercritical fluid chromatography |
| sgc | Silica gel 60 chromatography | SiO$_2$ | Silica gel |
| tBOC | tert-Butoxycarbonyl | t-Bu | tert-butyl |
| TEA | Triethylamine | Tf | Trifluoromethane sulfonyl |
| TFA | Trifluoroacetic acid | THF | Tetrahydrofuran |
| TLC | Thin layer chromatography | Ts | Toluene sulfonyl |
| TsOH | para-toluene sulfonic acid | TsOH•H$_2$O | para-toluene sulfonic acid hydrate |

General Experimental Information:

Unless otherwise noted, all reactions are magnetically stirred.

Unless otherwise noted, when ethyl acetate, hexanes, dichloromethane, 2-propanol, and methanol are used in the experiments described below, they are Fisher Optima grade solvents.

Unless otherwise noted, when diethyl ether is used in the experiments described below, it is Fisher ACS certified material and is stabilized with BHT. Unless otherwise noted, "concentrated to dryness" means evaporating the solvent from a solution or mixture using a rotary evaporator.

Unless otherwise noted, flash chromatography is carried out on an Isco, Analogix, or Biotage automated chromatography system using a commercially available cartridge as the column. Columns may be purchased from Isco, Analogix, Biotage, Varian, or Supelco and are usually filled with silica gel as the stationary phase.

Microwave chemistry is performed in sealed glass tubes in a Biotage microwave oven.

General Synthetic Schemes

The general approach to these types of heterocycles is depicted in Scheme I. The Boc-amino acid i can be coupled to an appropriately substituted amine ii using standard conditions to provide amides iii. The BOC group in iii can be removed under acid conditions which provide amino-amides iv. Amino-amides iv can be reacted with acyclic ketones v to provide amino amides such as vi (e.g. microwave mediated—Feliu, L., Font, D., Soley, R., Tailhades, J., Martinez, J., Amblard, M. *ARKIVOC* 2007, 65; thermal conditions—Gomes, P., Araujo, M. J., Rodrigues, M., Vale, N., Azevedo, Z., Hey, J., Chanbel, P., Morals, J., Moreira, R. *Tetrahedron* 2004, 60, 5551 and Cheng, S., Wu, H., Hu. X. *Syn. Comm.* 2007, 37, 297); TsOH mediated cyclization as described herein. The amino intermediates such as vi can be oxidized to the imidazolone intermediates vii (e.g. Dean, A. W., Porter, R. A., WO 2007014762). The ester in vii can be hydrolyzed to provide the acid viii. The acid can be coupled to amines ix using standard protocols to provide the amides such as x. One skilled in the art would recognize that there are numerous coupling conditions for formation of amides.

Scheme 1

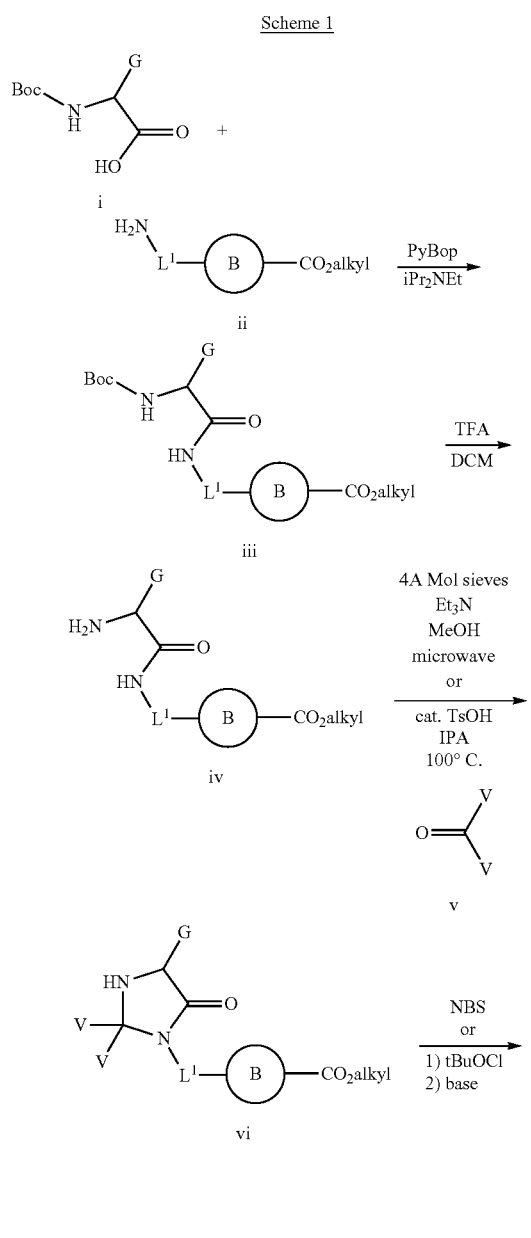

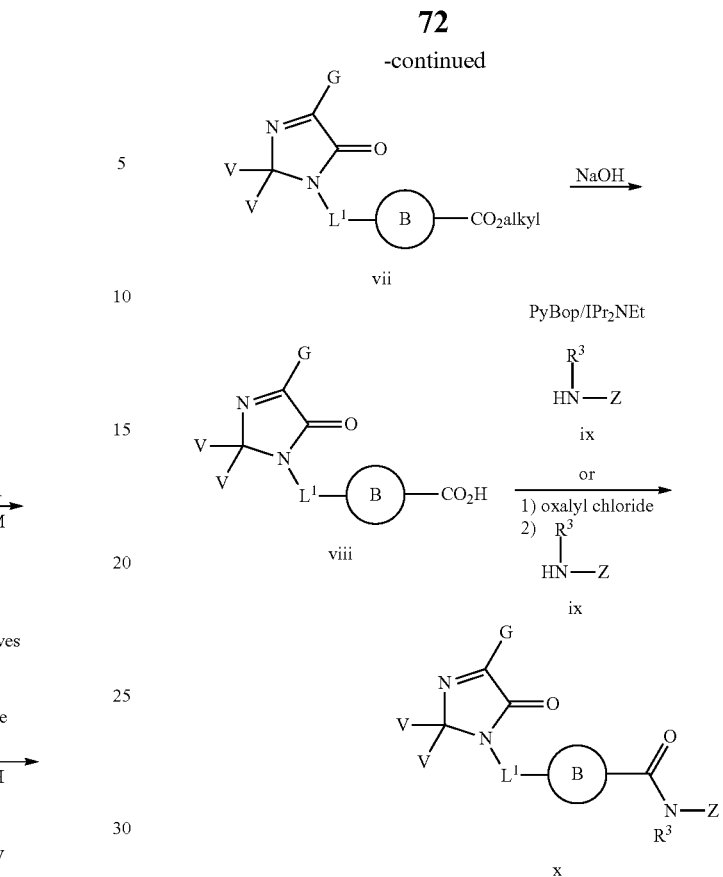

General experimental procedures for the synthesis of benzamides xiii and xvi from benzoic acid viii are described in Scheme 2 and Scheme 3 below.

Treatment of a suitable amine xi or xiv and a benzoic acid viii with a coupling reagent such as PyBOP and the like in a solvent such as DMF and the like will provide compounds xii or xv (Scheme 2). Cleavage of the tert-butyl ester present in compound xii with an acid such as trifluoroacetic acid or hydrochloric and the like will afford compound xiii. Cleavage of the tert-butyl ester present in compound xv with an acid such as trifluoroacetic acid or hydrochloric and the like will afford compound xvi.

Scheme 2

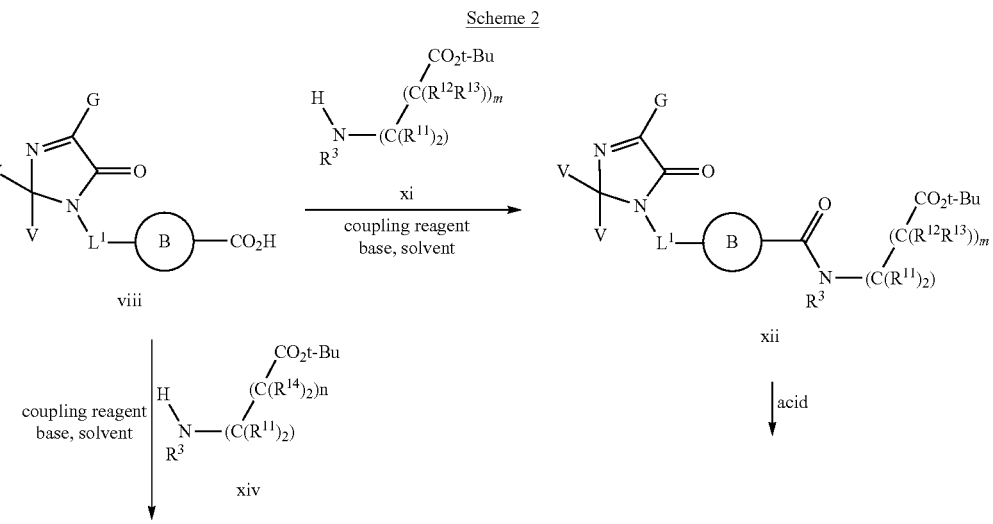

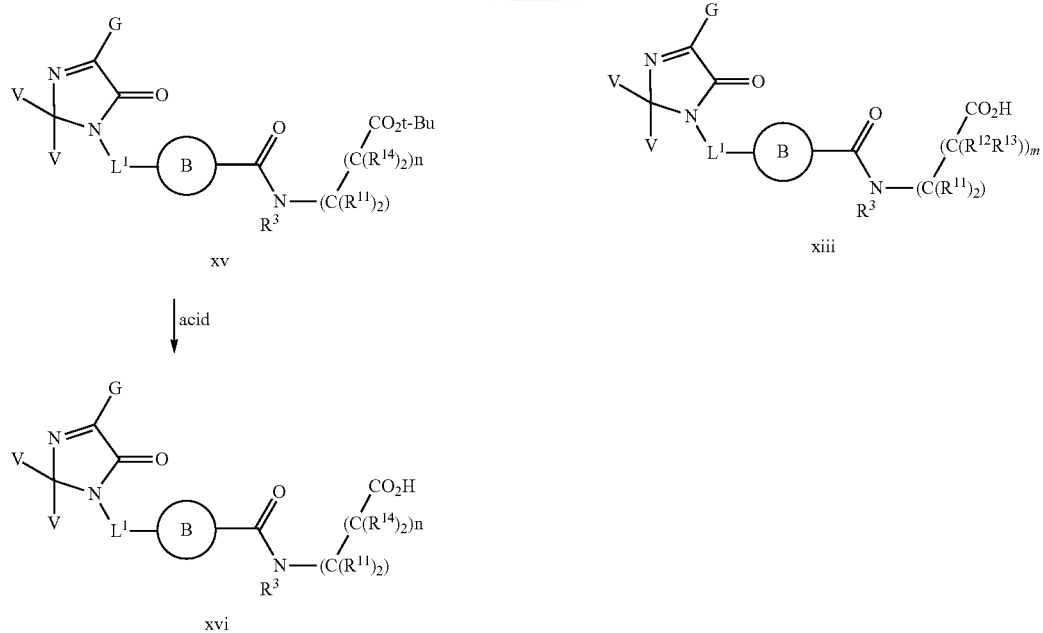

In Scheme 3, treatment of a suitable amine xvii or xix and a benzoic acid viii with a coupling reagent such as PyBOP and the like in a solvent such as DMF and the like will provide compounds xx or xviii. Hydrolysis of the methyl ester present in compound xx with an aqueous solution of a base such as NaOH and the like in a solvent mixture such as MeOH/THF and the like will afford compound xvi. Hydrolysis of the methyl ester present in compound xviii with an aqueous solution of a base such as NaOH and the like in a solvent mixture such as MeOH/THF and the like will afford compound xiii.

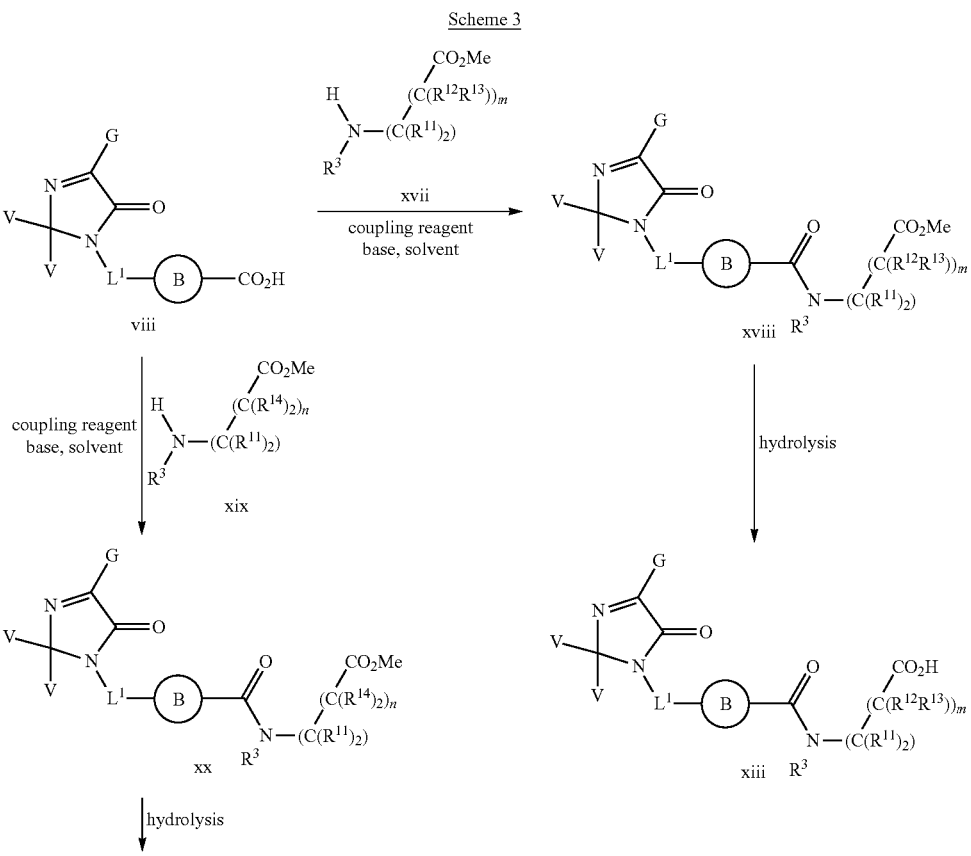

Scheme 3

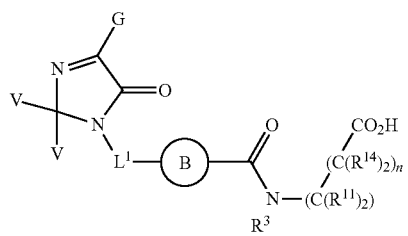
xvi

A general experimental procedure for the synthesis of benzamide xxii from benzoic acid viii is described in Scheme 4 below. Treatment of xxi (in its free or acid salt form) and a benzoic acid viii with a coupling reagent such as PyBOP and the like and a base such as iPr₂NEt and the like in a solvent such as DMF and the like will provide a desired compound xxii.

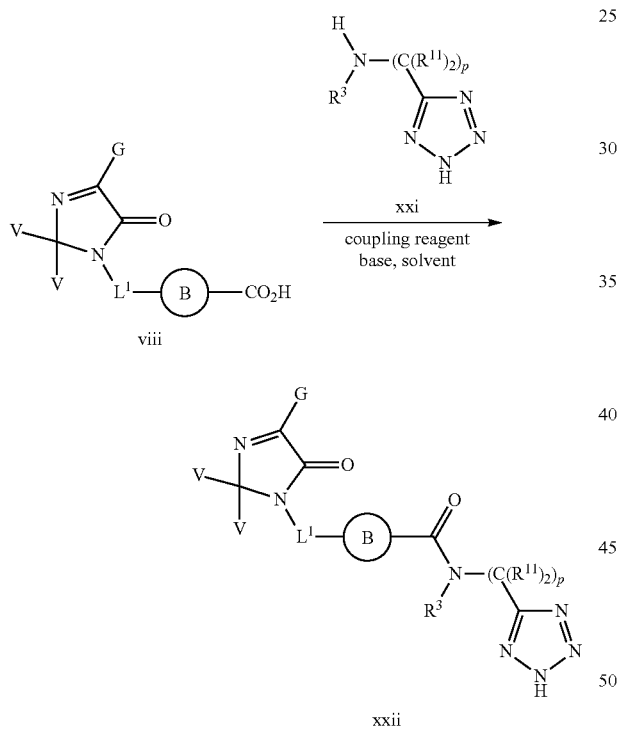

The Boc-glycine xxiii and amine ii can be converted into amides of the type xxiv using conditions previously outlined in Scheme 1. These can be treated with m-CPBA which can provide oxidized heterocycles such as xxvii. Heterocycles such as xxvii can be treated with Br₂PPh₃ to provide bromide analogs of the type xxviii. These intermediates can be reacted with various organometallic reagents using metal catalysis to furnish alkylated intermediates such as vii. The ester in vii can be hydrolyzed using conditions outlined in Step 5 of Scheme 1. The intermediate of the type viii can be processed into compounds such as xiii, xvi, and/or xxii using previously outlined conditions (Schemes 2, 3, and 4).

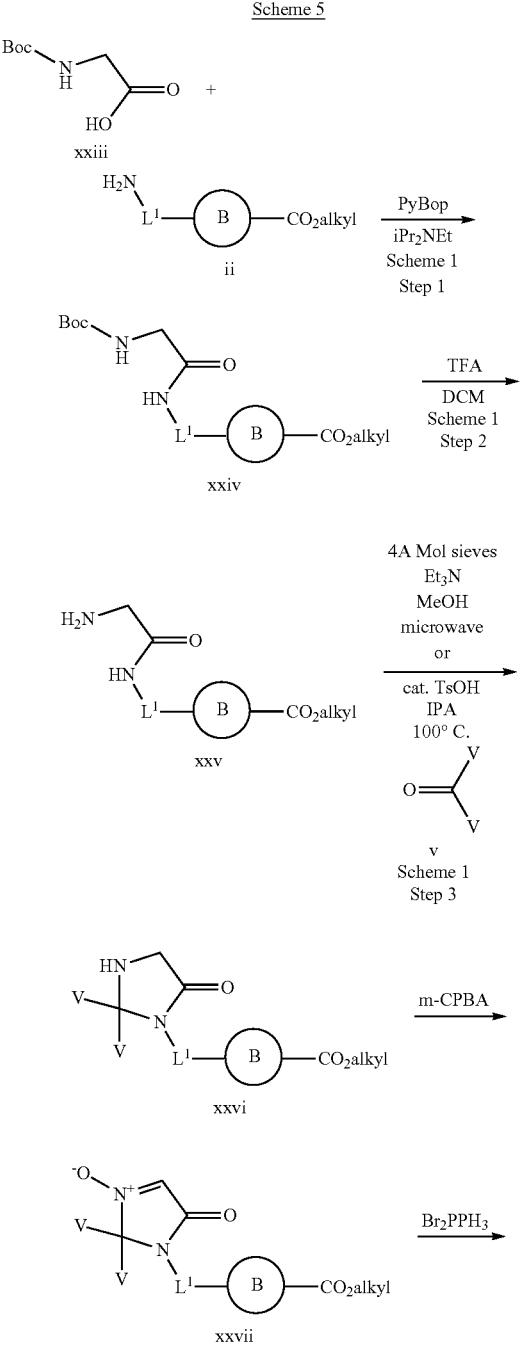

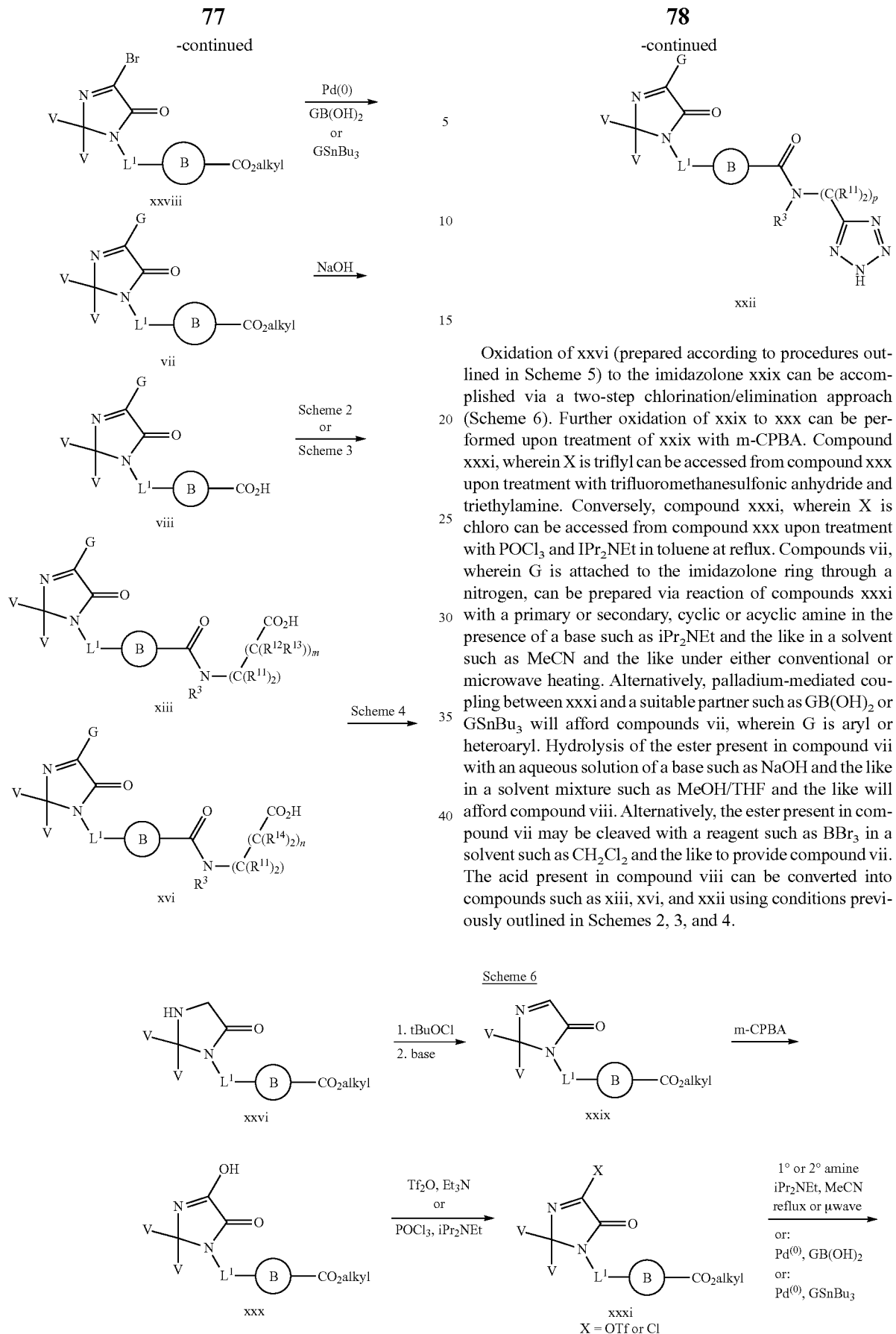

Oxidation of xxvi (prepared according to procedures outlined in Scheme 5) to the imidazolone xxix can be accomplished via a two-step chlorination/elimination approach (Scheme 6). Further oxidation of xxix to xxx can be performed upon treatment of xxix with m-CPBA. Compound xxxi, wherein X is triflyl can be accessed from compound xxx upon treatment with trifluoromethanesulfonic anhydride and triethylamine. Conversely, compound xxxi, wherein X is chloro can be accessed from compound xxx upon treatment with $POCl_3$ and $IPr_2NEt$ in toluene at reflux. Compounds vii, wherein G is attached to the imidazolone ring through a nitrogen, can be prepared via reaction of compounds xxxi with a primary or secondary, cyclic or acyclic amine in the presence of a base such as $iPr_2NEt$ and the like in a solvent such as MeCN and the like under either conventional or microwave heating. Alternatively, palladium-mediated coupling between xxxi and a suitable partner such as $GB(OH)_2$ or $GSnBu_3$ will afford compounds vii, wherein G is aryl or heteroaryl. Hydrolysis of the ester present in compound vii with an aqueous solution of a base such as NaOH and the like in a solvent mixture such as MeOH/THF and the like will afford compound viii. Alternatively, the ester present in compound vii may be cleaved with a reagent such as $BBr_3$ in a solvent such as $CH_2Cl_2$ and the like to provide compound vii. The acid present in compound viii can be converted into compounds such as xiii, xvi, and xxii using conditions previously outlined in Schemes 2, 3, and 4.

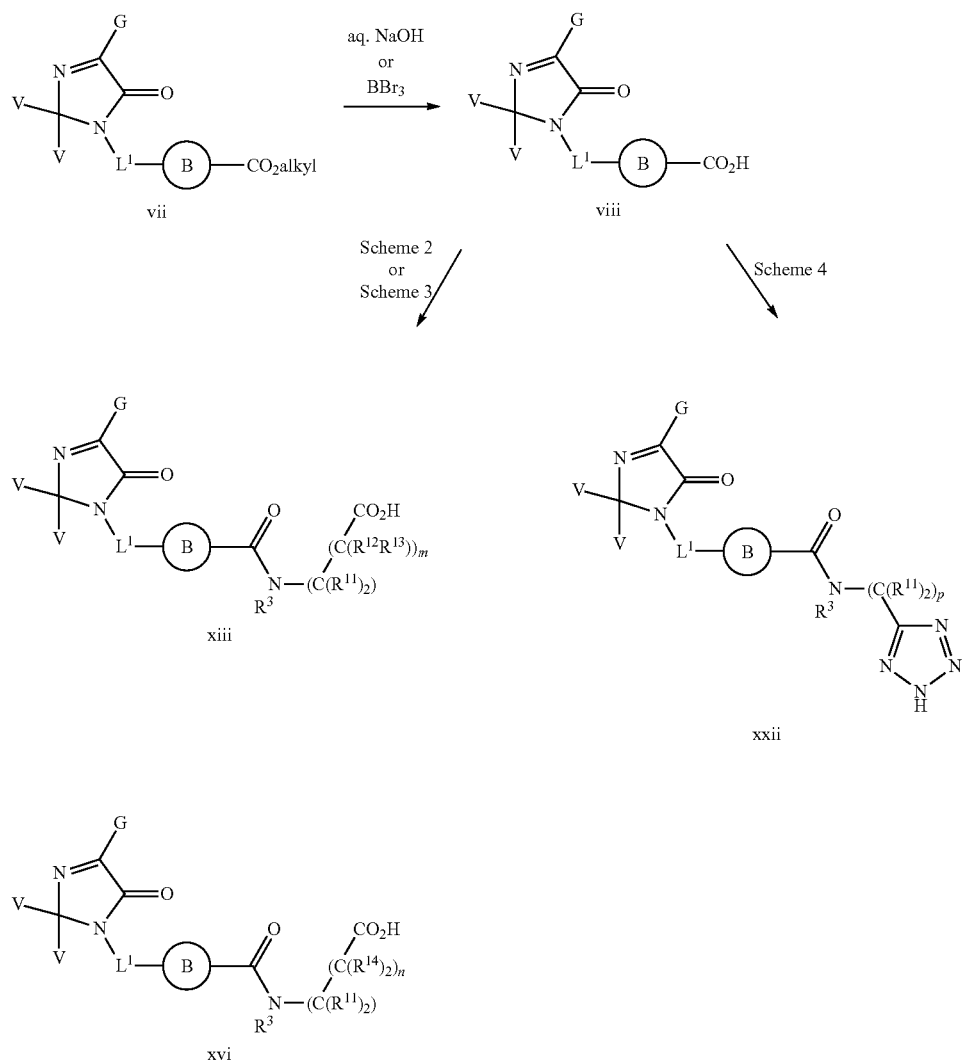

A general approach to enantiomerically enriched amines xxxvii and xxxviii is illustrated in Scheme 7. This approach is familiar to one skilled in the art, and numerous examples exist in the literature (for example see: Cogan, D. A.; Liu, G.; Ellman, J. A. *Tetrahedron* 1999, 55, 8883-8904). The condensation of the sulfinamide xxxii with aldehydes xxxiii provides the imines xxxiv. Organometallic reagents (such as grignards: $R^{5A}$MgBr) add to imines xxxiv to provide diastereomeric mixtures of the sulfinamides xxxv and xxxvi. These diastereomers can be purified by crystallization or chiral HPLC methods that are known to those skilled in the art. The pure diastereomers xxxv and xxxvi can be treated with HCl to provide the enantiomerically enriched amine HCl salts xxxvii and xxxviii, respectively.

Scheme 7

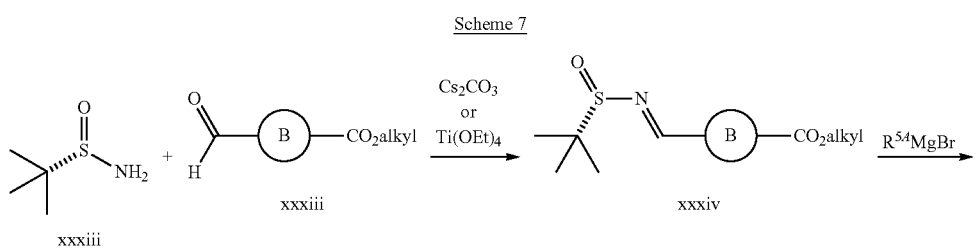

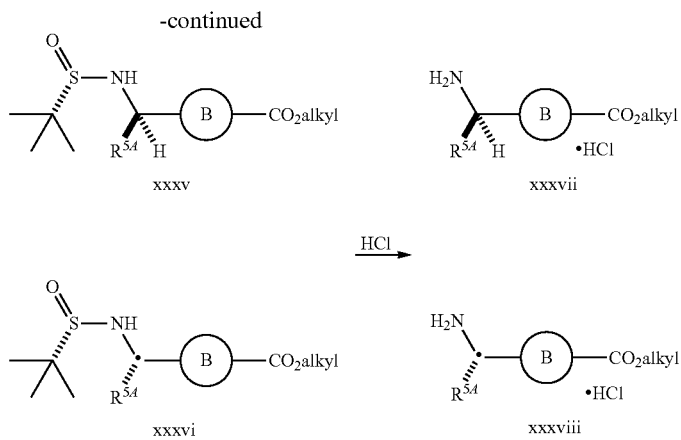

A related approach to these types of enantiomerically enriched amine HCl salts is illustrated in Scheme 8. The condensation of the sulfinamide xxxii with ketones such as xxxix will provide ketimines xl. Imines such as xl can be reduced (see Tanuwidjaja, J.; Peltier, H. M.; Ellman, J. A. *J. Org. Chem.* 2007, 72, 626) with various reducing reagents to provide sulfinamides such as xxv and xxxvi. As previously described, these sulfinamides can be treated with HCl to provide the enantiomerically enriched amine HCl salts xxxvii and xxxviii.

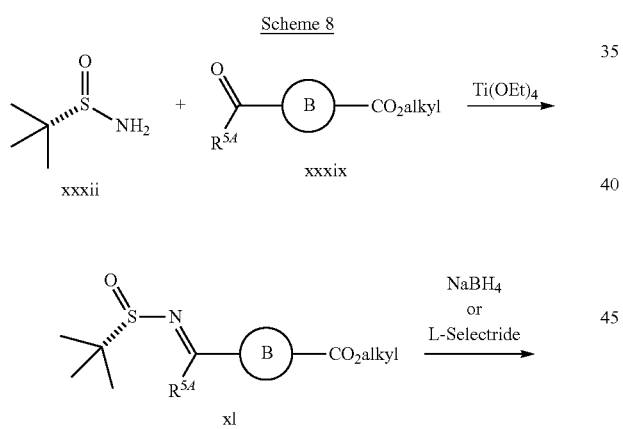

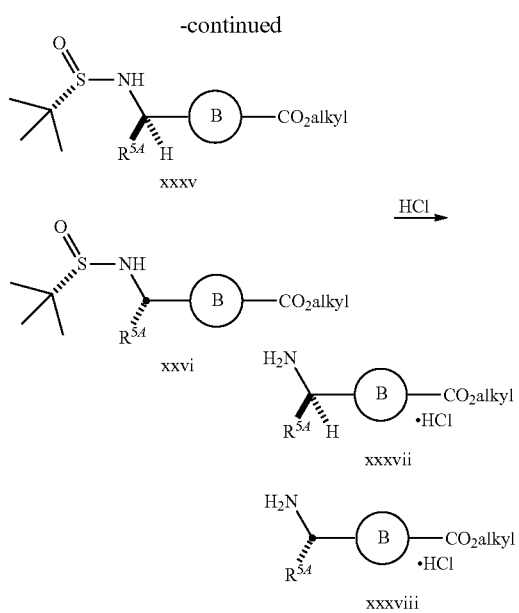

A general approach for the synthesis styrenyl imidazolones is summarized in Scheme 9 below. The nitrone xxvii can undergo a [3+2] cycloaddition with a styrene substituted with any of the substituents described in Formula A, items (i)-(xiii), as described for substituent G. This will provide the substituted phenyl isoxazolidine xli. Treatment of xli with aqueous NaOH followed by aqueous HCl will result in the formation of the styrenyl compounds xlii. These compounds can be processed into compounds such as xliii, xliv, and xlv using conditions outlined in Schemes 2, 3, and 4.

Scheme 9

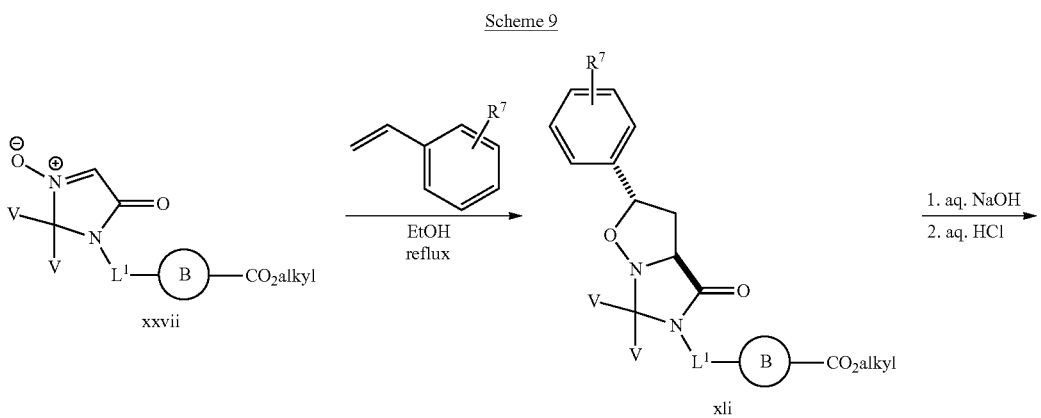

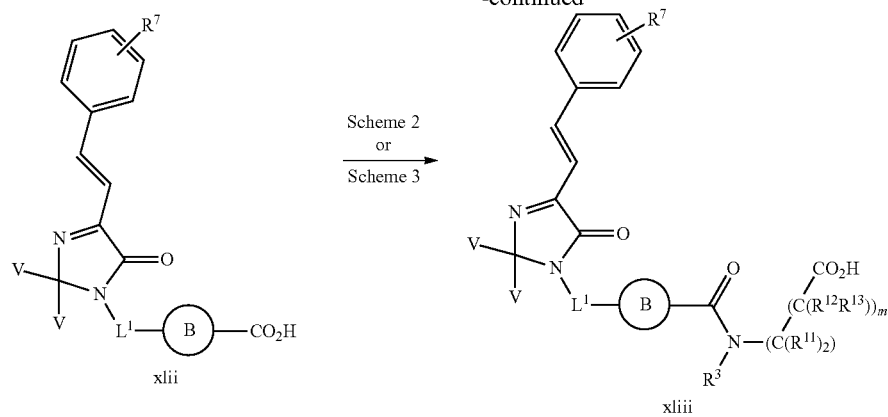

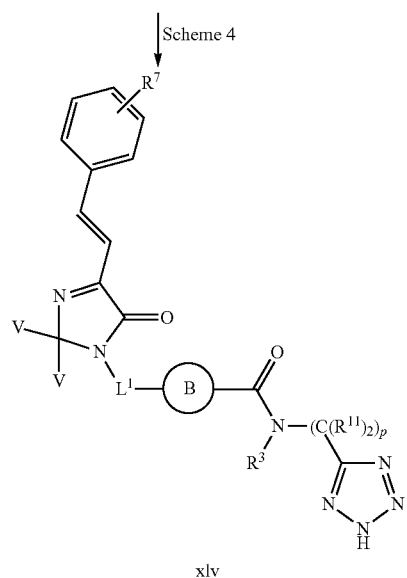

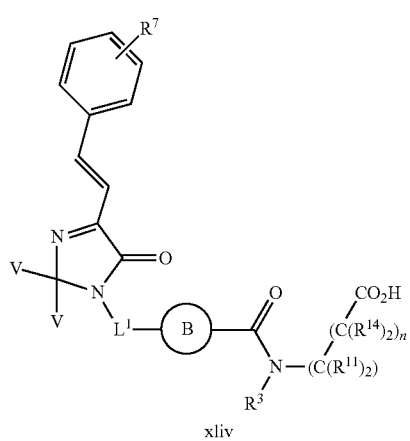

Also known to those skilled in the art, are the formation of tetrazole terminated compounds of the formula xxii via the method outlined in Scheme 10. The coupling of acids viii with cyano-substituted alkyl amines xlvi produces cyanoalkyl-amides of the type xlvii. The cyano group in xlvii will react with various reagents, including sodium azide in the presence of an alkyl amine hydrochloride, or sodium azide in the presence of $ZnBr_2$ in isopropanol/water to provide compounds xxii.

Scheme 10

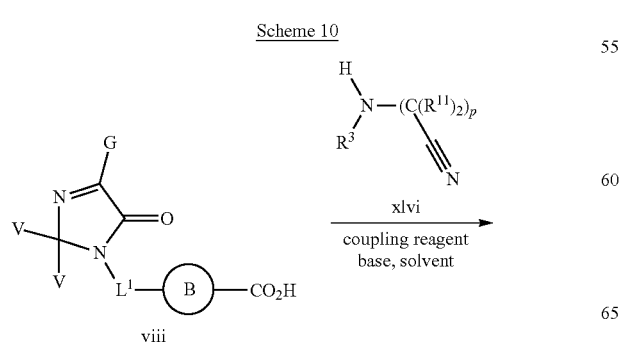

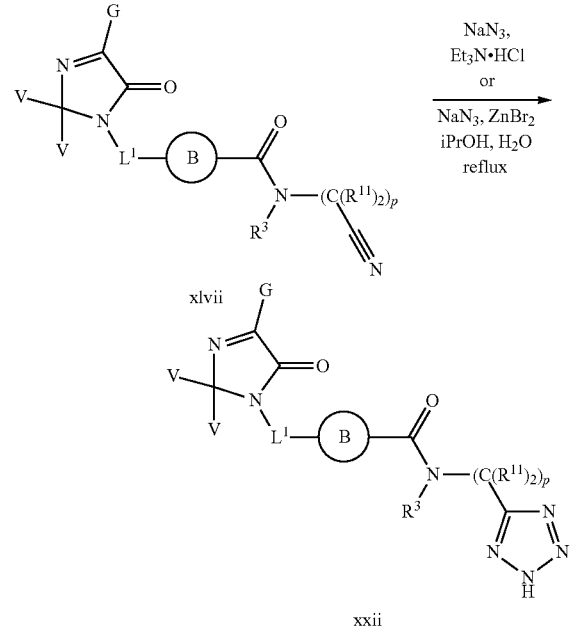

In an alternative method described in Scheme 11, nitrones such as xxvii can be treated with a reagent such as $POCl_3$ and the like in the presence of a base such as $iPr_2NEt$ and the like in a solvent such as toluene and the like to afford the chloroimidazolone xlviii. Treatment of xlviii with a primary or secondary amine at temperatures ranging from room temperature to 150° C. under either conventional or microwave heating will afford compounds vii, wherein G is an amine linked to the core through nitrogen. Alternatively, palladium-mediated coupling between xlviii and a suitable partner such as $GB(OH)_2$ or $GSnBu_3$ will afford compounds vii, wherein G is aryl or heteroaryl. The ester in vii can be hydrolyzed using acidic and/or basic conditions to provide the acid viii. The acid can be converted into compounds xiii, xvi, and xxii using conditions outlined above in Schemes 2, 3, and 4 wherein G in an amine linked to the core through the nitrogen.

Alternatively, as described in Scheme 12, one can treat an intermediate such as xxx with a coupling reagent such as PyBOP, PyBroP, or BOP-Cl and the like in the presence of a primary or secondary amine, and a base such as $iPr_2NEt$ and the like in a solvent such as MeCN or 1,4-dioxane and the like to directly prepare compounds vii, wherein G is an amine linked to the core through nitrogen. The ester in vii can be hydrolyzed using acidic and/or basic conditions to provide the acid viii. The acid can be converted into compounds xiii, xvi, and xxii using conditions outlined above in Schemes 2, 3, and 4 wherein G in an amine linked to the core through the nitrogen.

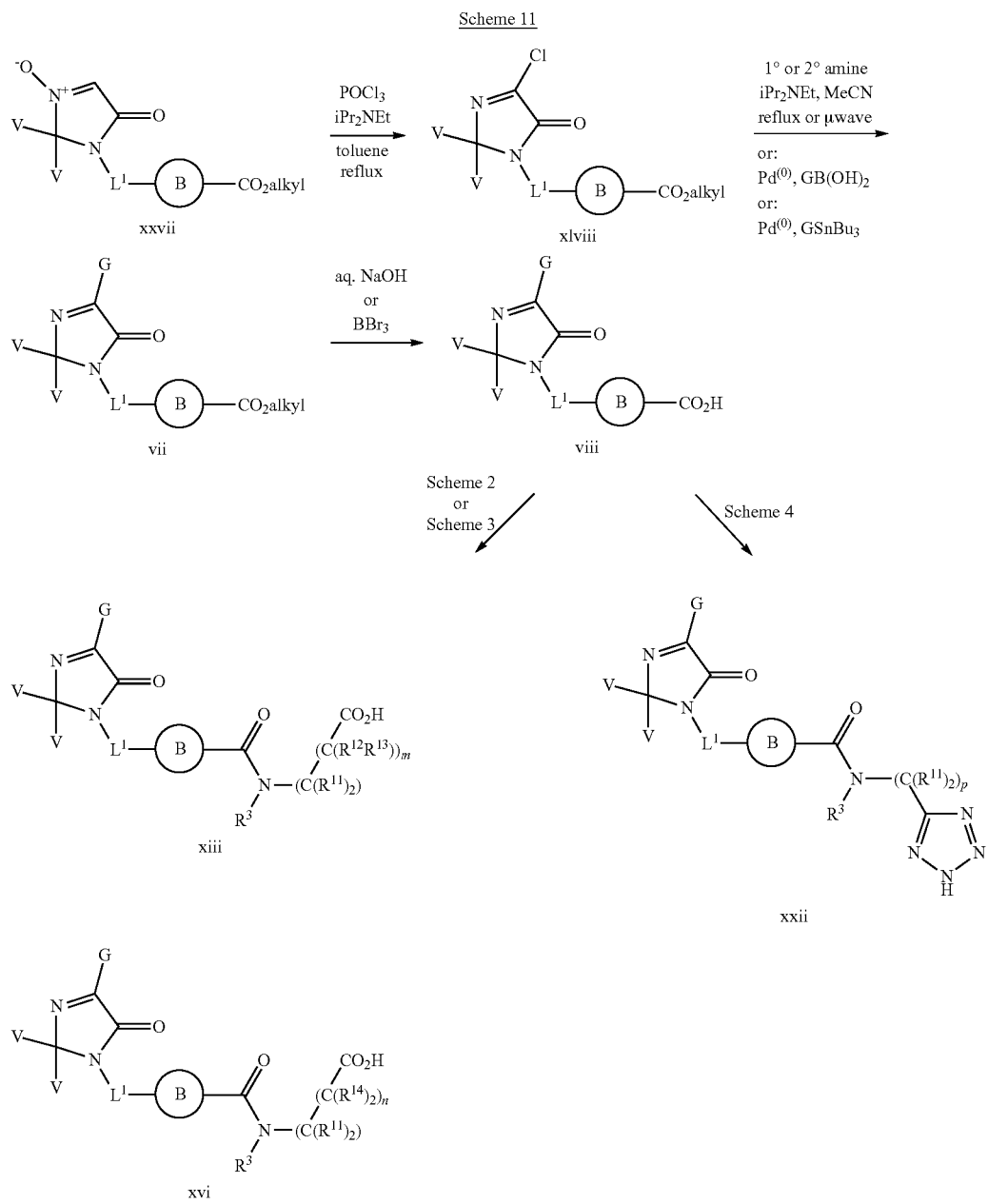

Scheme 12
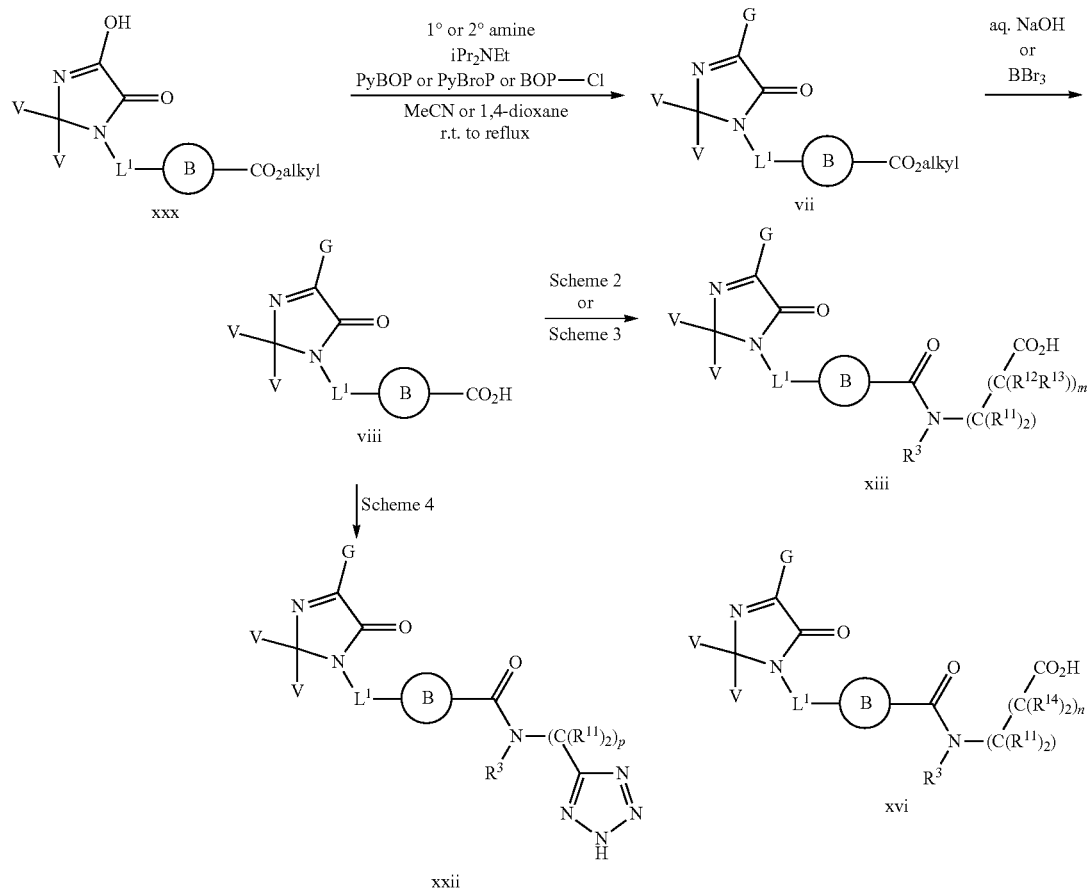
Procedures/Examples
Scheme A
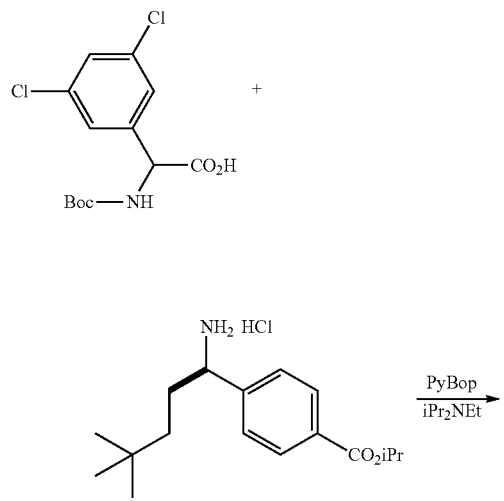
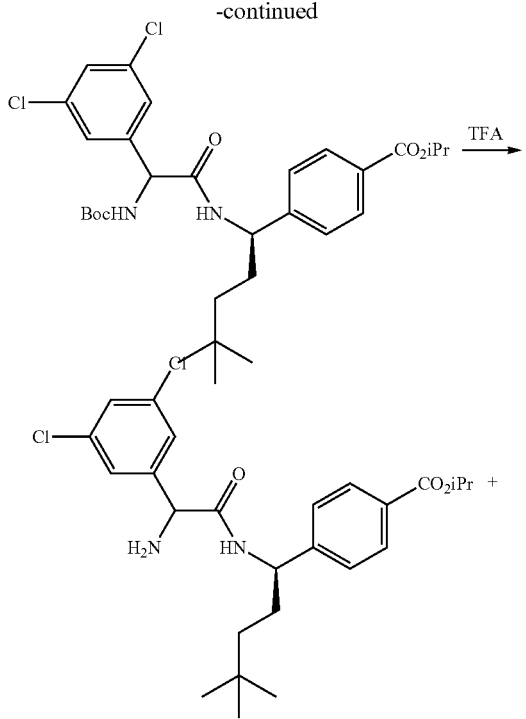

89
-continued
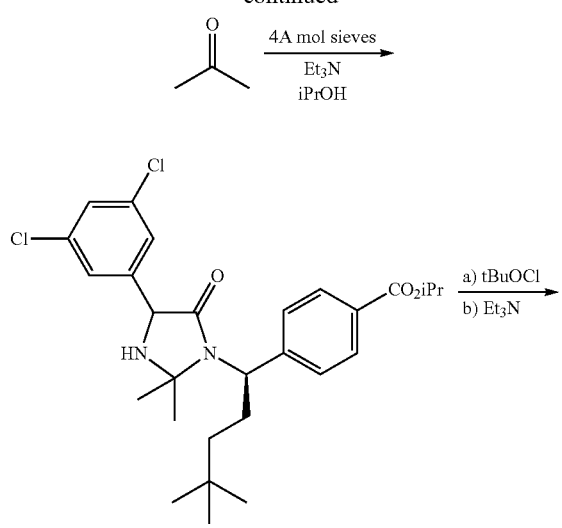
90
-continued
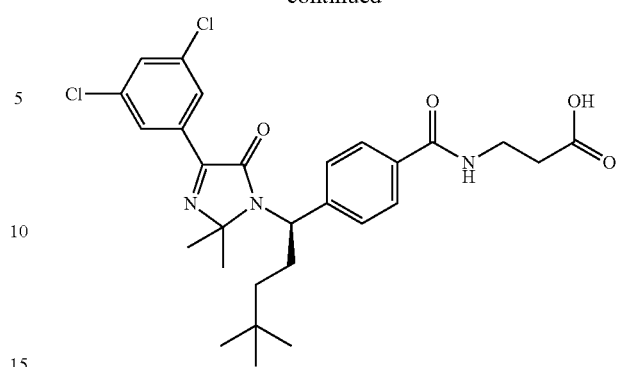
Example 1
Step 1
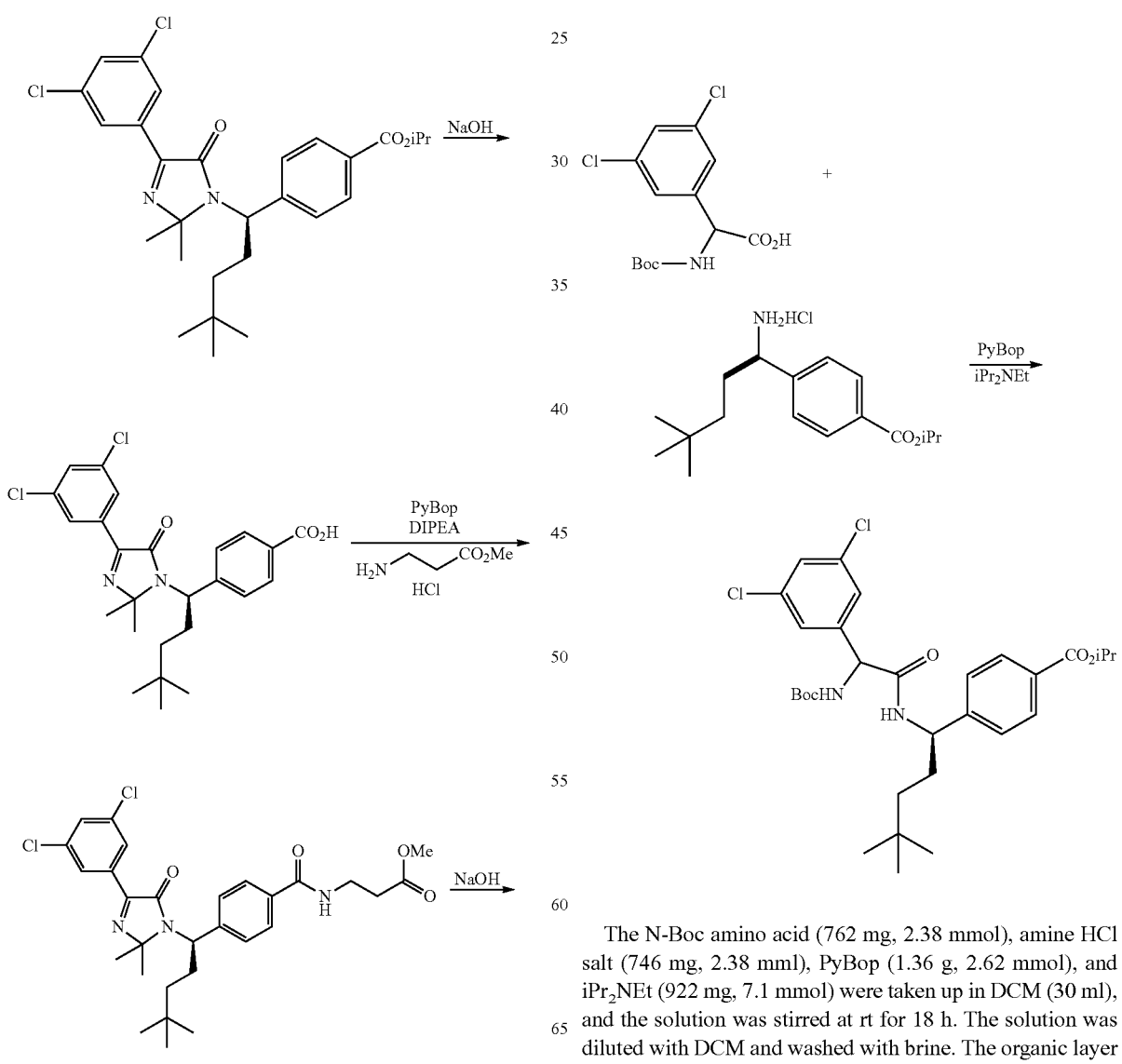
The N-Boc amino acid (762 mg, 2.38 mmol), amine HCl salt (746 mg, 2.38 mml), PyBop (1.36 g, 2.62 mmol), and iPr₂NEt (922 mg, 7.1 mmol) were taken up in DCM (30 ml), and the solution was stirred at rt for 18 h. The solution was diluted with DCM and washed with brine. The organic layer was dried (Na₂SO₄), filtered, and concentrated. The residue was purified via gradient flash chromatography (0-25% EtOAc in hexanes, SiO$_2$) which provided the amide as a colorless foam.

Step 2

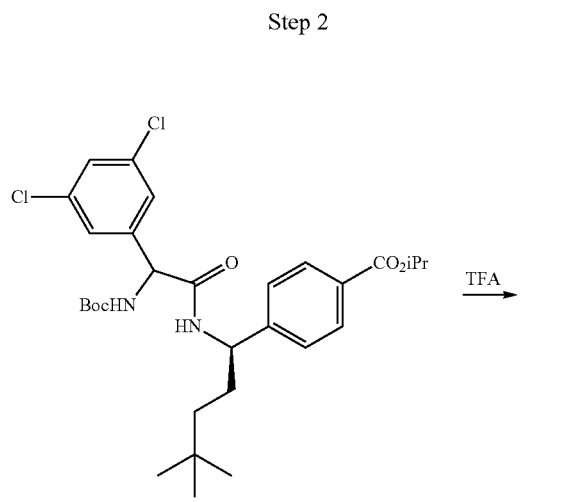

The amide (1.34 g, 2.3 mmol) and TFA (5 ml) were taken up in DCM (10 ml), and the solution was stirred at RT for 3 h. The solution was concentrated, and the residue was partitioned between DCM and 1 N NaOH$_{(aq.)}$. The aqueous layer was extracted with DCM. The combined organic layers were dried (Na$_2$SO$_4$), filtered, and concentrated which provided the amine as a colorless foam.

Step 3

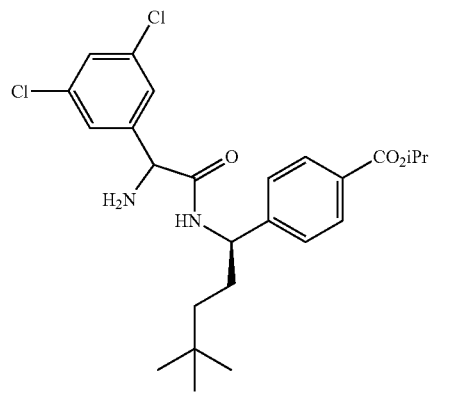

+

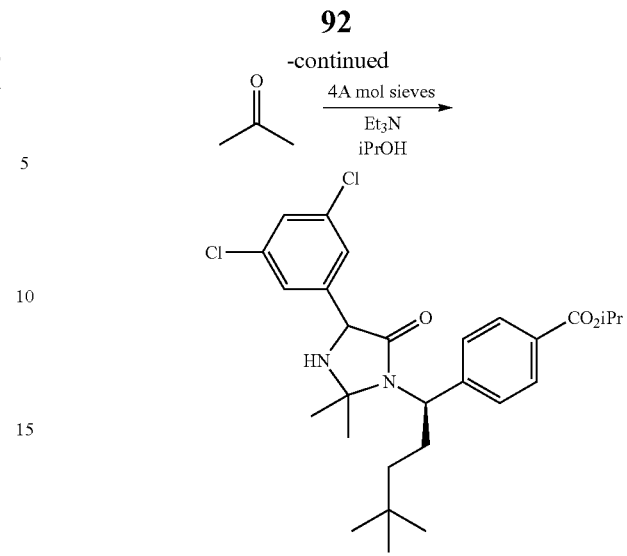

The amine (540 mg, 1.1 mmol), acetone (1.97 g, 34 mmol), Et$_3$N (229 mg, 2.26 mmol), and 4 A mol sieves (2 g) were taken up in IPA (15 ml), and the resulting mixture was stirred at reflux (105° C.) for 18 h. The mixture was filtered and concentrated. The residue was purified via gradient flash chromatography (0-50% EtOAc in hexanes, SiO$_2$) which provided the spiro-amine as a colorless foam.

Step 4

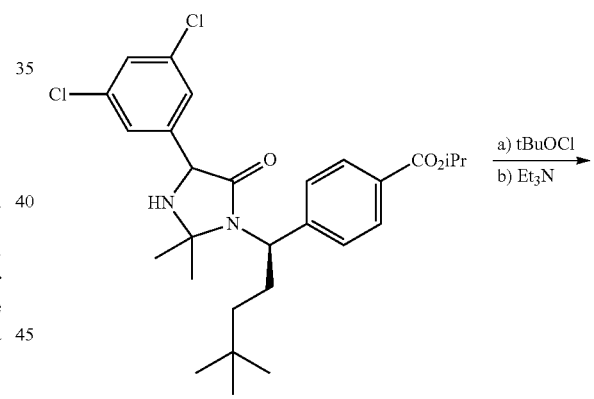

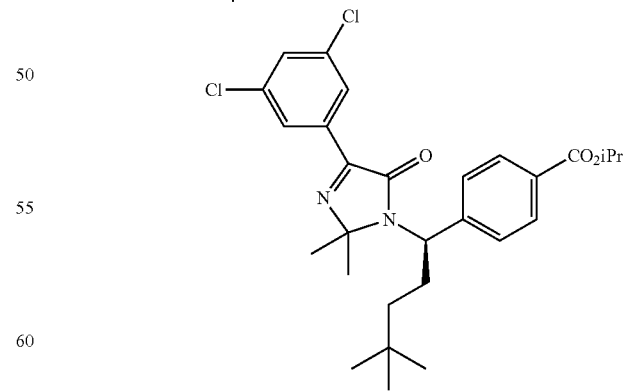

The amine (353 mg, 0.68 mmol) was taken up in DCM (10 ml) at rt. tert-Butyl hypochlorite (115 mg, 1.06 mmol) was added to the solution at RT, and the resulting solution was stirred at RT for 20 minutes. Triethylamine (358 mg, 3.54 mmol) was added, and the solution was stirred at RT for 1 hour. The solution was diluted with DCM and washed with 10% NaHSO$_{3(aq.)}$. The aqueous layer was extracted with DCM. The combined organic layers were dried (Na$_2$SO$_4$), filtered, and concentrated. The residue was purified via gradient flash chromatography (0-5% EtOAc in hexanes, SiO$_2$) which provided the imidazolone-ester as a colorless oil.

Step 5

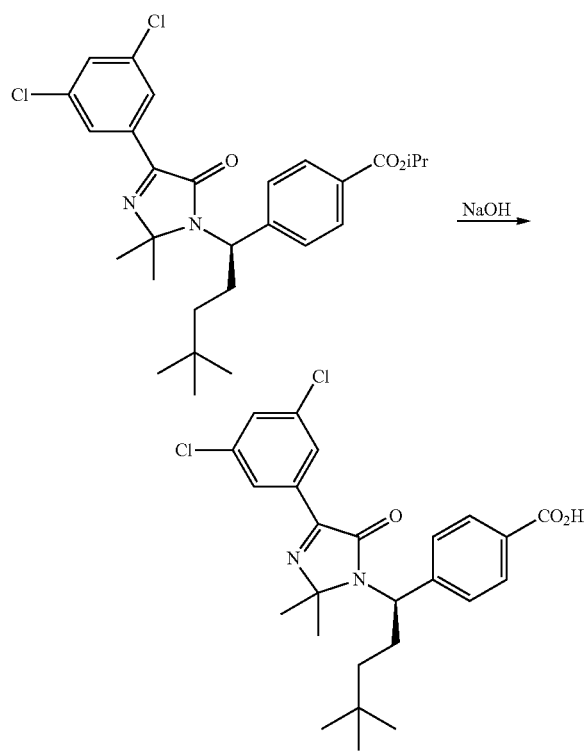

The ester (323 mg, 0.62 mmol) was taken up in THF/MeOH (3 ml/3 ml), and 2 ml of 2 N NaOH$_{(aq.)}$ was added. The solution was stirred at RT for 4 h. The solution was concentrated, and the residue was partitioned between 1 M HCl$_{(aq.)}$ and DCM. The aqueous layer was extracted with DCM. The combined organic layers were dried (Na$_2$SO$_4$), filtered, and concentrated which provided the acid as a colorless foam.

Step 6

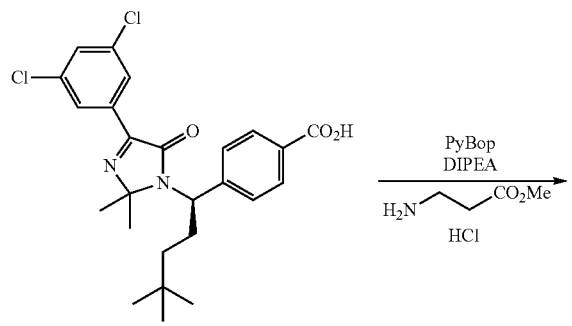

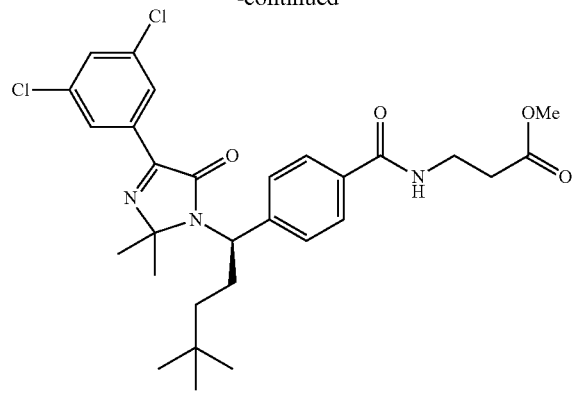

The acid (75 mg, 0.16 mold), methyl 3-aminopropanoate HCl (24 mg, 0.17 mmol), PyBop (90 mg, 0.17 mmol), and iPr$_2$NEt (61 mg, 0.47 mmol) were taken up in DCM (2.5 ml), and the resulting solution was stirred at RT for 18 h. The solution was diluted with DCM and washed with water. The aqueous layer was extracted with DCM. The combined organic layers were dried (Na$_2$SO$_4$), filtered, and concentrated. The residue was purified via gradient flash chromatography (0-40% EtOAc in hexanes, SiO$_2$) which provided the ester as a colorless foam.

Step 7

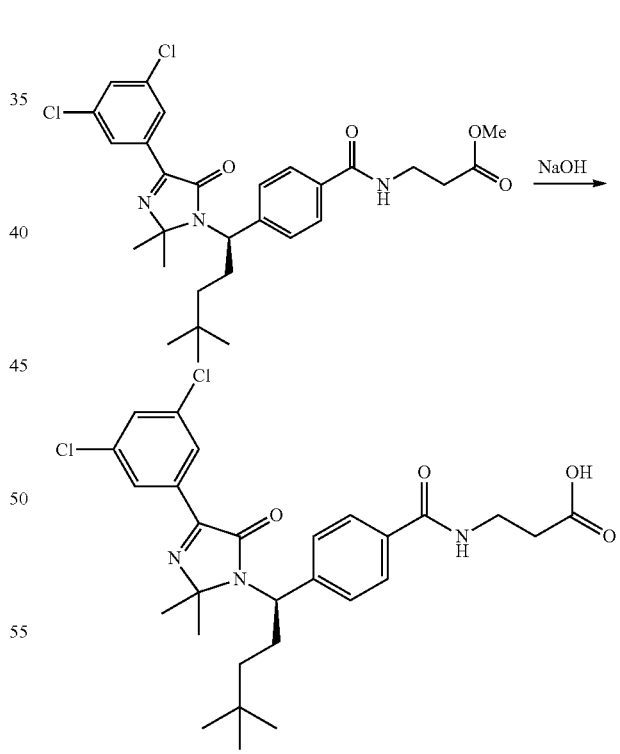

Example 1

The ester (70 mg, 0.12 mmol) was taken up in THF/MeOH (3 ml/3 ml) and 2 ml of 2 N NaOH$_{(aq.)}$. The solution was stirred at RT for 5 h. The solution was concentrated. The residue was acidified with 1 N HCl$_{(aq.)}$. The solution was extracted with EtOAc. The combined organic layers were dried (MgSO$_4$), filtered, and concentrated. The residue was purified via reverse phase chromatography (10-80% CH$_3$CN in $_{H2O}$ with 0.1% HCO$_2$H, C-18) which provided the compound of Example 1 as a colorless solid after evaporation and freeze drying.

Scheme B

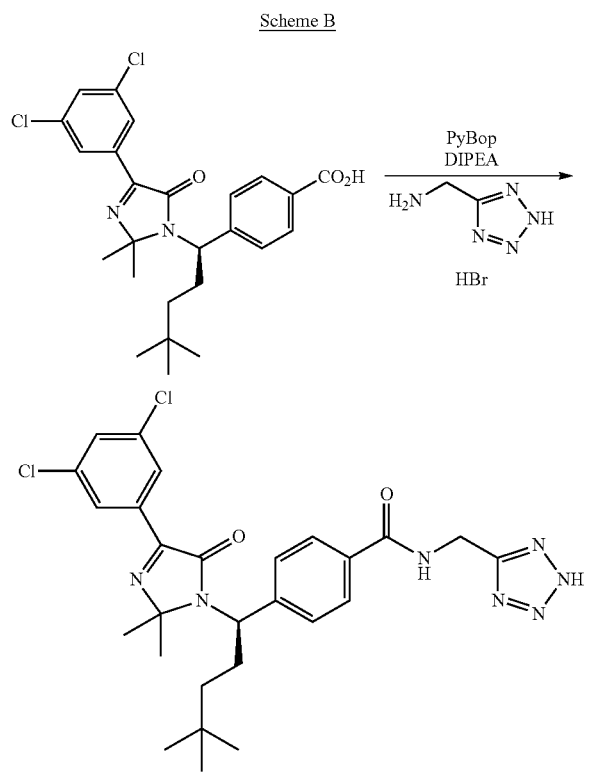

Example 2

The acid (75 mg, 0.16 mmol; prepared according to procedures outlined in Scheme A), PyBop (90 mg, 0.17 mmol), iPr$_2$NEt (61 mg, 0.047 mmol), and (2H-tetrazol-5-yl)methanamine HBr (43 mg, 0.24 mmol) were taken up in DMF (2 ml), and the resulting solution was heated at 70° C. for 1 h. The solution was concentrated, and the residue was dissolved in DMSO (3 ml) and loaded onto a reverse phase column (C-18). The sample was eluted using 10-80% MeOH in H$_2$O with 0.05 TFA gradient which provided the compound of Example 2 as a colorless solid after evaporation and freeze drying.

Scheme C

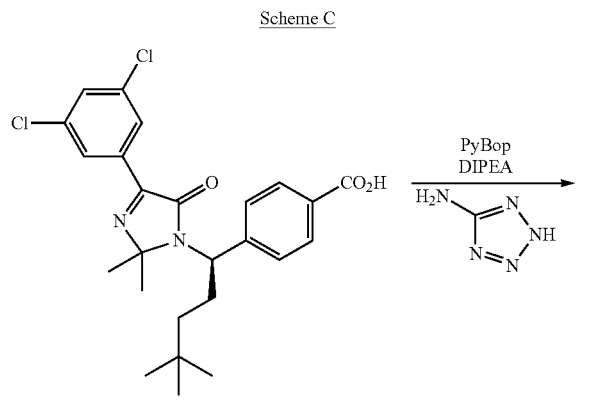

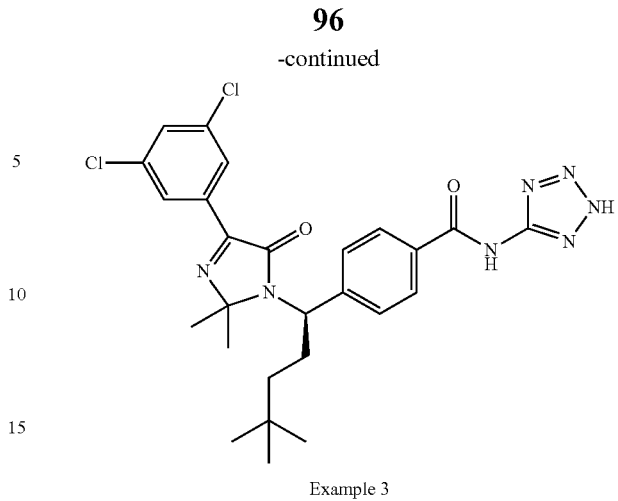

Example 3

The acid (75 mg, 0.16 mmol; prepared according to procedures outlined in Scheme A), PyBop (90 mg, 0.17 mmol), iPr$_2$NEt (61 mg, 0.047 mmol), and 2H-tetrazol-5-amine (20 mg, 0.24 mmol) were taken up in DMF (2 ml), and the resulting solution was heated at 70° C. for 1 h. The solution was concentrated, and the residue was dissolved in DMSO (3 ml) and loaded onto a reverse phase column (C-18). The sample was eluted using 10-80% MeOH in H$_2$O with 0.05% TFA gradient which provided the compound of Example 3 as a colorless solid after evaporation and freeze drying.

The compounds of examples 4-16 are made by processes analogous to the Schemes A through D described herein, and are shown in Table 1.

Scheme D

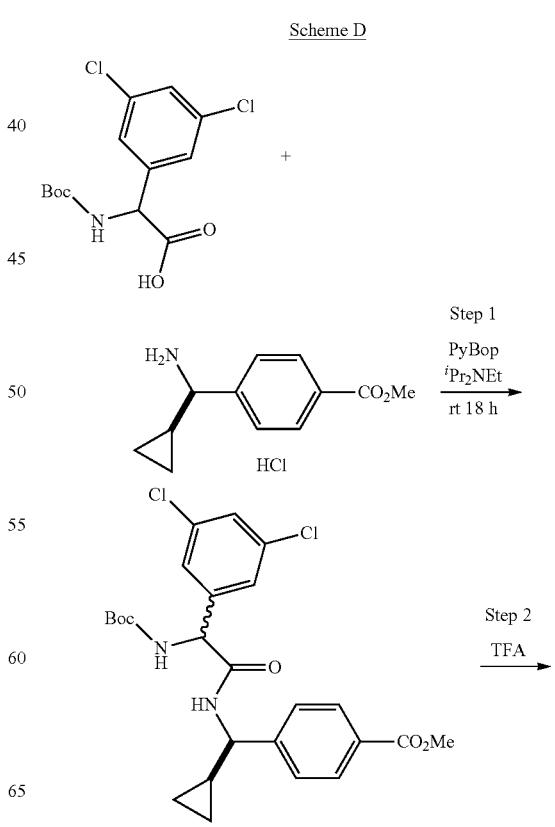

97

-continued

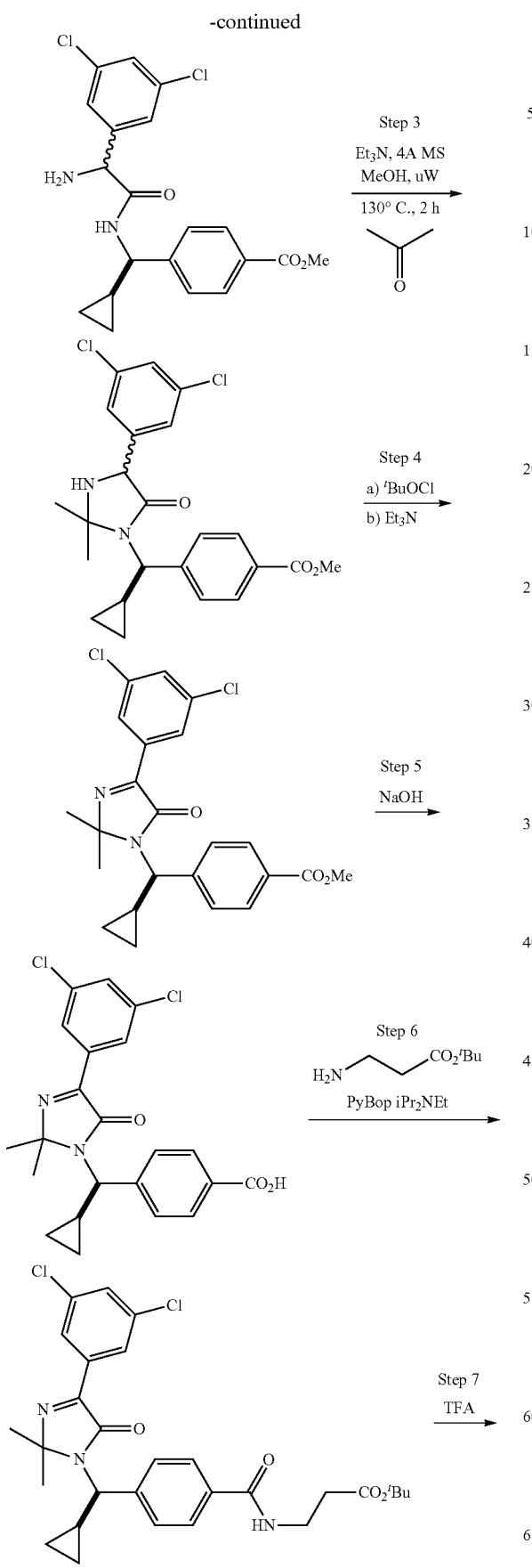

98

-continued

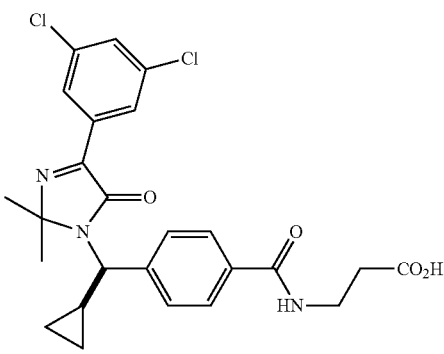

Example 17

Step 1

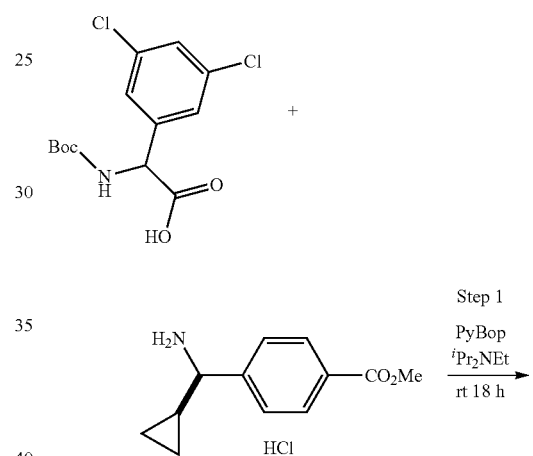

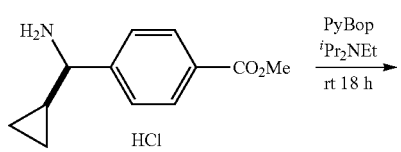

2-(tent-Butoxycarbonylamino)-2-(3,5-dichlorophenyl) acetic acid (681 mg, 2.13 mmol), (R)-methyl 4-(amino(cyclopropyl)methyl)benzoate HCl (468 mg, 1.94 mmol), PyBop (1.11 g, 2.13 mmol), and iPr$_2$NEt (1.01 mL, 5.82 mmol) were taken up in CH$_3$CN (20 mL), and the solution was stirred at room temperature for 18 hours. The solution was concentrated, and the residue was partitioned between EtOAc and sat. NaHCO$_{3(aq.)}$. The aqueous layer was extracted with EtOAc, and the combined organic layers were dried over Na$_2$SO$_4$. The mixture was filtered and concentrated which provided a yellow oil. The residue was purified by gradient flash chromatography (ISCO, 0 to 40% EtOAc in hexanes) which provided the amide as a white solid.

Step 2

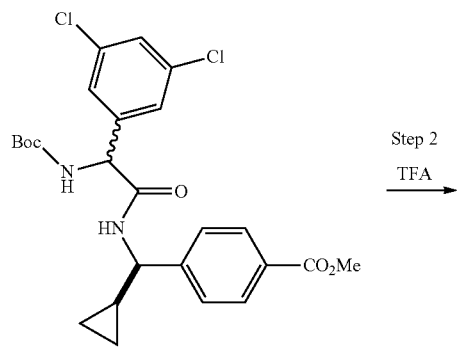

The Boc-amine (1.01 g) was taken up in 20% TFA/DCM (10 mL at room temperature. The solution was stirred at room temperature for 18 hours. The solution was concentrated, and the residue was partitioned between DCM and 1 N NaOH$_{(aq.)}$. The aqueous layer was extracted with DCM. The combined organic layers were dried (Na$_2$SO$_4$), filtered and concentrated which furnished the amine as a yellow solid.

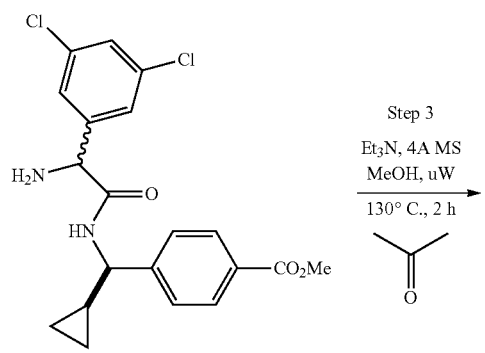

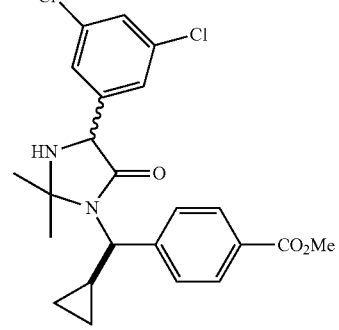

The free amine (355 mg, 0.87 mmol), 4-tert-butyl-cyclohexanone (270 mg, 1.75 mmol) or acetone (254 mg, 4.37 mmol), 4 A mol sieves (350 mg), and Et$_3$N (0.25 mL) were taken up in MeOH (5 mL). The mixture was heated in a microwave (130° C., 2 h). The mixture was filtered, and the solution was concentrated. The residue was purified via gradient flash chromatography (ISCO, 0-35% EtOAc in hexanes) which furnished the spiro-amine as a white semi-solid.

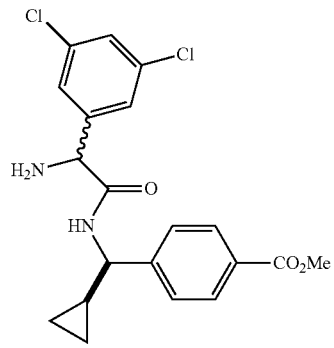

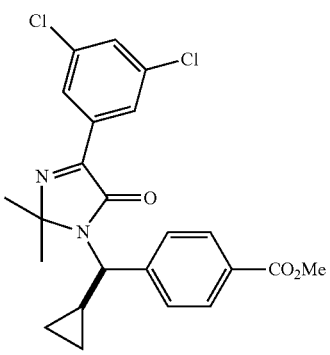

To a solution of the spiro-amine (118 mg, 0.26 mmol) in DCM (5 mL), was added t-butyl-hypochlorite (38 uL). After 1 hour at room temperature, Et$_3$N (0.15 mL) was added, and the reaction was stirred at room temperature for another 2 hours. The reaction was quenched with aqueous Na$_2$S$_2$O$_3$ solution and extracted with DCM (30 mL×3). The combined organic layers were concentrated. The residue was used without further purification

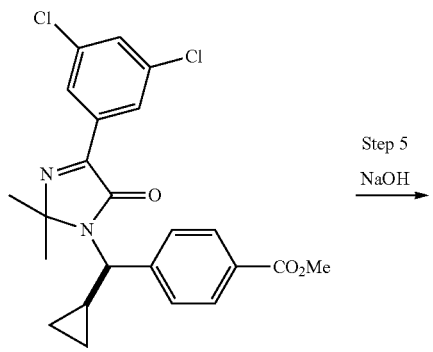

Step 5
NaOH
→

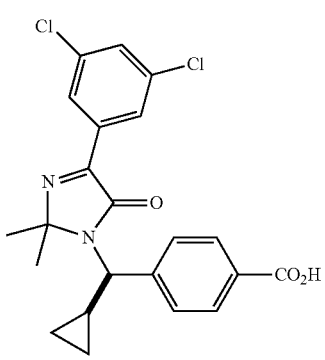

The starting material was taken up in 1 N NaOH$_{(aq.)}$/dioxane/MeOH (1/1/1, 30 ml total), and the solution was heated at 65° C. for 5 hours. The solution was cooled and stirred at room temperature for 16 hours. The solution was concentrated. The residue was partitioned between DCM and 1 M HCl$_{(aq.)}$. The mixture was stirred at room temperature for 0.5 h. The layers were separated, and the aqueous layer was extracted with DCM. The combined organic layers were dried (MgSO$_4$), filtered, and concentrated which afforded the acid as a white solid.

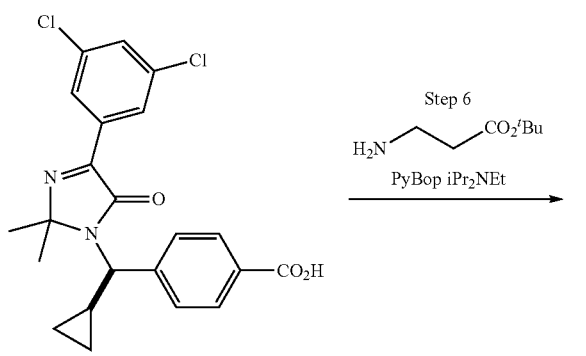

Step 6
H$_2$N—CO$_2^t$Bu
PyBop iPr$_2$NEt
→

-continued

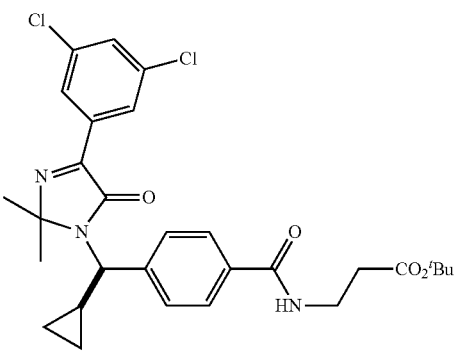

The acid (125 mg, 0.29 mol), PyBop (229 mg, 0.44 mmol), $^i$Pr$_2$NEt (114 mg, 0.88 mmol) and beta-alanine tert-butyl ester HCl salt (64 mg, 0.44 mmol), were taken up in CH$_3$CN (10 mL), and the solution was stirred at room temperature for 18 hours. The solution was concentrated, and the residue was partitioned between EtOAc and sat. NaHCO$_3$ (aq). The aqueous layer was extracted with EtOAc. The combined organic layers were washed with brine and dried (MgSO$_4$). Filtration and concentration provided a yellow oil. The residue was purified via gradient flash chromatography (ISCO, 0-35% EtOAc in hexanes) which provided the tert-butyl ester as a colorless oil.

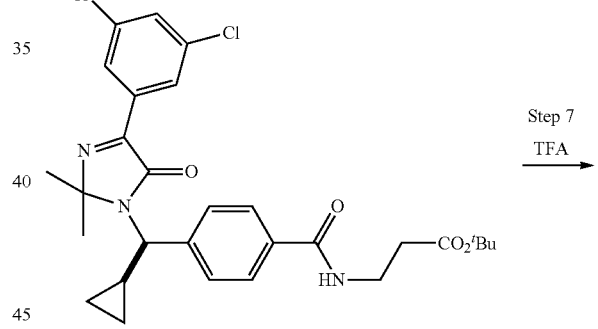

Step 7
TFA
→

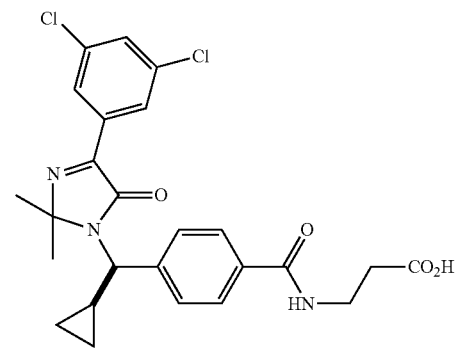

Example 17

The tea-butyl ester (140 mg) was treated with 20% TFA/DCM (5 mL) at room temperature for 18 hours. The solution was concentrated and dried under high vacuum which provided Example 17.

Scheme E
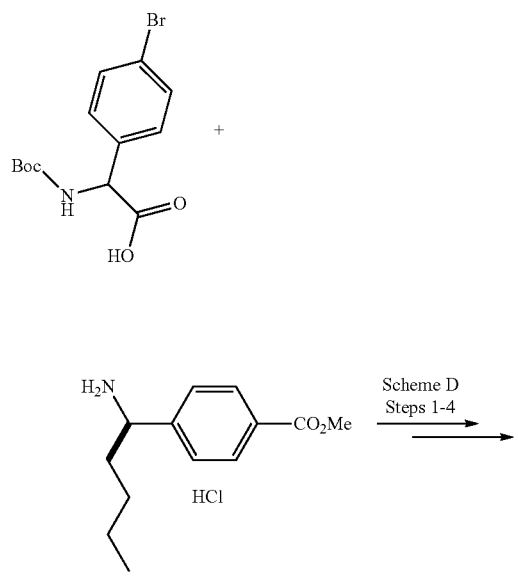
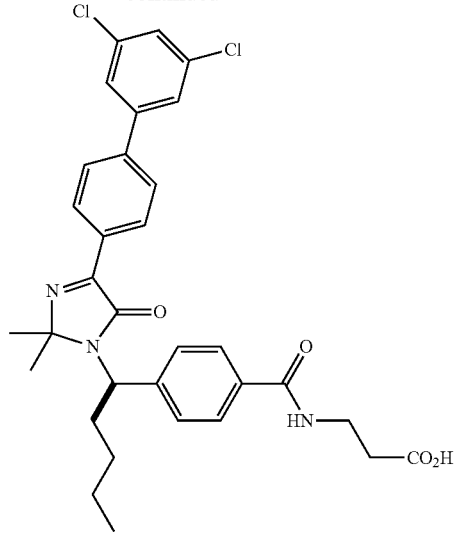
Example 18
The bromide was prepared using conditions outlined in Scheme D Steps 1-4 using the appropriate amino acid, amine HCl salt, and ketone.
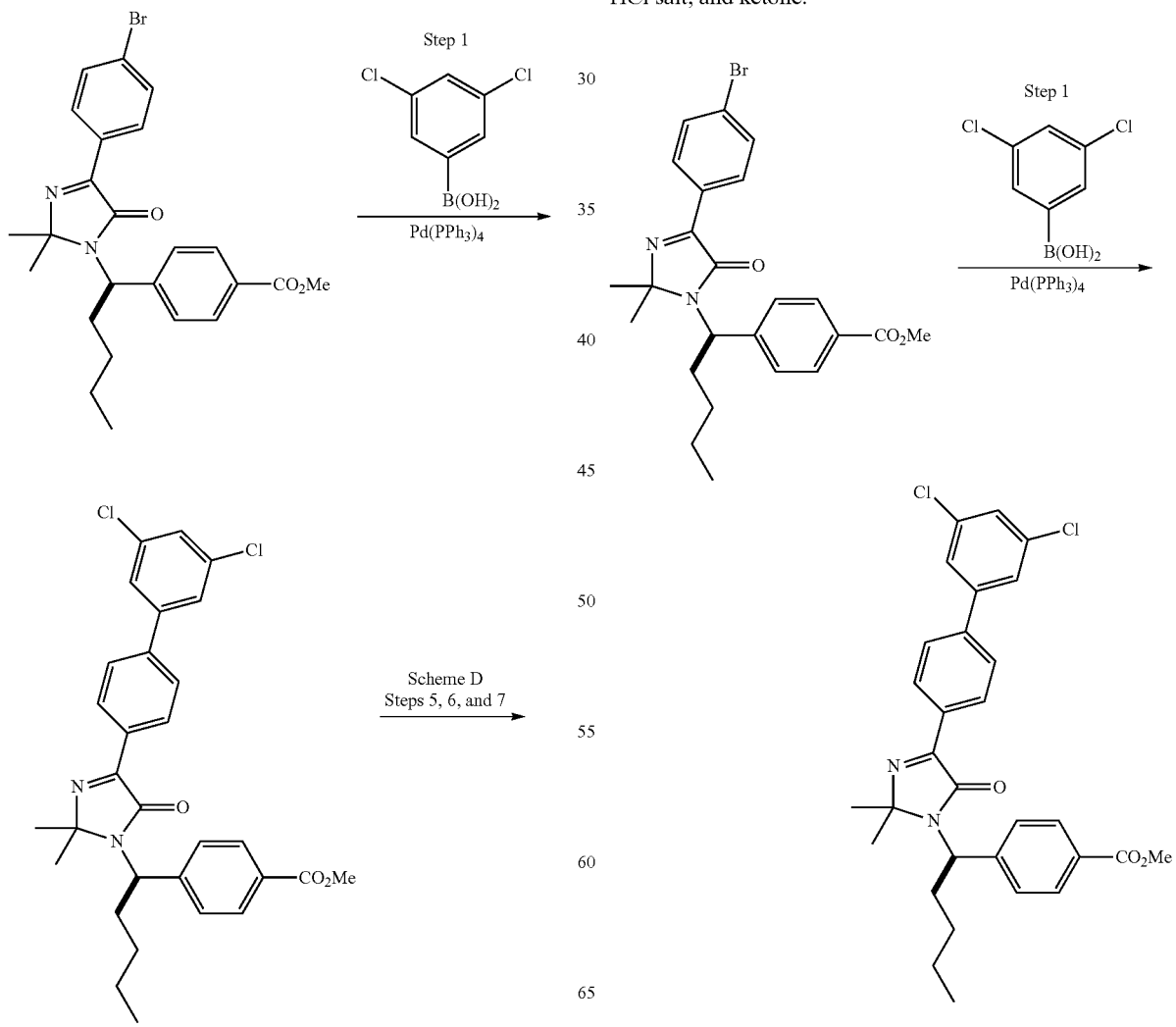

The bromide (136 mg, 0.28 mmol), Pd(PPh$_3$)$_4$ (33 mg, 10% mmol), boronic acid (82 mg, 0.43 mmol) and 0.5 mL of aq. NaHCO$_3$ solution, and 5 mL of toluene/EtOH (1/1) were placed into a 20 ml vial. The vial was capped, sealed, and heated at 100° C. for 16 hrs. The mixture was diluted with ether, filtered through celite, and concentrated. The residue was purified via gradient flash chromatography (ISCO, 0-40% EtOAc in hexanes) which furnished the desired arylated product.

The arylated product was converted into Example 18 using conditions outlined in Scheme D Steps 5-7.

TABLE 1

| Scheme | Ketone | Amino acid | Amine | Ex. | Structure | LC | Ret (min) | Obs. Ion |
|---|---|---|---|---|---|---|---|---|
| A | K1 | A1 | M1 | 1 | | 2 | 15.5 | B 544 |
| B | K1 | A1 | M1 | 2 | | 2 | 15.4 | B 554 |
| C | K1 | A1 | M1 | 3 | | 2 | 16.3 | B 540 |
| B | K2 | A1 | M1 | 4 | | 2 | 18.7 & 20.0 | A 598 |

1/1 mix of diastereomers

TABLE 1-continued

| Scheme | Ketone | Amino acid | Amine | Ex. | Structure | LC | Ret (min) | Obs. Ion |
|---|---|---|---|---|---|---|---|---|
| C | K2 | A1 | M1 | 5 | 1/1 mix of diastereomers | 2 | 19.5 & 20.7 | B 582 |
| B | K2 | A2 | M1 | 6 | 1/1 mix of diastereomers | 3 | 17.9 & 19.1 | A 548 |
| A | K2 | A1 | M1 | 7 | 1/1 mix of diastereomers | 2 | 18.9 & 20.2 | B 586 |
| A | K1 | A2 | M1 | 8 |  | 2 | 11.3 | A 496 |

TABLE 1-continued

| Scheme | Ketone | Amino acid | Amine | Ex. | Structure | LC | Ret (min) | Obs. Ion |
|---|---|---|---|---|---|---|---|---|
| C | K1 | A2 | M1 | 9 | | 2 | 12.0 | A 492 |
| B | K1 | A2 | M1 | 10 | | 2 | 11.2 | A 506 |
| A | K3 | A1 | M2 | 11 | racemic | 4 | 18.6 | A 544 |
| A | K2 | A1 | M2 | 12 | | 4 | 12.3 | A 476 |
| A | K2 | A1 | M2 | 13 | racemic | 4 | 15.5 | A 518 |

TABLE 1-continued

| Scheme | Ketone | Amino acid | Amine | Ex. | LC | Ret (min) | Obs. Ion |
|---|---|---|---|---|---|---|---|
| A | K3 | A3 | M2 | 14 | 4 | 17.0 | A 560 |
| A | K3 | A4 | M2 | 15 | 4 | 16.6 | A 544 |
| A | K1 | A3 | M2 | 16 | 4 | 13.1 | A 492 |
| D | K1 | A1 | M3 | 17 | 1 | 4.71 | A 502 |

TABLE 1-continued
| Scheme | Ketone | Amino acid | Amine | Ex. | | LC | LCMS Ret (min) | Obs. Ion |
|---|---|---|---|---|---|---|---|---|
| E | K1 | A5 | M4 | 18 | | 1 | 7.03 | A 594 |
| D | K1 | A1 | M5 | 19 | | 1 | 4.93 | A 504 |
| D | K1 | A1 | M4 | 20 | | 1 | 5.17 | A 518 |
Observed Ion (Obs. Ion) —A— $(M + H)^+$; B — $(M - H)^-$
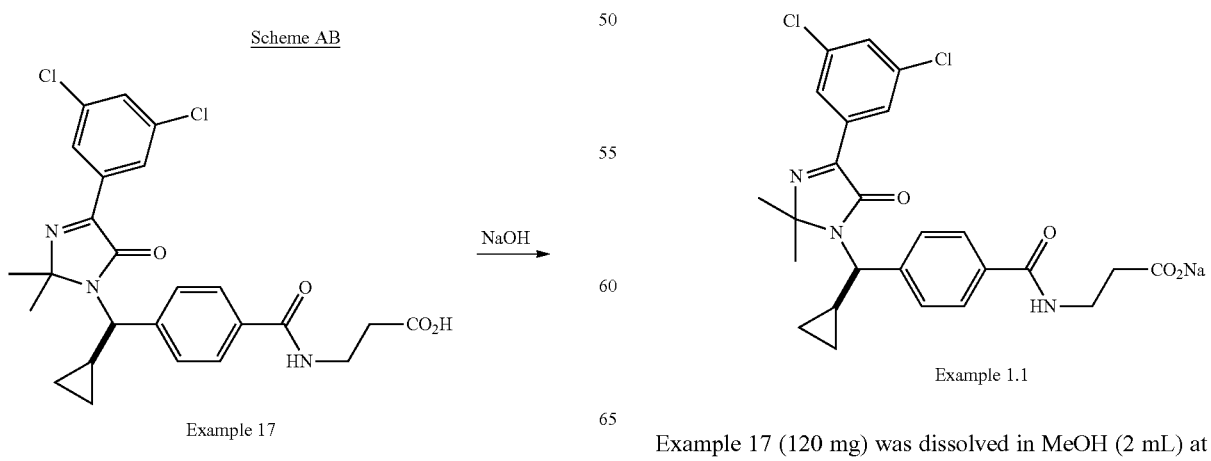
Example 17 (120 mg) was dissolved in MeOH (2 mL) at room temperature followed by adding 1.0 eq of NaOH aqueous solution. The solution was concentrated and dried under high vacuum which provided the desired sodium salt Example 1.1.

TABLE 2

| Ketone | |
|---|---|
| (acetone) | K1 |
| (4-methyl-2-pentanone) | K2 |
| (1-cyclohexylethanone) | K3 |

| Amino acid | |
|---|---|
| 3,5-dichloro-phenyl Boc-NH-CH(CO2H) | A1 |
| 3-fluoro-phenyl Boc-NH-CH(CO2H) | A2 |
| 4-CF3O-phenyl Boc-NH-CH(CO2H) | A3 |
| 3-CF3-phenyl Boc-NH-CH(CO2H) | A4 |

TABLE 2-continued

| | |
|---|---|
| 4-bromo-phenyl Boc-NH-CH(CO2H) | A5 |

| Amine | |
|---|---|
| NH2·HCl, neopentyl, 4-CO2iPr-phenyl | M1 |
| H2N-CH2CH2-(4-CO2Me-phenyl)·HCl | M2 |
| H2N-CH(cyclopropyl)-(4-CO2Me-phenyl)·HCl | M3 |
| NH2·HCl, n-butyl, 4-CO2Me-phenyl | M4 |
| H2N-CH(iPr)-(4-CO2Me-phenyl)·HCl | M5 |

LC-1: Column: Gemini C-18, 50×4.6 mm, 5 micron, obtained from Phenomenex. Mobile phase: A: 0.05% Trifluoroacetic acid in water B: 0.05% Trifluofloacetic acid in acetonitrile Gradient: 90:10 to 5:95 (A:B) over 5 min. Flow rate: 1.0 mL/min UV detection: 254 nm. ESI-MS: Electro Spray Ionization Liquid chromatography-mass spectrometry (ESI-LC/MS) was performed on a PE SCIEX API-150EX, single quadrupole mass spectrometer.

LC-2: HPLC conditions for the retention time were as follows: Column: Luna C18 100 A, 5 μM: A: 0.025% TFA in water B: 0.025% TFA in acetonitrile: Gradient: 98:2 to 15:85 (A:B) over 5 minutes. Gradient: 15:85 to 2:98 over 10 minutes. Hold: 2:98 for 19 minutes followed by a 2 minute gradient back to 98:2 (A:B). Flow rate: 1.0 ml/min UV detection: 254 nm. Mass spec were obtained by one of the following methods: a) Multimode (ESI and APCI). b) ESI LC-3: HPLC conditions for the retention time were as follows: Column: Luna C18 100 A, 5 μM: A: 0.025% TFA in water B: 0.025% TFA in acetonitrile: Gradient: 90:10 to 15:85 (A:B) over 5 minutes. Gradient: 15:85 to 2:98 over 10 minutes. Hold: 2:98 for 19 minutes followed by a 2 minute gradient back to 98:2 (A:B). Flow rate: 1.0 ml/min UV detection: 254 nm. Mass spec were obtained by one of the following methods: a) Multimode (ESI and APCI). b) ESI LC-4: HPLC conditions for the retention time were as follows: Column: Luna C18 100 A, 5 µM: A: 0.025% TFA in water B: 0.025% TFA in acetonitrile: Gradient: 98:2 to 15:85 (A:B) over 10 minutes. Gradient: 15:85 to 2:98 over 10 minutes. Hold: 2:98 for 12 minutes followed by a 2 minute gradient back to 98:2 (A:B). Flow rate: 1.0 ml/min UV detection: 254 nm. Mass spec were obtained by one of the following methods: a) Multimode (ESI and APCI). b) ESI Biological Assays The ability of the compounds of the invention to inhibit the binding of glucagon and their utility in treating or preventing type 2 diabetes mellitus and related conditions can be demonstrated by the following in vitro assays.

Glucagon Receptor Binding Assay

Recombinant human glucagon receptor (huGlucR) membranes and mouse glucagon receptor (mGlucR) membranes were prepared in-house from huGlucR/clone 103c/CHO and mouse liver tissue, respectively. 0.03 ug/li huGluR membranes (or 0.5 ug/ml mGlucR) was incubated in assay buffer containing 0.05 nM $^{125}$I-Glucagon (Perkin Elmer, NEX 207) and varying concentrations of antagonist at room temperature for 60 to 90 (assay buffer: 50 mM HEPES, 1 mM MgCl2, 1 mM CaCl2, 1 mg/ml BSA, COMPLETE protease inhibitor cocktail, pH 7.4). The total volume of the assay was 200 ul. The assay was performed at room temperature using 96-deep well plate. Compound 4c, racemic diastereomer 1 (D1), (1.0 µM final concentration), described by G. H. Ladouceur et al. in Bioorganic and Medicinal Chemistry Letters, 12 (2002), 3421-3424, was used to determine non-specific binding. Following incubation, the reaction was stopped by rapid filtration through Unfilter-96 GF/C glass fiber filter plates (Perkin Elmer) pre-soaked in 0.5% polyethyleneimine. The filtrate was washed using 50 mM Tris-HCl, pH 7.4. Dried filter plates containing bound radioactivity were counted in the presence of scintillation fluid (Microscint 0, Perkin-Elmer) using a Topcount scintillation counter. Data was analyzed using the software program Prism (GraphPad). $IC_{50}$ values were calculated using non-linear regression analysis assuming single site competition.

Inhibition of Glucagon-Stimulated Intracellular cAMP Assay

Recombinant human glucagon receptor-expressing CHO cells were harvested using a non-enzymatic cell dissociation solution (GIBCO 2672), pelleted and resuspended in stimulation buffer (1×HBSS, 5 mM Hepes, 0.1% BSA, pH7.4 in the presence of proteinase inhibitor and phosphodiesterase inhibitors). The adenylate cyclase assay was constructed following the LANCE cAMP Kit (Perkin Elmer, AD0264) instructions. Briefly, cells were preincubated with anti-cAMP antibody and 12 points series diluted compound in stimulation buffer with a final concentration of 3% DMSO for 30 minutes prior to stimulation with 300 pM glucagon for 45 minutes. The reaction was stopped by incubating with the supplied detection buffer containing Europium chelate of the Eu-SA/Biotin-cAMP tracer for 20 hours. The assay was done as triplicates in a 384 well plate. Fluorescence at 665 nm was measured using PheraStar instruments. Basal activity (100% inhibition) was determined using the DMSO control and 0% inhibition was defined as cAMP stimulation produced by 300 pM glucagon. Standard cAMP concentrations were assayed concurrently for conversion of fluorescence signal to cAMP level. Data was analyzed using the software program Prism from GraphPad. $IC_{50}$ values were calculated using non-linear regression analysis assuming single site competition. $IC_{50}$ values for the compounds of the invention shown in the examples measured less than about 10 µM, in preferred embodiments less than about 1 µM, in more preferred embodiments less than about 500 nM.

TABLE 2

| Ex. | Structure | $IC_{50}$ (µM) |
|---|---|---|
| 1 |  | 0.80 |
| 2 |  | 3.7 |
| 3 |  | 6.2 |
| 4 |  1/1 mix of diastereomers | 1.1 |

TABLE 2-continued
| Ex. | | IC$_{50}$ (µM) |
|---|---|---|
| 5 | 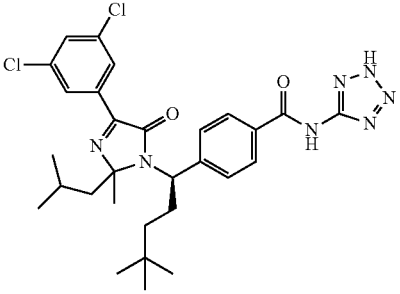<br>1/1 mix of diastereomers | 5.1 |
| 6 | 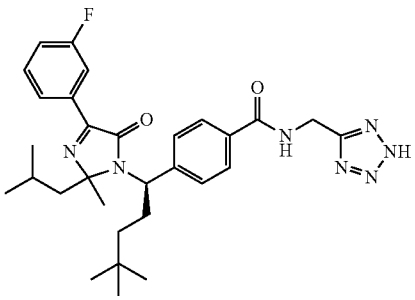<br>1/1 mix of diastereomers | 3.4 |
| 7 | 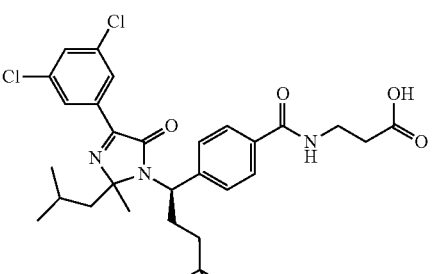<br>1/1 mix of diastereomers | 0.60 |
| 8 | 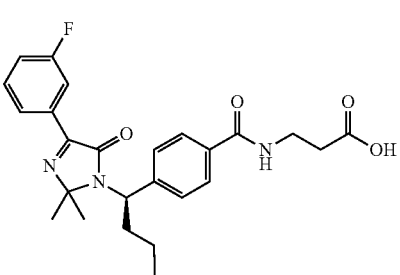 | 4.9 |
| 9 | 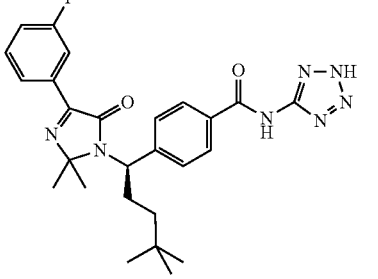 | 5.9 |
| 10 | 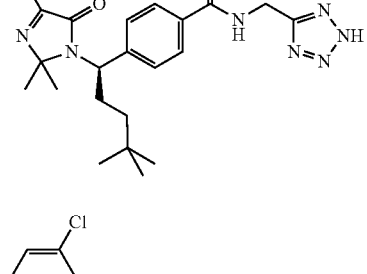 | 8.4 |
| 11 | 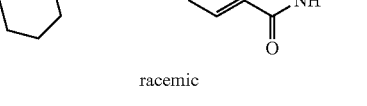<br>racemic | 1.7 |
| 12 |  | 1.7 |
| 13 | 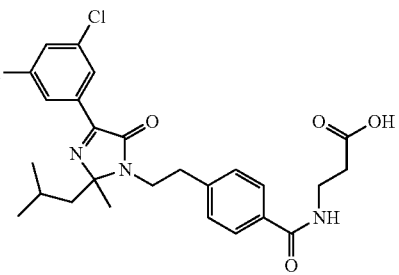<br>racemic | 4.2 |

TABLE 2-continued

| Ex. | Structure | IC$_{50}$ (μM) |
|---|---|---|
| 14 | 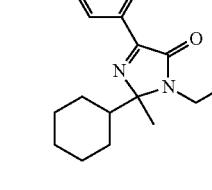 racemic | 5.1 |
| 15 | 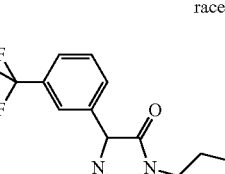 racemic | 3.5 |
| 16 | 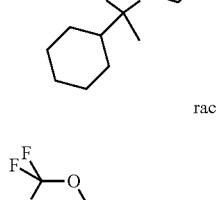 | 8.3 |
| 17 | 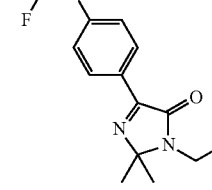 | 1.7 |
| 18 | 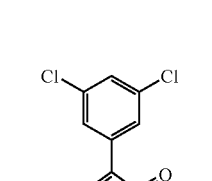 | 1.0 |
| 19 | 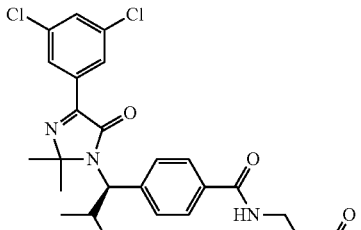 | 1.3 |
| 20 | 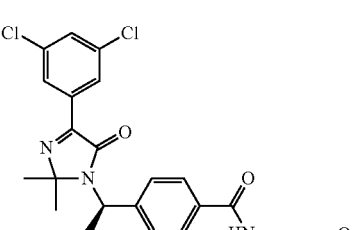 | 2.0 |

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

What is claimed is:

1. A compound represented by Formula (A):

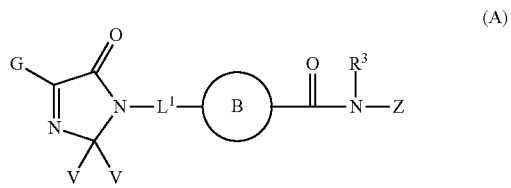

(A)

or a pharmaceutically acceptable salt thereof, wherein:

L$^1$ is selected from the group consisting of a bond, —N(R$^4$)—, —N(R$^4$)—(C(R$^{5A}$)$_2$)—(C(R$^5$)$_2$)$_q$—, —(C(R$^{5A}$)$_2$)—(C(R$^5$)$_2$)$_r$—(C(R$^{5A}$)$_2$)—N(R$^4$)—, —O—, —O—(C(R$^{5A}$)$_2$)—(C(R$^5$)$_2$)$_q$—, —(C(R$^{5A}$)$_2$)—(C(R$^5$)$_2$)$_r$—(C(R$^{5A}$)$_2$)—O— and —(C(R$^{5A}$)$_2$)—(C(R$^5$)$_2$)$_s$—, each q is independently an integer from 0 to 5;
each r is independently an integer from 0 to 3;
s is an integer from 0 to 5;
ring B is a phenyl ring, wherein said phenyl ring is (in addition to the -L$^1$- and —C(O)N(R$^3$)—Z moieties shown) optionally further substituted with one or more substituents R$^a$, wherein each R$^a$ (when present) is independently selected from the group consisting of halo, —OH, —SF$_5$, —OSF$_5$, alkyl, haloalkyl, heteroalkyl, hydroxyalkyl, alkoxy and —O-haloalkyl, or ring B is a 5-membered heteroaromatic ring containing from 1 to 3 ring heteroatoms independently selected from N, O, and S, wherein said 5-membered heteroaromatic ring is (in addition to the -$L^1$- and —C(O)N($R^3$)—Z moieties shown) optionally further substituted with one or more substituents $R^a$, wherein each $R^a$ (when present) is independently selected from the group consisting of halo, —OH, —$SF_5$, —$OSF_5$, alkyl, haloalkyl, heteroalkyl, hydroxyalkyl, alkoxy and —O-haloalkyl, or ring B is a 6-membered heteroaromatic ring containing from 1 to 3 ring nitrogen atoms, wherein said 6-membered heteroaromatic ring is (in addition to -$L^1$- and —C(O)N($R^3$)Z moieties shown) optionally further substituted with one or more substituents $R^a$, wherein each $R^a$ (when present) is independently selected from the group consisting of halo, —OH, —$SF_5$, —$OSF_5$, alkyl, haloalkyl, hydroxyalkyl, alkoxy, and —O-haloalkyl;

each V is independently selected from the group consisting of alkyl, heteroalkyl, alkenyl, alkynyl, cycloalkyl, heterocycloalkyl, cycloalkenyl, heterocycloalkenyl, aryl, and heteroaryl, wherein said heteroalkyl, said heterocycloalkyl, said heterocycloalkenyl, and said heteroaryl of V may only be connected through carbon, and wherein said alkyl, said heteroalkyl, said alkenyl, said alkynyl, said cycloalkyl, said heterocycloalkyl, said cycloalkenyl, said heterocycloalkenyl, said aryl, and said heteroaryl of V are unsubstituted or optionally substituted with one or more groups independently selected from:

(1) halo, —$NH_2$, —OH, —SH, —$SO_2H$, $CO_2H$, —$SF_5$, —$OSF_5$, cyano and —CHO, (2) cycloalkyl, —O-cycloalkyl, —C(O)-cycloalkyl, —$CO_2$-cycloalkyl, —S-cycloalkyl, —S(O)-cycloalkyl, —S(O)$_2$-cycloalkyl, —N($R^1$)-cycloalkyl, —C(O)—N($R^{21}$)-cycloalkyl, —N($R^{21}$)—C(O)-cycloalkyl, —N($R^{21}$)—C(O)—N($R^{21}$)-cycloalkyl, —N($R^{21}$)—S(O)-cycloalkyl, —N($R^{21}$)—S(O)$_2$-cycloalkyl, —N($R^{21}$)—S(O)$_2$—N($R^{21}$)-cycloalkyl, —S(O)—N($R^{21}$)-cycloalkyl and —S(O)$_2$—N($R^{21}$)-cycloalkyl, (3) heterocycloalkyl, —O-heterocycloalkyl, —C(O)-heterocycloalkyl, —$CO_2$-heterocycloalkyl, —S-heterocycloalkyl, —S(O)-heterocycloalkyl, —S(O)$_2$-heterocycloalkyl, —N($R^1$)-heterocycloalkyl, —C(O)—N($R^{21}$)-heterocycloalkyl, —N($R^{21}$)—C(O)-heterocycloalkyl, —N($R^{21}$)—C(O)—N($R^{21}$)-heterocycloalkyl, —N($R^{21}$)—S(O)-heterocycloalkyl, —N($R^{21}$)—S(O)$_2$-heterocycloalkyl, —N($R^{21}$)—S(O)$_2$—N($R^{21}$)-heterocycloalkyl, —S(O)—N($R^{21}$)-heterocycloalkyl and —S(O)$_2$—N($R^{21}$)-heterocycloalkyl, (4) cycloalkenyl, —O-cycloalkenyl, —C(O)-cycloalkenyl, —$CO_2$-cycloalkenyl, —S-cycloalkenyl, —S(O)-cycloalkenyl, —S(O)$_2$-cycloalkenyl, —N($R^1$)-cycloalkenyl, —C(O)—N($R^{21}$)-cycloalkenyl, —N($R^{21}$)—C(O)-cycloalkenyl, —N($R^{21}$)—C(O)—N($R^{21}$)-cycloalkenyl, —N($R^{21}$)—S(O)-cycloalkenyl, —N($R^{21}$)—S(O)$_2$-cycloalkenyl, —N($R^{21}$)—S(O)$_2$—N($R^{21}$)-cycloalkenyl, —S(O)—N($R^{21}$)-cycloalkenyl and —S(O)$_2$—N($R^{21}$)-cycloalkenyl, (5) heterocycloalkenyl, —O-heterocycloalkenyl, —C(O)-heterocycloalkenyl, —$CO_2$-heterocycloalkenyl, —S-heterocycloalkenyl, —S(O)-heterocycloalkenyl, —S(O)$_2$-heterocycloalkenyl, —N($R^1$)-heterocycloalkenyl, —C(O)—N($R^{21}$)-heterocycloalkenyl, —N($R^{21}$)—C(O)-heterocycloalkenyl, —N($R^{21}$)—C(O)—N($R^{21}$)-heterocycloalkenyl, —N($R^{21}$)—S(O)-heterocycloalkenyl, —N($R^{21}$)—S(O)$_2$-heterocycloalkenyl, —N($R^{21}$)—S(O)$_2$—N($R^{21}$)-heterocycloalkenyl, —S(O)—N($R^{21}$)-heterocycloalkenyl and —S(O)$_2$—N($R^{21}$)-heterocycloalkenyl, (6) alkyl, —O-alkyl, —C(O)-alkyl, —$CO_2$-alkyl, —S-alkyl, —S(O)-alkyl, —S(O)$_2$-alkyl, —N($R^1$)-alkyl, —C(O)—N($R^{21}$)-alkyl, —N($R^{21}$)—C(O)-alkyl, —N($R^{21}$)—C(O)—N($R^{21}$)-alkyl, —N($R^{21}$)—S(O)-alkyl, —N($R^{21}$)—S(O)$_2$-alkyl, —N($R^{21}$)—S(O)$_2$—N($R^{21}$)-alkyl, —S(O)—N($R^{21}$)-alkyl and —S(O)$_2$—N($R^{21}$)-alkyl, (7) heteroalkyl, —O-heteroalkyl, —C(O)-heteroalkyl, —$CO_2$-heteroalkyl, —S-heteroalkyl, —S(O)-heteroalkyl, —S(O)$_2$-heteroalkyl, —N($R^1$)-heteroalkyl, —C(O)—N($R^{21}$)-heteroalkyl, —N($R^{21}$)—C(O)-heteroalkyl, —N($R^{21}$)—C(O)—N($R^{21}$)-heteroalkyl, —N($R^{21}$)—S(O)-heteroalkyl, —N($R^{21}$)—S(O)$_2$-heteroalkyl, —N($R^{21}$)—S(O)$_2$—N($R^{21}$)-heteroalkyl, —S(O)—N($R^{21}$)-heteroalkyl and —S(O)$_2$—N($R^{21}$)-heteroalkyl, (8) alkenyl, —O-alkenyl, —C(O)-alkenyl, —$CO_2$-alkenyl, —S-alkenyl, —S(O)-alkenyl, —S(O)$_2$-alkenyl, —N($R^1$)-alkenyl, —C(O)—N($R^{21}$)-alkenyl, —N($R^{21}$)—C(O)-alkenyl, —N($R^{21}$)—C(O)—N($R^{21}$)-alkenyl, —N($R^{21}$)—S(O)-alkenyl, —N($R^{21}$)—S(O)$_2$-alkenyl, —N($R^{21}$)—S(O)$_2$—N($R^{21}$)-alkenyl, —S(O)—N($R^{21}$)-alkenyl and —S(O)$_2$—N($R^{21}$)-alkenyl, (9) alkynyl, —O-alkynyl, —C(O)-alkynyl, —$CO_2$-alkynyl, —S-alkynyl, —S(O)-alkynyl, —S(O)$_2$-alkynyl, —N($R^1$)-alkynyl, —C(O)—N($R^{21}$)-alkynyl, —N($R^{21}$)—C(O)-alkynyl, —N($R^{21}$)—C(O)—N($R^{21}$)-alkynyl, —N($R^{21}$)—S(O)-alkynyl, —N($R^{21}$)—S(O)$_2$-alkynyl, —N($R^{21}$)—S(O)$_2$—N($R^{21}$)-alkynyl, —S(O)—N($R^{21}$)-alkynyl and —S(O)$_2$—N($R^{21}$)-alkynyl,

(10) aryl, —O-aryl, —C(O)-aryl, —$CO_2$-aryl, —S-aryl, —S(O)-aryl, —S(O)$_2$-aryl, —N($R^1$)-aryl, —C(O)—N($R^{21}$)-aryl, —N($R^{21}$)—C(O)-aryl, —N($R^{21}$)—C(O)—N($R^{21}$)-aryl, —N($R^{21}$)—S(O)-aryl, —N($R^{21}$)—S(O)$_2$-aryl, —N($R^{21}$)—S(O)$_2$—N($R^{21}$)-aryl, —S(O)—N($R^{21}$)-aryl and —S(O)$_2$—N($R^{21}$)-aryl, or

(11) heteroaryl, —O-heteroaryl, —C(O)-heteroaryl, —$CO_2$-heteroaryl, —S-heteroaryl, —S(O)-heteroaryl, —S(O)$_2$-heteroaryl, —N($R^{21}$)-heteroaryl, —C(O)—N($R^{21}$)-heteroaryl, —N($R^{21}$)—C(O)-heteroaryl, —N($R^{21}$)—C(O)—N($R^{21}$)-heteroaryl, —N($R^{21}$)—S(O)-heteroaryl, —N($R^{21}$)—S(O)$_2$-heteroaryl, —N($R^{21}$)—S(O)$_2$—N($R^{21}$)-heteroaryl, —S(O)—N($R^{21}$)-heteroaryl and —S(O)$_2$—N($R^{21}$)-heteroaryl, wherein said heteroalkyl of (7), said heterocycloalkyl of (3), said heterocycloalkenyl of (5), and said heteroaryl of (11) may be connected through any available carbon or heteroatom, and wherein said alkyl, said heteroalkyl, said cycloalkyl, said heterocycloalkyl, said aryl, said heteroaryl, said alkenyl, said alkynyl, said cycloalkenyl, and said heterocycloalkenyl of (1) through (11) are unsubstituted or substituted with one or more groups independently selected from $R^2$;

G is selected from the group consisting of:

(1a) hydrogen, halo, —$NH_2$, —OH, —SH, —$SO_2H$, $CO_2H$, —$SF_5$, —$OSF_5$, cyano and —CHO, (2a) cycloalkyl, —O-cycloalkyl, —C(O)-cycloalkyl, —$CO_2$-cycloalkyl, —S-cycloalkyl, —S(O)-cycloalkyl, —S(O)$_2$-cycloalkyl, —N($R^1$)-cycloalkyl, —C(O)—N($R^{21}$)-cycloalkyl, —N($R^{21}$)—C(O)-cycloalkyl, —N($R^{21}$)—C(O)—N($R^{21}$)-cycloalkyl, —N($R^{21}$)—S(O)-cycloalkyl, —N($R^{21}$)—S(O)$_2$-cycloalkyl, —N($R^{21}$)—S(O)$_2$—N($R^{21}$)-cycloalkyl, —S(O)—N($R^{21}$)-cycloalkyl and —S(O)$_2$—N($R^{21}$)-cycloalkyl, (3a) heterocycloalkyl, —O-heterocycloalkyl, —C(O)-heterocycloalkyl, —CO$_2$-heterocycloalkyl, —S-heterocycloalkyl, —S(O)-heterocycloalkyl, —S(O)$_2$-heterocycloalkyl, —N($R^1$)-heterocycloalkyl, —C(O)—N($R^{21}$)-heterocycloalkyl, —N($R^{21}$)—C(O)-heterocycloalkyl, —N($R^{21}$)—C(O)—N($R^{21}$)-heterocycloalkyl, —N($R^{21}$)—S(O)-heterocycloalkyl, —N($R^{21}$)—S(O)$_2$-heterocycloalkyl, —N($R^{21}$)—S(O)$_2$—N($R^{21}$)-heterocycloalkyl, —S(O)—N($R^{21}$)-heterocycloalkyl and —S(O)$_2$—N($R^{21}$)-heterocycloalkyl, (4a) cycloalkenyl, —O-cycloalkenyl, —C(O)-cycloalkenyl, —CO$_2$-cycloalkenyl, —S-cycloalkenyl, —S(O)-cycloalkenyl, —S(O)$_2$-cycloalkenyl, —N($R^1$)-cycloalkenyl, —C(O)—N($R^{21}$)-cycloalkenyl, —N($R^{21}$)—C(O)-cycloalkenyl, —N($R^{21}$)—C(O)—N($R^{21}$)-cycloalkenyl, —N($R^{21}$)—S(O)-cycloalkenyl, —N($R^{21}$)—S(O)$_2$-cycloalkenyl, —N($R^{21}$)—S(O)$_2$—N($R^{21}$)-cycloalkenyl, —S(O)—N($R^{21}$)-cycloalkenyl and —S(O)$_2$—N($R^{21}$)-cycloalkenyl, (5a) heterocycloalkenyl, —O-heterocycloalkenyl, —C(O)-heterocycloalkenyl, —CO$_2$-heterocycloalkenyl, —S-heterocycloalkenyl, —S(O)-heterocycloalkenyl, —S(O)$_2$-heterocycloalkenyl, —N($R^1$)-heterocycloalkenyl, —C(O)—N($R^{21}$)-heterocycloalkenyl, —N($R^{21}$)—C(O)-heterocycloalkenyl, —N($R^{21}$)—C(O)—N($R^{21}$)-heterocycloalkenyl, —N($R^{21}$)—S(O)-heterocycloalkenyl, —N($R^{21}$)—S(O)$_2$-heterocycloalkenyl, —N($R^{21}$)—S(O)$_2$—N($R^{21}$)-heterocycloalkenyl, —S(O)—N($R^{21}$)-heterocycloalkenyl and —S(O)$_2$—N($R^{21}$)-heterocycloalkenyl, (6a) alkyl, —O-alkyl, —C(O)-alkyl, —CO$_2$-alkyl, —S-alkyl, —S(O)-alkyl, —S(O)$_2$-alkyl, —N($R^1$)-alkyl, —C(O)—N($R^{21}$)-alkyl, —N($R^{21}$)—C(O)-alkyl, —N($R^{21}$)—C(O)—N($R^{21}$)-alkyl, —N($R^{21}$)—S(O)-alkyl, —N($R^{21}$)—S(O)$_2$-alkyl —N($R^{21}$)—S(O)$_2$—N($R^{21}$)-alkyl, —S(O)—N($R^{21}$)-alkyl and —S(O)$_2$—N($R^{21}$)-alkyl, (7a) heteroalkyl, —O-heteroalkyl, —C(O)-heteroalkyl, —CO$_2$-heteroalkyl, —S-heteroalkyl, —S(O)-heteroalkyl, —S(O)$_2$-heteroalkyl, —N($R^1$)-heteroalkyl, —C(O)—N($R^{21}$)-heteroalkyl, —N($R^{21}$)—C(O)-heteroalkyl, —N($R^{21}$)—C(O)—N($R^{21}$)-heteroalkyl, —N($R^{21}$)—S(O)-heteroalkyl, —N($R^{21}$)—S(O)$_2$-heteroalkyl, —N($R^{21}$)—S(O)$_2$—N($R^{21}$)-heteroalkyl, —S(O)—N($R^{21}$)-heteroalkyl and —S(O)$_2$—N($R^{21}$)-heteroalkyl, (8a) alkenyl, —O-alkenyl, —C(O)-alkenyl, —CO$_2$-alkenyl, —S-alkenyl, —S(O)-alkenyl, —S(O)$_2$-alkenyl, —N($R^1$)-alkenyl, —C(O)—N($R^{21}$)-alkenyl, —N($R^{21}$)—C(O)-alkenyl, —N($R^{21}$)—C(O)—N($R^{21}$)-alkenyl, —N($R^{21}$)—S(O)-alkenyl, —N($R^{21}$)—S(O)$_2$-alkenyl, —N($R^{21}$)—S(O)$_2$—N($R^{21}$)-alkenyl, —S(O)—N($R^{21}$)-alkenyl and —S(O)$_2$—N($R^{21}$)-alkenyl, (9a) alkynyl, —O-alkynyl, —C(O)-alkynyl, —CO$_2$-alkynyl, —S-alkynyl, —S(O)-alkynyl, —S(O)$_2$-alkynyl, —N($R^1$)-alkynyl, —C(O)—N($R^{21}$)-alkynyl, —N($R^{21}$)—C(O)-alkynyl, —N($R^{21}$)—C(O)—N($R^{21}$)-alkynyl, —N($R^{21}$)—S(O)-alkynyl, —N($R^{21}$)—S(O)$_2$-alkynyl, —N($R^{21}$)—S(O)$_2$—N($R^{21}$)-alkynyl, —S(O)—N($R^{21}$)-alkynyl and —S(O)$_2$—N($R^{21}$)-alkynyl, (10a) aryl, —O-aryl, —C(O)-aryl, —CO$_2$-aryl, —S-aryl, —S(O)-aryl, —S(O)$_2$-aryl, —N($R^1$)-aryl, —C(O)—N($R^{21}$)-aryl, —N($R^{21}$)—C(O)-aryl, —N($R^{21}$)—C(O)—N($R^{21}$)-aryl, —N($R^{21}$)—S(O)-aryl, —N($R^{21}$)—S(O)$_2$-aryl, —N($R^{21}$)—S(O)$_2$—N($R^{21}$)-aryl, —S(O)—N($R^{21}$)-aryl and —S(O)$_2$—N($R^{21}$)-aryl, or (11a) heteroaryl, —O-heteroaryl, —C(O)-heteroaryl, —CO$_2$-heteroaryl, —S-heteroaryl, —S(O)-heteroaryl, —S(O)$_2$-heteroaryl, —N($R^1$)-heteroaryl, —C(O)—N($R^{21}$)-heteroaryl, —N($R^{21}$)—C(O)-heteroaryl, —N($R^{21}$)—C(O)—N($R^{21}$)-heteroaryl, —N($R^{21}$)—S(O)-heteroaryl, —N($R^{21}$)—S(O)$_2$-heteroaryl, —N($R^{21}$)—S(O)$_2$—N($R^{21}$)-heteroaryl, —S(O)—N($R^{21}$)-heteroaryl and —S(O)$_2$—N($R^{21}$)-heteroaryl;

wherein said heteroalkyl, said heterocycloalkyl, said heterocycloalkenyl, and said heteroaryl of G may be connected through any available carbon or heteroatom, and wherein said alkyl, said heteroalkyl, said cycloalkyl, said heterocycloalkyl, said aryl, said heteroaryl, said alkenyl, said alkynyl, said cycloalkyl, and said heterocycloalkenyl of G are unsubstituted or substituted with one or more groups independently selected from $R^2$;

each $R^1$ is independently selected from:

(1b) hydrogen and —CHO, (2b) cycloalkyl, —C(O)-cycloalkyl, —CO$_2$-cycloalkyl, —S(O)-cycloalkyl and —S(O)$_2$-cycloalkyl, (3b) heterocycloalkyl, —C(O)-heterocycloalkyl, —CO$_2$-heterocycloalkyl, —S(O)-heterocycloalkyl and —S(O)$_2$-heterocycloalkyl, (4 b) cycloalkenyl, —C(O)-cycloalkenyl, —CO$_2$-cycloalkenyl, —S(O)-cycloalkenyl and —S(O)$_2$-cycloalkenyl, (5b) heterocycloalkenyl, —C(O)-heterocycloalkenyl, —CO$_2$-heterocycloalkenyl, —S(O)-heterocycloalkenyl and —S(O)$_2$-heterocycloalkenyl, (6b) alkyl, —C(O)-alkyl, —CO$_2$-alkyl, —S(O)-alkyl and —S(O)$_2$-alkyl, (7b) heteroalkyl, —C(O)-heteroalkyl, —CO$_2$-heteroalkyl, —S(O)-heteroalkyl and —S(O)$_2$-heteroalkyl, (8b) alkenyl, —C(O)-alkenyl, —CO$_2$-alkenyl, —S(O)-alkenyl and —S(O)$_2$-alkenyl, (9b) alkynyl, —C(O)-alkynyl, —CO$_2$-alkynyl, —S(O)-alkynyl and —S(O)$_2$-alkynyl, (10b) aryl, —C(O)-aryl, —CO$_2$-aryl, —S(O)-aryl and —S(O)$_2$-aryl, or (11b) heteroaryl, —C(O)-heteroaryl, —CO$_2$-heteroaryl, —S(O)-heteroaryl and —S(O)$_2$-heteroaryl, wherein said heteroalkyl, said heterocycloalkyl, said heterocycloalkenyl, and said heteroaryl of $R^1$ may be connected through any available carbon or heteroatom, and wherein said alkyl, said heteroalkyl, said cycloalkyl, said heterocycloalkyl, said aryl, said heteroaryl, said alkenyl, said alkynyl, said cycloalkyl, and said heterocycloalkenyl of $R^1$ are unsubstituted or substituted with one or more groups independently selected from $R^2$;

each $R^{21}$ is independently selected from H and $C_{1-6}$alkyl;

each $R^2$ is independently selected from:

(1c) halo, —NH$_2$, —OH, —SH, —SO$_2$H, CO$_2$H, —SF$_5$, —OSF$_5$, cyano and —CHO, (2c) cycloalkyl, —O-cycloalkyl, —C(O)-cycloalkyl, —CO$_2$-cycloalkyl, —S-cycloalkyl, —S(O)-cycloalkyl, —S(O)$_2$-cycloalkyl, —N($R^6$)-cycloalkyl, —C(O)—N($R^{21}$)-cycloalkyl, —N($R^{21}$)—C(O)-cycloalkyl, —N($R^{21}$)—C(O)—N($R^{21}$)-cycloalkyl, —N($R^{21}$)—S(O)-cycloalkyl, —N($R^{21}$)—S(O)$_2$-cycloalkyl, —N($R^{21}$)—S(O)$_2$—N($R^{21}$)-cycloalkyl, —S(O)—N($R^{21}$)-cycloalkyl and —S(O)$_2$—N($R^{21}$)-cycloalkyl, (3c) heterocycloalkyl, —O-heterocycloalkyl, —C(O)-heterocycloalkyl, —CO$_2$-heterocycloalkyl, —S-heterocycloalkyl, —S(O)-heterocycloalkyl, —S(O)$_2$-heterocycloalkyl, —N($R^6$)-heterocycloalkyl, —C(O)—N($R^{21}$)-heterocycloalkyl, —N($R^{21}$)—C(O)-heterocycloalkyl, —N(R²¹)—C(O)—N(R²¹)-heterocycloalkyl, —N(R²¹)—S(O)-heterocycloalkyl, —N(R²¹)—S(O)₂-heterocycloalkyl, —N(R²¹)—S(O)₂—N(R²¹)-heterocycloalkyl, —S(O)—N(R²¹)-heterocycloalkyl and —S(O)₂—N(R²¹)-heterocycloalkyl, (4c) cycloalkenyl, —O-cycloalkenyl, —C(O)-cycloalkenyl, —CO₂-cycloalkenyl, —S-cycloalkenyl, —S(O)-cycloalkenyl, —S(O)₂-cycloalkenyl, —N(R⁶)-cycloalkenyl, —C(O)—N(R²¹)-cycloalkenyl, —N(R²¹)—C(O)-cycloalkenyl, —N(R²¹)—C(O)—N(R²¹)-cycloalkenyl, —N(R²¹)—S(O)-cycloalkenyl, —N(R²¹)—S(O)₂-cycloalkenyl, —N(R²¹)—S(O)₂—N(R²¹)-cycloalkenyl, —S(O)—N(R²¹)-cycloalkenyl and —S(O)₂—N(R²¹)-cycloalkenyl, (5c) heterocycloalkenyl, —O-heterocycloalkenyl, —C(O)-heterocycloalkenyl, —CO₂-heterocycloalkenyl, —S-heterocycloalkenyl, —S(O)-heterocycloalkenyl, —S(O)₂-heterocycloalkenyl, —N(R⁶)-heterocycloalkenyl, —C(O)—N(R²¹)-heterocycloalkenyl, —N(R²¹)—C(O)-heterocycloalkenyl, —N(R²¹)—C(O)—N(R²¹)-heterocycloalkenyl, —N(R²¹)—S(O)-heterocycloalkenyl, —N(R²¹)—S(O)₂-heterocycloalkenyl, —N(R²¹)—S(O)₂—N(R²¹)-heterocycloalkenyl, —S(O)—N(R²¹)-heterocycloalkenyl and —S(O)₂—N(R²¹)— heterocycloalkenyl, (6c) alkyl, —O-alkyl, —C(O)-alkyl, —CO₂-alkyl, —S-alkyl, —S(O)-alkyl, —S(O)₂-alkyl, —N(R⁶)-alkyl, —C(O)—N(R²¹)-alkyl, —N(R²¹)—C(O)-alkyl, —N(R²¹)—C(O)—N(R²¹)-alkyl, —N(R²¹)—S(O)-alkyl, —N(R²¹)—S(O)₂-alkyl, —N(R²¹)—S(O)₂—N(R²¹)-alkyl, —S(O)—N(R²¹)-alkyl and —S(O)₂—N(R²¹)-alkyl, (7c) heteroalkyl, —O-heteroalkyl, —C(O)-heteroalkyl, —CO₂-heteroalkyl, —S-heteroalkyl, —S(O)-heteroalkyl, —S(O)₂-heteroalkyl, —N(R⁶)-heteroalkyl, —C(O)—N(R²¹)-heteroalkyl, —N(R²¹)—C(O)-heteroalkyl, —N(R²¹)—C(O)—N(R²¹)-heteroalkyl, —N(R²¹)—S(O)-heteroalkyl, —N(R²¹)—S(O)₂-heteroalkyl, —N(R²¹)—S(O)₂—N(R²¹)-heteroalkyl, —S(O)—N(R²¹)-heteroalkyl and —S(O)₂—N(R²¹)-heteroalkyl, (8c) alkenyl, —O-alkenyl, —C(O)-alkenyl, —CO₂-alkenyl, —S-alkenyl, —S(O)-alkenyl, —S(O)₂-alkenyl, —N(R⁶)-alkenyl, —C(O)—N(R²¹)-alkenyl, —N(R²¹)—C(O)-alkenyl, —N(R²¹)—C(O)—N(R²¹)-alkenyl, —N(R²¹)—S(O)-alkenyl, —N(R²¹)—S(O)₂-alkenyl, —N(R²¹)—S(O)₂—N(R²¹)-alkenyl, —S(O)—N(R²¹)-alkenyl and —S(O)₂—N(R²¹)-alkenyl, (9c) alkynyl, —O-alkynyl, —C(O)-alkynyl, —CO₂-alkynyl, —S-alkynyl, —S(O)-alkynyl, —S(O)₂-alkynyl, —N(R⁶)-alkynyl, —C(O)—N(R²¹)-alkynyl, —N(R²¹)—C(O)-alkynyl, —N(R²¹)—C(O)—N(R²¹)-alkynyl, —N(R²¹)—S(O)-alkynyl, —N(R²¹)—S(O)₂-alkynyl, —N(R²¹)—S(O)₂—N(R²¹)-alkynyl, —S(O)—N(R²¹)-alkynyl and —S(O)₂—N(R²¹)-alkynyl, (10c) aryl, —O-aryl, —C(O)-aryl, —CO₂-aryl, —S-aryl, —S(O)-aryl, —S(O)₂-aryl, —N(R⁶)-aryl, —C(O)—N(R²¹)-aryl, —N(R²¹) C(O)-aryl, —N(R²¹)—C(O)—N(R²¹)-aryl, —N(R²¹)—S(O)-aryl, —N(R²¹)—S(O)₂-aryl, —N(R²¹)—S(O)₂—N(R²¹)-aryl, —S(O)—N(R²¹)-aryl and —S(O)₂—N(R²¹)-aryl, (11c) heteroaryl, —O-heteroaryl, —C(O)-heteroaryl, —CO₂-heteroaryl, —S-heteroaryl, —S(O)-heteroaryl, —S(O)₂-heteroaryl, —N(R⁶)-heteroaryl, —C(O)—N(R²¹)-heteroaryl, —N(R²¹)—C(O)-heteroaryl, —N(R²¹)—C(O)—N(R²¹)-heteroaryl, —N(R²¹)—S(O)-heteroaryl, —N(R²¹)—S(O)₂-heteroaryl, —N(R²¹)—S(O)₂—N(R²¹)-heteroaryl, —S(O)—N(R²¹)-heteroaryl and —S(O)₂—N(R²¹)-heteroaryl, wherein said heteroalkyl, said heterocycloalkyl, said heterocycloalkenyl, and said heteroaryl of $R^2$ may be connected through any available carbon or heteroatom, and wherein said alkyl, said heteroalkyl, said cycloalkyl, said heterocycloalkyl, said aryl, said heteroaryl, said alkenyl, said alkynyl, said cycloalkenyl, and said heterocycloalkyl of $R^2$ are unsubstituted or substituted with one or more groups independently selected from $R^7$;

$R^3$ is selected from H, methyl, ethyl, n-propyl and isopropyl;

Z is a moiety selected from —(C(R¹¹)₂)—(C(R¹²R¹³))ₘ—C(O)OH, —(C(R¹¹)₂)—(C(R¹⁴)₂)ₙ—C(O)OH, —(C(R¹¹)₂)—(C(R¹²R¹³))ₘ—C(O)Oalkyl, —(C(R¹¹)₂)—(C(R¹⁴)₂)ₙ—C(O)Oalkyl,

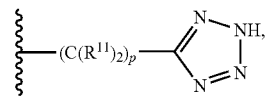

—(C(R¹¹)₂)—(C(R¹²R¹³))ₘ-Q,     and     —(C(R¹¹)₂)—(C(R¹⁴)₂)ₙ-Q, wherein Q is a moiety selected from the group consisting of:

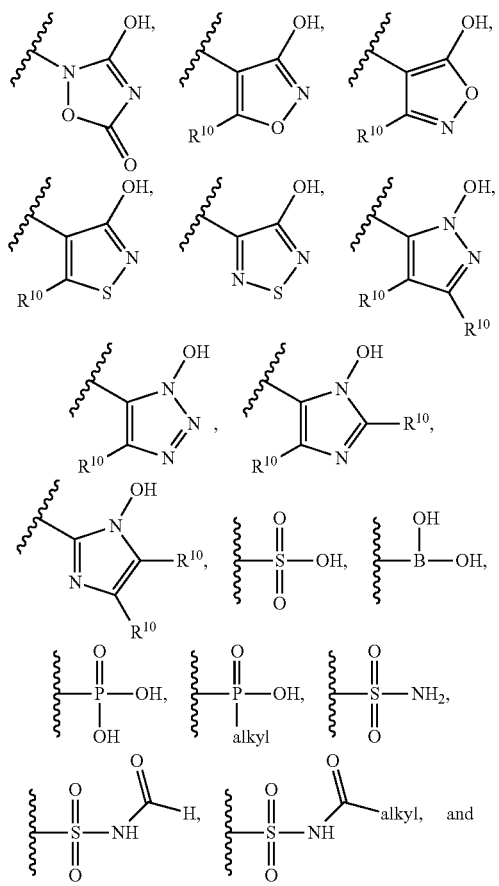

-continued

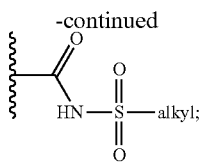

wherein each $R^{10}$ is independently H or alkyl;
m is an integer from 0 to 5;
n is an integer from 0 to 5;
p is an integer from 0 to 5;
each $R^4$ is independently selected from H, —OH, $C_{1-3}$ alkyl, haloalkyl, alkoxy, heteroalkyl, cyano-substituted $C_{1-3}$ alkyl, hydroxy-substituted $C_{1-3}$ alkyl, cycloalkyl, —O-cycloalkyl, —O-alkyl-cycloalkyl, heterocycloalkyl, —O-heterocycloalkyl, and —O-alkyl-heterocycloalkyl;
each $R^{5A}$ is independently selected from H, alkyl, haloalkyl, heteroalkyl, cyano-substituted alkyl, hydroxy-substituted alkyl, cycloalkyl, -alkyl-cycloalkyl, heterocycloalkyl, and -alkyl-heterocycloalkyl, or, alternatively, two $R^{5A}$ groups are taken together with the carbon atom to which they are attached to form a carbonyl group, a spirocycloalkyl group, a spiroheterocycloalkyl group, an oxime group, or a substituted oxime group, said oxime substituents being independently selected from alkyl, haloalkyl, hydroxyl-substituted alkyl, and cycloalkyl;
each $R^5$ is independently selected from H, —OH, alkyl, haloalkyl, alkoxy, heteroalkyl, cyano-substituted alkyl, hydroxy-substituted alkyl, cycloalkyl, -alkyl-cycloalkyl, —O-cycloalkyl, —O-alkyl-cycloalkyl, heterocycloalkyl, -alkyl-heterocycloalkyl, —O-heterocycloalkyl, and —O-alkyl-heterocycloalkyl,
or, alternatively, two $R^5$ groups bound to the same carbon atom are taken together with the carbon atom to which they are attached to form a carbonyl group, a spirocycloalkyl group, a spiroheterocycloalkyl group, an oxime group, or a substituted oxime group, said oxime substituents being independently selected from alkyl, haloalkyl, hydroxyl-substituted alkyl, and cycloalkyl;
each $R^6$ is independently selected from:
(1d) hydrogen, and —CHO,
(2d) cycloalkyl, —C(O)-cycloalkyl, —CO₂-cycloalkyl, —S(O)-cycloalkyl, and —S(O)₂-cycloalkyl,
(3d) heterocycloalkyl, —C(O)-heterocycloalkyl, —CO₂-heterocycloalkyl, —S(O)-heterocycloalkyl, and —S(O)₂-heterocycloalkyl,
(4d) cycloalkenyl, —C(O)-cycloalkenyl, —CO₂-cycloalkenyl, —S(O)-cycloalkenyl, and —S(O)₂-cycloalkenyl,
(5d) heterocycloalkenyl, —C(O)-heterocycloalkenyl, —CO₂-heterocycloalkenyl, —S(O)-heterocycloalkenyl, and —S(O)₂-heterocycloalkenyl,
(6d) alkyl, —C(O)-alkyl, —CO₂-alkyl, —S(O)-alkyl, and —S(O)₂-alkyl,
(7d) heteroalkyl, —C(O)-heteroalkyl, —CO₂-heteroalkyl, —S(O)-heteroalkyl, and —S(O)₂-heteroalkyl,
(8d) alkenyl, —C(O)-alkenyl, —CO₂-alkenyl, —S(O)-alkenyl, and —S(O)₂-alkenyl,
(9d) alkynyl, —C(O)-alkynyl, —CO₂-alkynyl, —S(O)-alkynyl, and —S(O)₂-alkynyl, (10d) aryl, —C(O)-aryl, —CO₂-aryl, —S(O)-aryl, and —S(O)₂-aryl,
(11d) heteroaryl, —C(O)-heteroaryl, —CO₂-heteroaryl, —S(O)-heteroaryl, and —S(O)₂-heteroaryl;

each $R^7$ is independently selected from:
(1e) halo, —NH₂, —OH, —SH, —SO₂H, CO₂H, —SF₅, —OSF₅, cyano and —CHO,
(2e) cycloalkyl, —O-cycloalkyl, —C(O)-cycloalkyl, —CO₂-cycloalkyl, —S-cycloalkyl, —S(O)-cycloalkyl, —S(O)₂-cycloalkyl, —N(R⁶)-cycloalkyl, —C(O)—N(R²¹)-cycloalkyl, —N(R²¹)—C(O)-cycloalkyl, —N(R²¹)—C(O)—N(R²¹)-cycloalkyl, —N(R²¹)—S(O)-cycloalkyl, —N(R²¹)—S(O)₂-cycloalkyl, —N(R²¹)—S(O)₂—N(R²¹)-cycloalkyl, —S(O)—N(R²¹)-cycloalkyl and —S(O)₂—N(R²¹)-cycloalkyl,
(3e) heterocycloalkyl, —O-heterocycloalkyl, —C(O)-heterocycloalkyl, —CO₂-heterocycloalkyl, —S-heterocycloalkyl, —S(O)-heterocycloalkyl, —S(O)₂-heterocycloalkyl, —N(R⁶)-heterocycloalkyl, —C(O)—N(R²¹)-heterocycloalkyl, —N(R²¹)—C(O)-heterocycloalkyl, —N(R²¹)—C(O)—N(R²¹)-heterocycloalkyl, —N(R²¹)—S(O)-heterocycloalkyl, —N(R²¹)—S(O)₂-heterocycloalkyl, —N(R²¹)—S(O)₂—N(R²¹)-heterocycloalkyl, —S(O)—N(R²¹)-heterocycloalkyl and —S(O)₂—N(R²¹)-heterocycloalkyl,
(4e) cycloalkenyl, —O-cycloalkenyl, —C(O)-cycloalkenyl, —CO₂-cycloalkenyl, —S-cycloalkenyl, —S(O)-cycloalkenyl, —S(O)₂-cycloalkenyl, —N(R⁶)-cycloalkenyl, —C(O)—N(R²¹)-cycloalkenyl, —N(R²¹)—C(O)-cycloalkenyl, —N(R²¹)—C(O)—N(R²¹)-cycloalkenyl, —N(R²¹)—S(O)-cycloalkenyl, —N(R²¹)—S(O)₂-cycloalkenyl, —N(R²¹)—S(O)₂—N(R²¹)-cycloalkenyl, —S(O)—N(R²¹)-cycloalkenyl and —S(O)₂—N(R²¹)-cycloalkenyl,
(5e) heterocycloalkenyl, —O-heterocycloalkenyl, —C(O)-heterocycloalkenyl, —CO₂-heterocycloalkenyl, —S-heterocycloalkenyl, —S(O)-heterocycloalkenyl, —S(O)₂-heterocycloalkenyl, —N(R⁶)-heterocycloalkenyl, —C(O)—N(R²¹)-heterocycloalkenyl, —N(R²¹)—C(O)-heterocycloalkenyl, —N(R²¹)—C(O)—N(R²¹)-heterocycloalkenyl, —N(R²¹)—S(O)-heterocycloalkenyl, —N(R²¹)—S(O)₂-heterocycloalkenyl, —N(R²¹)—S(O)₂—N(R²¹)—heterocycloalkenyl, —S(O)—N(R²¹)-heterocycloalkenyl and —S(O)₂—N(R²¹)— heterocycloalkenyl,
(6e) alkyl, —O-alkyl, —C(O)-alkyl, —CO₂-alkyl, —S-alkyl, —S(O)-alkyl, —S(O)₂-alkyl, —N(R⁶)-alkyl, —C(O)—N(R²¹)-alkyl, —N(R²¹)—C(O)-alkyl, —N(R²¹)—C(O)—N(R²¹)-alkyl, —N(R²¹)—S(O)-alkyl, —N(R²¹)—S(O)₂-alkyl, —N(R²¹)—S(O)₂—N(R²¹)-alkyl, —S(O)—N(R²¹)-alkyl and —S(O)₂—N(R²¹)-alkyl,
(7e) heteroalkyl, —O-heteroalkyl, —C(O)-heteroalkyl, —CO₂-heteroalkyl, —S-heteroalkyl, —S(O)-heteroalkyl, —S(O)₂-heteroalkyl, —N(R⁶)-heteroalkyl, —C(O)—N(R²¹)-heteroalkyl, —N(R²¹)—C(O)-heteroalkyl, —N(R²¹)—C(O)—N(R²¹)-heteroalkyl, —N(R²¹)—S(O)-heteroalkyl, —N(R²¹)—S(O)₂-heteroalkyl, —N(R²¹)—S(O)₂—N(R²¹)-heteroalkyl, —S(O)—N(R²¹)-heteroalkyl and —S(O)₂—N(R²¹)-heteroalkyl,
(8e) alkenyl, —O-alkenyl, —C(O)-alkenyl, —CO₂-alkenyl, —S-alkenyl, —S(O)-alkenyl, —S(O)₂-alkenyl, —N(R⁶)-alkenyl, —C(O)—N(R²¹)-alkenyl, —N(R²¹)—C(O)-alkenyl, —N(R²¹)—C(O)—N(R²¹)-alkenyl, —N(R²¹)—S(O)-alkenyl, —N(R²¹)—S(O)₂-alkenyl, —N(R²¹)—S(O)₂—N(R²¹)-alkenyl, —S(O)—N(R²¹)-alkenyl and —S(O)₂—N(R²¹)-alkenyl,
(9e) alkynyl, —O-alkynyl, —C(O)-alkynyl, —CO₂-alkynyl, —S-alkynyl, —S(O)-alkynyl, —S(O)₂-alkynyl, —N(R⁶)-alkynyl, —C(O)—N(R⁶)-alkynyl, —N(R²¹)—C(O)-alkynyl, —N(R²¹)—C(O)—N(R²¹)-alkynyl, —N(R²¹)—S(O)-alkynyl, —N(R²¹)—S(O)₂-alkynyl, —N(R²¹)—S(O)₂—N(R²¹)-alkynyl, —S(O)—N(R²¹)-alkynyl and —S(O)₂—N(R²¹)-alkynyl, (10e) aryl, —O-aryl, —C(O)-aryl, —CO₂-aryl, —S-aryl, —S(O)-aryl, —S(O)₂-aryl, —N(R⁶)-aryl, —C(O)—N(R²¹)-aryl, —N(R²¹)—C(O)-aryl, —N(R²¹)—C(O)—N(R²¹)-aryl, N(R²¹)—S(O)-aryl, —N(R²¹)—S(O)₂-aryl, —N(R²¹)—S(O)₂—N(R²¹)-aryl, —S(O)—N(R²¹)-aryl, and —S(O)₂—N(R²¹)-aryl, or (11e) heteroaryl, —O-heteroaryl, —C(O)-heteroaryl, —CO₂-heteroaryl, —S-heteroaryl, —S(O)-heteroaryl, —S(O)₂-heteroaryl, —N(R⁶)-heteroaryl, —C(O)—N(R²¹)-heteroaryl, —N(R²¹)—C(O)-heteroaryl, —N(R²¹)—C(O)—N(R²¹)-heteroaryl, —N(R²¹)—S(O)-heteroaryl, —N(R²¹)—S(O)₂-heteroaryl, —N(R²¹)—S(O)₂—N(R²¹)-heteroaryl, —S(O)—N(R²¹)-heteroaryl, and —S(O)₂—N(R²¹)-heteroaryl, wherein said heteroalkyl, said heterocycloalkyl, said heterocycloalkenyl, and said heteroaryl of R⁷ may be connected through any available carbon or heteroatom;

each R¹¹ is independently selected from H and $C_{1-3}$ alkyl;
each R¹² is independently selected from H, $C_{1-3}$ alkyl, —OH, and hydroxy-substituted $C_{1-3}$ alkyl;
each R¹³ is independently selected from H, unsubstituted $C_{1-3}$ alkyl, and $C_{1-3}$ alkyl substituted with one or more groups each independently selected from hydroxyl and alkoxy, or R¹² and R¹³ are taken together to form an oxo; and
each R¹⁴ is independently selected from H and fluoro.

2. A compound in accordance with claim 1 wherein each V is independently selected from the group consisting of: $C_{1-6}$alkyl and cycloalkyl.

3. A compound in accordance with claim 1 wherein:
G is selected from the group consisting of:
(1a) hydrogen, halo, —NH₂, —OH, CO₂H, and cyano;
(2a) cycloalkyl, —O-cycloalkyl, and —N(R¹)-cycloalkyl;
(3a) heterocycloalkyl, —O-heterocycloalkyl, and —N(R¹)-heterocycloalkyl;
(6a) alkyl, —O-alkyl and —N(R¹)alkyl;
(7a) heteroalkyl, —O-heteroalkyl, and —N(R¹)-heteroalkyl;
(8a) alkenyl, —O-alkenyl, and —N(R¹)-alkenyl,
(9a) alkynyl, —O-alkynyl, and —N(R¹)-alkynyl;
(10a) aryl, —O-aryl, —C(O)-aryl, —S-aryl, —S(O)-aryl, —S(O)₂-aryl, —N(R¹)-aryl, —C(O)—N(R²¹)-aryl;
(11a) heteroaryl, —O-heteroaryl, —C(O)-heteroaryl, —S-heteroaryl, —S(O)-heteroaryl, —S(O)₂-heteroaryl, —N(R¹)-heteroaryl, —C(O)—N(R²¹)-heteroaryl;
wherein said heteroalkyl, heterocycloalkyl, heterocycloalkenyl, and heteroaryl of G are connected through any available carbon or heteroatom,
and wherein said alkyl, heteroalkyl, cycloalkyl, heterocycloalkyl, aryl, said heteroaryl, alkenyl, alkynyl, cycloalkenyl, and heterocycloalkenyl of G are unsubstituted or substituted with one or more groups independently selected from R².

4. A compound in accordance with claim 1 wherein G represents a phenyl group optionally substituted with 1-3 groups selected from halo, $C_{1-3}$alkyl, $C_{1-3}$ alkoxy, halo$C_{1-3}$alkyl and halo$C_{1-3}$alkoxy, or with one phenyl ring that is optionally substituted with 1-3 halo atoms.

5. A compound in accordance with claim 1 wherein L¹ is selected from the group consisting of —N(R⁴)—(C(R⁵ᴬ)₂)—(C(R⁵)₂)$_q$—, —(C(R⁵ᴬ)₂)—(C(R⁵)₂)$_r$—(C(R⁵ᴬ)₂)—N (R⁴)—, —O—(C(R⁵ᴬ)₂)—(C(R⁵)₂)$_q$—, —(C(R⁵ᴬ)₂)—(C(R⁵)₂)$_r$—(C(R⁵ᴬ)₂)—O—, and —(C(R⁵ᴬ)₂)—(C(R⁵)₂)$_s$—.

6. A compound in accordance with claim 1 wherein L¹ is selected from the group consisting of a bond, —NH—(CH₂)₂—, —O—(CH₂)₂—, —O—, —NH—, —N(CH₃)—, —CH₂—, —CH($C_{1-6}$alkyl)- and —CH($C_{3-6}$cycloalkyl)-.

7. A compound in accordance with claim 1 wherein L¹ is selected from the group consisting of —CH₂—, —CH(CH₃)—, —CH₂CH₂—, —CH(CH₂CH₂CH₂CH₃)—, —CH(CH(CH₃)₂)—, —CH(cyclopropyl)- and —CH(CH₂CH(CH₃)₂)—.

8. A compound in accordance with claim 1 wherein ring B is phenyl.

9. A compound in accordance with claim 1 wherein ring B is a 5-6 membered heteroaromatic ring selected from the group consisting of: thiophene, pyridine, pyrimidine, pyrazine, pyridazine, and triazine.

10. A compound in accordance with claim 1 wherein R³ is H or is selected from the group consisting of: methyl, ethyl, n-propyl, and isopropyl.

11. A compound in accordance with claim 1 wherein Z is —CH₂CH₂C(O)OH.

12. A compound in accordance with claim 1 wherein Z is

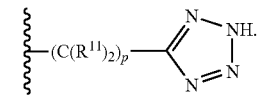

13. A compound represented by Formula (A):

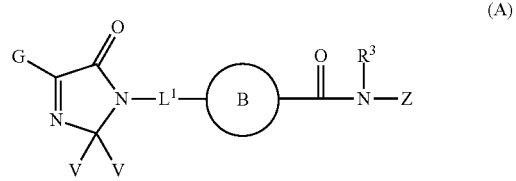

or a pharmaceutically acceptable salt thereof, wherein:
each V is independently selected from the group consisting of: $C_{1-6}$alkyl and cycloalkyl;
G represents a phenyl group optionally substituted with 1-3 groups selected from halo, $C_{1-3}$alkyl, $C_{1-3}$alkoxy, halo$C_{1-3}$alkyl and halo$C_{1-3}$alkoxy, or with one phenyl ring optionally substituted with 1-3 halo atoms;
L¹ represents —(C(R⁵ᴬ)₂)—(C(R⁵)₂)$_s$—; wherein s is 0-1, each R⁵ᴬ represents H, $C_{1-6}$alkyl or $C_{3-6}$cycloalkyl, and when present, each R⁵ represents H;
ring B is phenyl.
R³ is H;
Z is selected from the group consisting of: —CH₂CH₂CO₂H, and

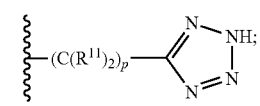

wherein p is 0-2 and when present each R¹¹ is H.

14. A compound in accordance with claim 1 selected from Table 1:
TABLE 1
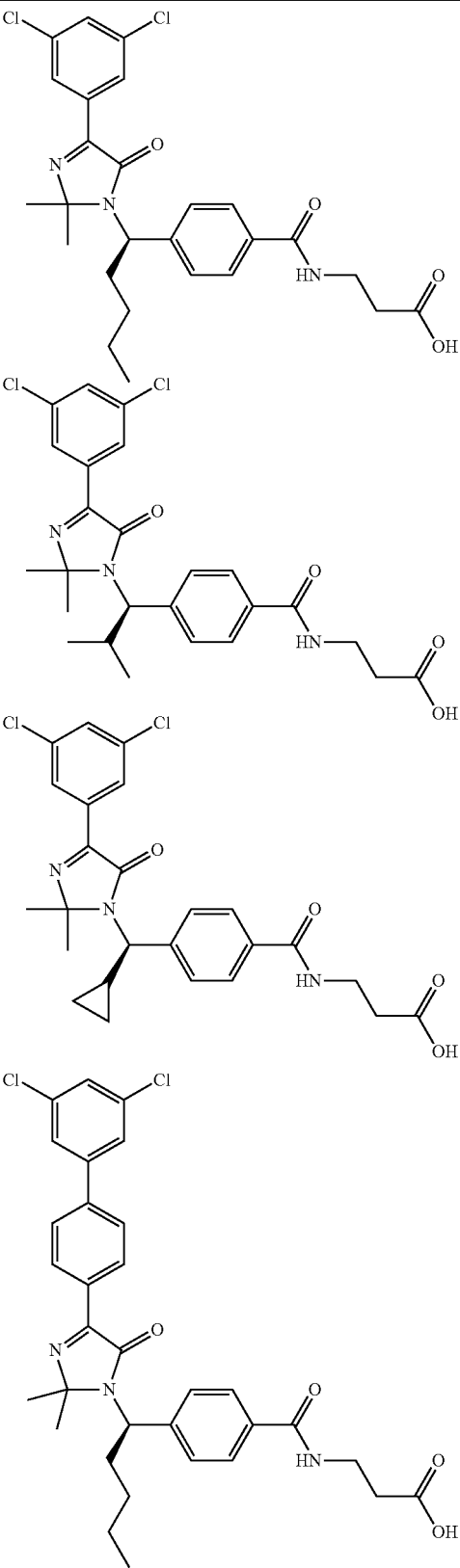
TABLE 1-continued
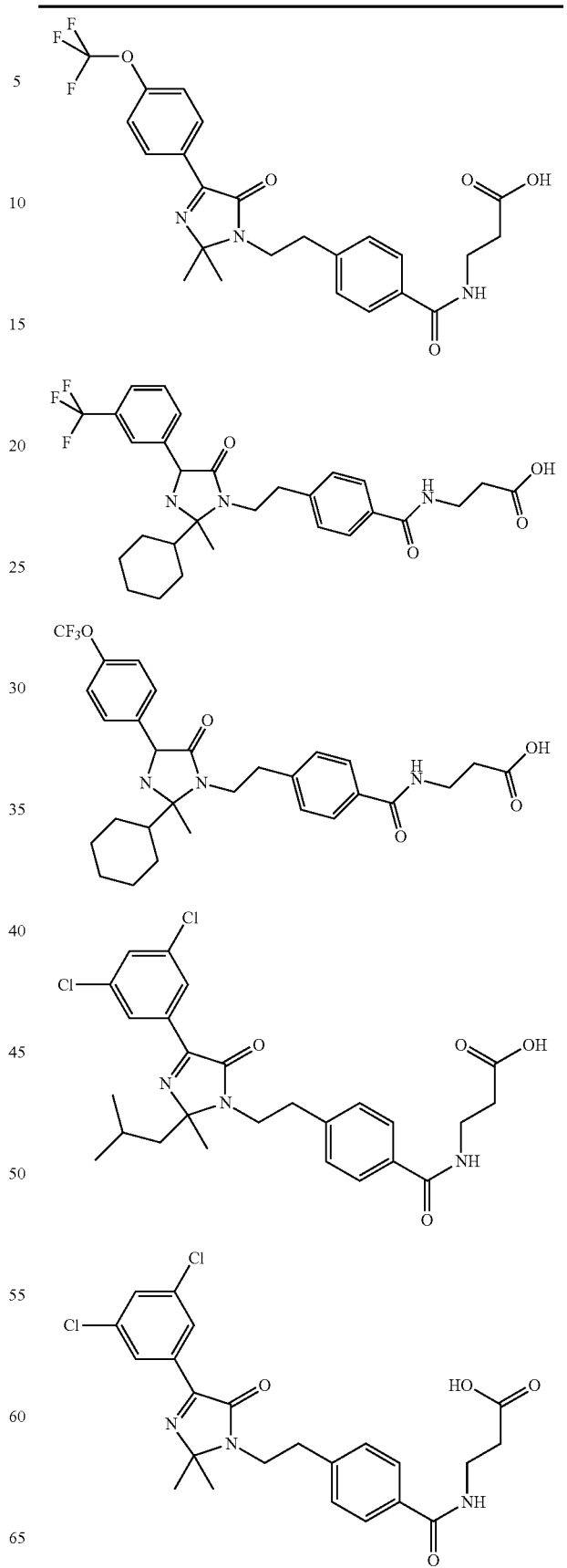

TABLE 1-continued
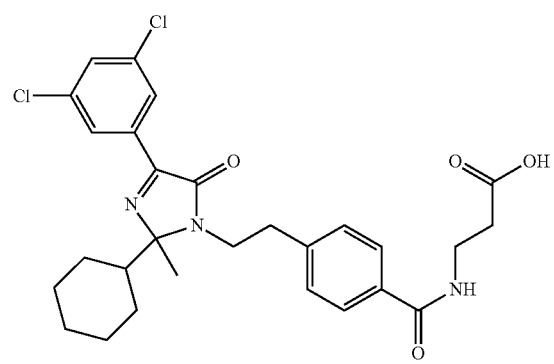 [SMILES: CC1(C2CCCCC2)N=C(c2cc(Cl)cc(Cl)c2)C(=O)N1CCc1ccc(C(=O)NCCC(=O)O)cc1]
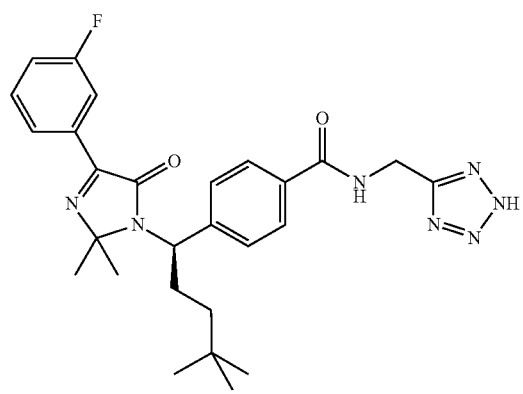 [SMILES: CC(C)(C)CC[C@H](c1ccc(C(=O)NCc2nn[nH]n2)cc1)N1C(=O)C(c2cccc(F)c2)=NC1(C)C]
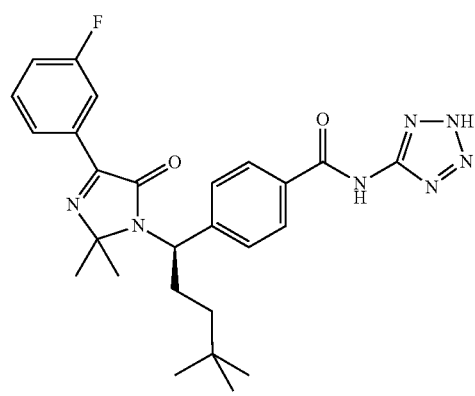 [SMILES: CC(C)(C)CC[C@H](c1ccc(C(=O)Nc2nn[nH]n2)cc1)N1C(=O)C(c2cccc(F)c2)=NC1(C)C]
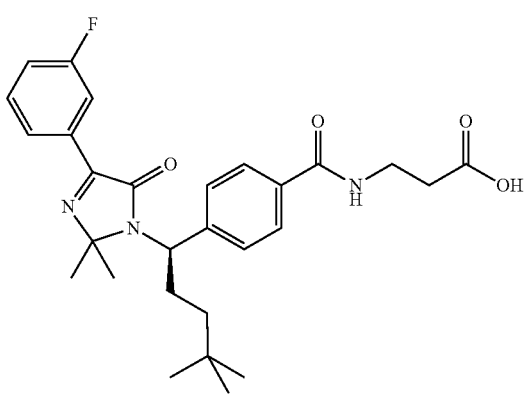 [SMILES: CC(C)(C)CC[C@H](c1ccc(C(=O)NCCC(=O)O)cc1)N1C(=O)C(c2cccc(F)c2)=NC1(C)C]
TABLE 1-continued
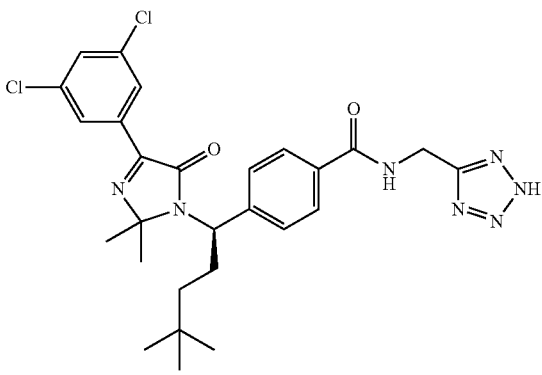 [SMILES: CC(C)(C)CC[C@H](c1ccc(C(=O)NCc2nn[nH]n2)cc1)N1C(=O)C(c2cc(Cl)cc(Cl)c2)=NC1(C)C]
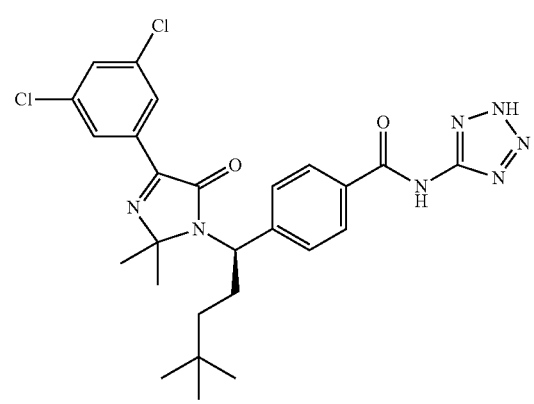 [SMILES: CC(C)(C)CC[C@H](c1ccc(C(=O)Nc2nn[nH]n2)cc1)N1C(=O)C(c2cc(Cl)cc(Cl)c2)=NC1(C)C]
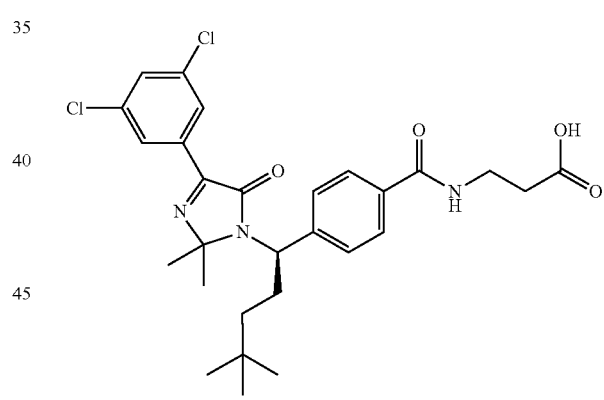
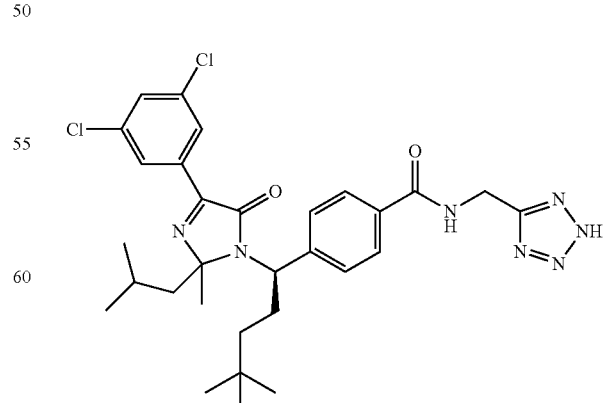

TABLE 1-continued

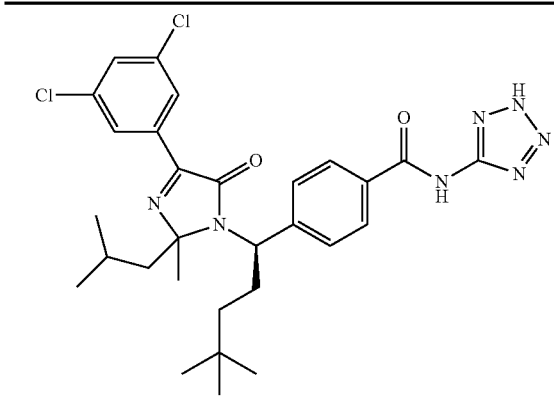

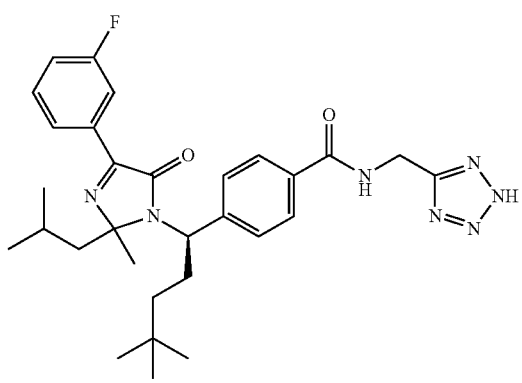 [SMILES: CC(C)CC1(C)N=C(c2cccc(F)c2)C(=O)N1[C@H](CCC(C)(C)C)c1ccc(C(=O)NCc2nn[nH]n2)cc1]

TABLE 1-continued

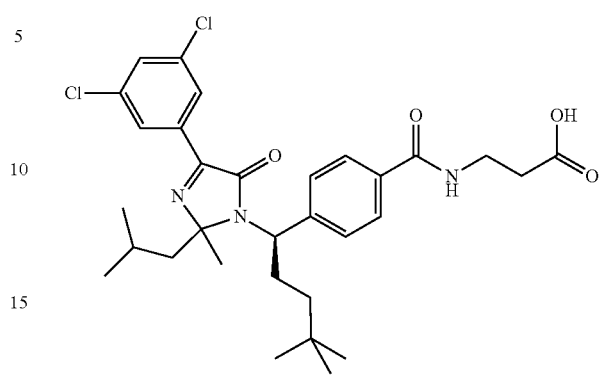

or a pharmaceutically acceptable salt thereof.

15. A pharmaceutical composition comprising a compound in accordance with claim 1 or a pharmaceutically acceptable salt thereof in combination with a pharmaceutically acceptable carrier.

16. A method of treating type 2 diabetes mellitus in a mammalian patient in need of such treatment comprising administering to the patient a compound in accordance with claim 1 in an amount that is effective to treat type 2 diabetes mellitus.

* * * * *